(12) United States Patent
Wong

(10) Patent No.: US 9,090,693 B2
(45) Date of Patent: Jul. 28, 2015

(54) USE OF ANTI-EGFR ANTIBODIES IN TREATMENT OF EGFR MUTANT MEDIATED DISEASE

(75) Inventor: Kwok-Kin Wong, Arlington, MA (US)

(73) Assignee: Dana-Farber Cancer Institute, Boston, MA (US)

( * ) Notice: Subject to any disclaimer, the term of this patent is extended or adjusted under 35 U.S.C. 154(b) by 962 days.

(21) Appl. No.: 12/449,129

(22) PCT Filed: Jan. 24, 2008

(86) PCT No.: PCT/US2008/001024
§ 371 (c)(1),
(2), (4) Date: Nov. 12, 2009

(87) PCT Pub. No.: WO2008/091701
PCT Pub. Date: Jul. 31, 2008

(65) Prior Publication Data
US 2010/0166744 A1 Jul. 1, 2010

Related U.S. Application Data

(60) Provisional application No. 60/897,383, filed on Jan. 25, 2007.

(51) Int. Cl.
*C07K 16/28* (2006.01)
*A61K 39/00* (2006.01)

(52) U.S. Cl.
CPC ....... *C07K 16/2863* (2013.01); *A61K 2039/505* (2013.01)

(58) Field of Classification Search
CPC ... A61K 6/00; A61K 39/00; A61K 2039/505; A61K 48/00; C12Y 101/00; C12Y 207/00; C12Y 207/11; C12Y 207/11001; C07K 1/00; C07K 16/00; C07K 16/18; C07K 16/28; C07K 16/2851; C07K 16/2863
See application file for complete search history.

(56) References Cited

U.S. PATENT DOCUMENTS

| | | | |
|---|---|---|---|
| 4,137,230 A | 1/1979 | Hashimoto |
| 4,151,042 A | 4/1979 | Higashide |
| 4,169,888 A | 10/1979 | Hanka |
| 4,190,580 A | 2/1980 | Hashimoto |
| 4,225,494 A | 9/1980 | Higashide |
| 4,248,870 A | 2/1981 | Miyashita |
| 4,256,746 A | 3/1981 | Miyashita |
| 4,260,608 A | 4/1981 | Miyashita |
| 4,263,294 A | 4/1981 | Miyashita |
| 4,264,596 A | 4/1981 | Miyashita |
| 4,265,814 A | 5/1981 | Hashimoto |
| 4,294,757 A | 10/1981 | Asai |
| 4,307,016 A | 12/1981 | Asai |
| 4,308,268 A | 12/1981 | Miyashita |
| 4,308,269 A | 12/1981 | Miyashita |
| 4,309,428 A | 1/1982 | Miyashita |
| 4,313,946 A | 2/1982 | Powell |
| 4,317,821 A | 3/1982 | Miyashita |
| 4,322,348 A | 3/1982 | Asai |
| 4,331,598 A | 5/1982 | Hasegawa |
| 4,342,566 A | 8/1982 | Theofilopoulos et al. |
| 4,360,462 A | 11/1982 | Higashide |
| 4,361,650 A | 11/1982 | Asai |
| 4,362,663 A | 12/1982 | Kida |
| 4,364,866 A | 12/1982 | Asai |
| 4,371,533 A | 2/1983 | Akimoto |
| 4,413,132 A | 11/1983 | Wierenga |
| 4,418,064 A | 11/1983 | Powell |
| 4,671,958 A | 6/1987 | Rodwell |
| 4,762,707 A | 8/1988 | Jansen |
| 4,816,567 A | 3/1989 | Cabilly et al. |
| 4,867,973 A | 9/1989 | Goers |
| 4,933,294 A | 6/1990 | Waterfield |
| 4,937,183 A | 6/1990 | Ultee |
| 4,943,533 A | 7/1990 | Mendelsohn et al. |
| 4,952,394 A | 8/1990 | Senter |
| 4,997,913 A | 3/1991 | Hellstrom |
| 5,013,547 A | 5/1991 | Sweet |
| 5,028,697 A | 7/1991 | Johnson |
| 5,034,223 A | 7/1991 | Abrams |

(Continued)

FOREIGN PATENT DOCUMENTS

| | | |
|---|---|---|
| EP | 120694 | 10/1984 |
| EP | 125023 | 11/1984 |

(Continued)

OTHER PUBLICATIONS

U.S. Appl. No. 60/290,410, filed May 11, 2001.
U.S. Appl. No. 60/326,019, filed Sep. 28, 2001.
U.S. Appl. No. 60/342,258, filed Dec. 21, 2001.
EP, 1392359 A4 Supplementary European Search Report, Old, Sep. 23, 2005.
EP, 1392359B1 Notice of Opposition, Jul. 21, 2010.
EP, 1722808 A4 Supplementary Partial European Search Report, Johns, Jul. 13, 2009.
EP, 20068929 A4 Supplementary European Search Report, Fiore, Mar. 10, 2010.
EP, 2134854 A4 Supplementary European Search Report, Johns, Jan. 17, 2011.
EP, 2163256 A3 European Search Report, Old, Feb. 3, 2010.
EP, 10186053 A3 Extended European Search Report, Old, May 11, 2011.

(Continued)

*Primary Examiner* — Alana Harris Dent
(74) *Attorney, Agent, or Firm* — McCarter & English, LLP; Cristin H. Cowles; Maneesh Gulati, Esq.

(57) ABSTRACT

The present invention relates to the treatment of EGFR-mediated disease, particularly cancer, which is resistant to tyrosine kinase inhibitor therapies. Methods for treatment of cancer and reduction of tumor growth in individuals with secondary EGFR mutations, particularly tyrosine kinase domain mutations, resistant to standard therapy are provided. The invention provides methods for the treatment of tyrosine kinase inhibitor resistant cancers with anti-EGFR antibodies. Methods for treatment of recurrent lung cancer, including non-small cell lung carcinoma which is resistant to tyrosine kinase inhibitors, with the antibody anti-EGFR mAb806 are described.

18 Claims, 5 Drawing Sheets

(56) References Cited

U.S. PATENT DOCUMENTS

| | | |
|---|---|---|
| 5,047,324 A | 9/1991 | Fredrickson |
| 5,087,616 A | 2/1992 | Myers |
| 5,106,951 A | 4/1992 | Morgan |
| 5,122,368 A | 6/1992 | Greenfield |
| 5,130,116 A | 7/1992 | Woo |
| 5,141,736 A | 8/1992 | Iwasa |
| 5,164,311 A | 11/1992 | Gupta |
| 5,171,563 A | 12/1992 | Abrams |
| 5,208,020 A | 5/1993 | Chari |
| 5,212,290 A | 5/1993 | Vogelstein |
| 5,217,713 A | 6/1993 | Iwasa |
| 5,225,539 A | 7/1993 | Winter |
| 5,306,809 A | 4/1994 | Boon |
| 5,332,837 A | 7/1994 | Kelly |
| 5,401,828 A | 3/1995 | Vogelstein et al. |
| 5,416,064 A | 5/1995 | Chari |
| 5,457,105 A | 10/1995 | Barker |
| 5,459,061 A | 10/1995 | Sato |
| 5,475,092 A | 12/1995 | Chari |
| 5,541,339 A | 7/1996 | Kelly |
| 5,556,623 A | 9/1996 | Barton |
| 5,558,864 A | 9/1996 | Bendig |
| 5,563,250 A | 10/1996 | Hylarides |
| 5,585,499 A | 12/1996 | Chari |
| 5,606,017 A | 2/1997 | Willner |
| 5,612,474 A | 3/1997 | Patel |
| 5,622,929 A | 4/1997 | Willner |
| 5,635,483 A | 6/1997 | Pettit |
| 5,635,603 A | 6/1997 | Hansen |
| 5,639,641 A | 6/1997 | Pedersen |
| 5,643,573 A | 7/1997 | Barton |
| 5,665,358 A | 9/1997 | Barton |
| 5,674,977 A | 10/1997 | Gariepy |
| 5,677,171 A | 10/1997 | Hudziak |
| 5,708,146 A | 1/1998 | Willner |
| 5,708,156 A | 1/1998 | Ilekis |
| 5,720,954 A | 2/1998 | Hudziak |
| 5,739,350 A | 4/1998 | Kelly |
| 5,760,041 A | 6/1998 | Wissner |
| 5,770,195 A | 6/1998 | Hudziak |
| 5,780,588 A | 7/1998 | Pettit |
| 5,795,965 A | 8/1998 | Tsuchiya |
| 5,807,715 A | 9/1998 | Morrison |
| 5,814,317 A | 9/1998 | Vogelstein |
| 5,824,805 A | 10/1998 | King |
| 5,844,093 A | 12/1998 | Kettleborough |
| 5,846,545 A | 12/1998 | Chari |
| 5,851,526 A | 12/1998 | Welt |
| 5,869,045 A | 2/1999 | Hellstrom |
| 5,869,619 A | 2/1999 | Studnicka |
| 5,880,270 A | 3/1999 | Berninger |
| 5,891,996 A | 4/1999 | De Acosta Del Rio |
| 5,911,995 A | 6/1999 | Uckun |
| 5,942,602 A | 8/1999 | Wels |
| 5,980,896 A | 11/1999 | Hellstrom |
| 6,010,902 A | 1/2000 | Ledbetter |
| 6,060,608 A | 5/2000 | Boger |
| 6,214,345 B1 | 4/2001 | Firestone |
| 6,217,866 B1 | 4/2001 | Schlessinger |
| 6,224,868 B1 | 5/2001 | Wong |
| 6,235,883 B1 | 5/2001 | Jakobovits |
| 6,281,354 B1 | 8/2001 | Boger |
| 6,306,393 B1 | 10/2001 | Goldenberg |
| 6,331,175 B1 | 12/2001 | Goldenberg |
| 6,331,415 B1 | 12/2001 | Cabilly |
| 6,333,410 B1 | 12/2001 | Chari |
| 6,340,701 B1 | 1/2002 | Chari |
| 6,372,738 B2 | 4/2002 | Chari |
| 6,395,272 B1 | 5/2002 | Deo |
| 6,436,931 B1 | 8/2002 | Chari |
| 6,441,163 B1 | 8/2002 | Chari |
| 6,506,883 B2 | 1/2003 | De Acosta Del Rio |
| 6,512,101 B1 | 1/2003 | King |
| RE38,008 E | 2/2003 | Abrams |
| 6,534,660 B1 | 3/2003 | Yongxin |
| 6,548,530 B1 | 4/2003 | Boger |
| 6,570,024 B2 | 5/2003 | Eldridge |
| 6,586,618 B1 | 7/2003 | Zhao |
| 6,596,757 B1 | 7/2003 | Chari |
| 6,630,579 B2 | 10/2003 | Chari |
| 6,660,742 B2 | 12/2003 | Lee |
| 6,699,715 B1 | 3/2004 | Ledbetter |
| 6,706,708 B2 | 3/2004 | Chari |
| 6,716,821 B2 | 4/2004 | Zhao |
| 6,756,397 B2 | 6/2004 | Zhao |
| 6,759,509 B1 | 7/2004 | King |
| 6,790,954 B2 | 9/2004 | Chung |
| 6,797,492 B2 | 9/2004 | Daugherty |
| 6,884,869 B2 | 4/2005 | Senter |
| 6,884,874 B2 | 4/2005 | Eldridge |
| 6,913,748 B2 | 7/2005 | Widdison |
| 6,946,543 B2 | 9/2005 | Ward |
| 6,989,452 B2 | 1/2006 | Ng |
| 7,008,942 B2 | 3/2006 | Chari |
| 7,049,316 B2 | 5/2006 | Zhao |
| 7,060,808 B1 | 6/2006 | Goldstein |
| 7,091,186 B2 | 8/2006 | Senter |
| 7,097,840 B2 | 8/2006 | Erickson |
| 7,098,308 B2 | 8/2006 | Senter |
| 7,129,261 B2 | 10/2006 | Ng |
| 7,129,332 B2 | 10/2006 | Pastan |
| 7,132,511 B2 | 11/2006 | Carr |
| 7,132,554 B2 | 11/2006 | Rose |
| 7,192,750 B2 | 3/2007 | Chung |
| 7,214,685 B2 | 5/2007 | Tietze |
| 7,217,819 B2 | 5/2007 | Chari |
| 7,223,837 B2 | 5/2007 | De Groot |
| 7,226,592 B2 | 6/2007 | Kreysch |
| 7,247,301 B2 | 7/2007 | Van De Winkel |
| 7,256,257 B2 | 8/2007 | Doronina |
| 7,276,497 B2 | 10/2007 | Chari |
| 7,276,499 B2 | 10/2007 | Chari |
| 7,276,585 B2 | 10/2007 | Lazar |
| 7,301,019 B2 | 11/2007 | Widdison |
| 7,303,749 B1 | 12/2007 | Chari |
| 7,329,760 B2 | 2/2008 | Zhao |
| 7,368,565 B2 | 5/2008 | Chari |
| 7,374,762 B2 | 5/2008 | Amphlett |
| 7,375,078 B2 | 5/2008 | Feng |
| 7,388,026 B2 | 6/2008 | Zhao |
| 7,390,898 B2 | 6/2008 | Baloglu |
| 7,411,063 B2 | 8/2008 | Widdison |
| 7,414,073 B2 | 8/2008 | Baloglu |
| 7,423,116 B2 | 9/2008 | Doronina |
| 7,432,088 B2 | 10/2008 | Kuo |
| 7,449,559 B2 | 11/2008 | Ward |
| 7,473,796 B2 | 1/2009 | Chari |
| 7,476,669 B2 | 1/2009 | Chari |
| 7,494,649 B2 | 2/2009 | Amphlett |
| 7,495,114 B2 | 2/2009 | Baloglu |
| 7,498,298 B2 | 3/2009 | Doronina |
| 7,498,302 B2 | 3/2009 | Ng |
| 7,501,120 B2 | 3/2009 | Amphlett |
| 7,514,080 B2 | 4/2009 | Amphlett |
| 7,517,903 B2 | 4/2009 | Chen |
| 7,521,541 B2 | 4/2009 | Eigenbrot |
| 7,528,130 B2 | 5/2009 | Chari |
| 7,550,609 B2 | 6/2009 | Chari |
| 7,553,816 B2 | 6/2009 | Senter |
| 7,575,748 B1 | 8/2009 | Erickson |
| 7,585,857 B2 | 9/2009 | Chari |
| 7,589,180 B2 | 9/2009 | Old |
| 7,595,378 B2 | 9/2009 | Van De Winkel |
| 7,598,290 B2 | 10/2009 | Miller |
| 7,598,375 B2 | 10/2009 | Ho |
| 7,601,354 B2 | 10/2009 | Chari |
| 7,628,986 B2 | 12/2009 | Weber |
| 7,635,570 B2 | 12/2009 | Siena |
| 7,651,687 B2 | 1/2010 | Buck |
| 7,655,660 B2 | 2/2010 | Zhao |
| 7,655,661 B2 | 2/2010 | Zhao |
| 7,659,241 B2 | 2/2010 | Senter |
| 7,667,054 B2 | 2/2010 | Miller |
| 7,691,962 B2 | 4/2010 | Boyd |

(56) References Cited

U.S. PATENT DOCUMENTS

| | | |
|---|---|---|
| 7,723,484 B2 | 5/2010 | Beidler |
| 7,736,644 B2 | 6/2010 | Weber |
| 7,745,394 B2 | 6/2010 | Doronina |
| 7,750,116 B1 | 7/2010 | Doronina |
| 7,754,681 B2 | 7/2010 | Feng |
| 7,767,792 B2 | 8/2010 | Johns |
| 7,790,164 B2 | 9/2010 | Cao |
| 7,807,798 B2 | 10/2010 | Jakobovits |
| 2001/0005747 A1 | 6/2001 | Ball |
| 2001/0036923 A1 | 11/2001 | Chari |
| 2001/0046686 A1 | 11/2001 | Wong |
| 2001/0048922 A1 | 12/2001 | Romet-Lemonne |
| 2001/0055595 A1 | 12/2001 | Goldenberg |
| 2002/0001587 A1 | 1/2002 | Erickson |
| 2002/0004587 A1 | 1/2002 | Miller |
| 2002/0006379 A1 | 1/2002 | Hansen |
| 2002/0012663 A1 | 1/2002 | Waksal |
| 2002/0013485 A1 | 1/2002 | Chari |
| 2002/0049335 A1 | 4/2002 | Boger |
| 2002/0062009 A1 | 5/2002 | Taylor |
| 2002/0064785 A1 | 5/2002 | Mass |
| 2002/0082424 A1 | 6/2002 | Boger |
| 2002/0156274 A1 | 10/2002 | Terfloth |
| 2002/0173629 A1 | 11/2002 | Jakobovits |
| 2003/0050331 A1 | 3/2003 | Ng |
| 2003/0055226 A1 | 3/2003 | Chari |
| 2003/0073731 A1 | 4/2003 | Lee |
| 2003/0073852 A1 | 4/2003 | Ng |
| 2003/0083263 A1 | 5/2003 | Doronina |
| 2003/0091561 A1 | 5/2003 | Van De Winkel |
| 2003/0096743 A1 | 5/2003 | Senter |
| 2003/0109682 A1 | 6/2003 | Santi |
| 2003/0130189 A1 | 7/2003 | Senter |
| 2003/0194403 A1 | 10/2003 | Van De Winkel |
| 2003/0195365 A1 | 10/2003 | Zhao |
| 2003/0199519 A1 | 10/2003 | Zhao |
| 2003/0211097 A1 | 11/2003 | Pastan |
| 2003/0211112 A1 | 11/2003 | Debinski |
| 2003/0215387 A1 | 11/2003 | Harrison |
| 2003/0224001 A1 | 12/2003 | Goldstein |
| 2004/0006212 A1 | 1/2004 | Goldstein |
| 2004/0033543 A1 | 2/2004 | Schwab |
| 2004/0086943 A1 | 5/2004 | Andres |
| 2004/0109867 A1 | 6/2004 | Yongxin |
| 2004/0131611 A1 | 7/2004 | Oliver |
| 2004/0147428 A1 | 7/2004 | Pluenneke |
| 2004/0157782 A1 | 8/2004 | Doronina |
| 2004/0202666 A1 | 10/2004 | Griffiths |
| 2004/0235074 A1 | 11/2004 | Siegall |
| 2004/0235840 A1 | 11/2004 | Chari |
| 2004/0248196 A1 | 12/2004 | Adams |
| 2004/0253645 A1 | 12/2004 | Daugherty |
| 2005/0009751 A1 | 1/2005 | Senter |
| 2005/0014700 A1 | 1/2005 | Boger |
| 2005/0026987 A1 | 2/2005 | Boger |
| 2005/0031627 A1 | 2/2005 | Mazzola |
| 2005/0032860 A1 | 2/2005 | Boger |
| 2005/0053608 A1 | 3/2005 | Weber |
| 2005/0059087 A1 | 3/2005 | Weber |
| 2005/0064492 A1 | 3/2005 | DeSauvage |
| 2005/0100546 A1 | 5/2005 | Jakobovits |
| 2005/0106644 A1 | 5/2005 | Cairns |
| 2005/0107595 A1 | 5/2005 | Cairns |
| 2005/0113308 A1 | 5/2005 | Senter |
| 2005/0113571 A1 | 5/2005 | Terfloth |
| 2005/0142133 A1 | 6/2005 | Lazar |
| 2005/0152913 A1 | 7/2005 | Eldridge |
| 2005/0169933 A1 | 8/2005 | Steeves |
| 2005/0214310 A1 | 9/2005 | Toki |
| 2005/0227324 A1 | 10/2005 | Huang |
| 2005/0238640 A1 | 10/2005 | Sliwkowski |
| 2005/0238649 A1 | 10/2005 | Doronina |
| 2005/0255555 A1* | 11/2005 | Johns et al. .................. 435/69.1 |
| 2005/0256030 A1 | 11/2005 | Feng |
| 2005/0271671 A1 | 12/2005 | Griffiths |
| 2005/0272083 A1* | 12/2005 | Seshagiri .................. 435/6 |
| 2005/0272798 A1 | 12/2005 | Ng |
| 2005/0276812 A1 | 12/2005 | Ebens |
| 2006/0004081 A1 | 1/2006 | Chen |
| 2006/0009462 A1 | 1/2006 | Yongxin |
| 2006/0024317 A1 | 2/2006 | Boyd |
| 2006/0074008 A1 | 4/2006 | Senter |
| 2006/0084141 A1 | 4/2006 | Floss |
| 2006/0088523 A1 | 4/2006 | Andya |
| 2006/0116422 A1 | 6/2006 | De Groot |
| 2006/0121044 A1 | 6/2006 | Amler et al. |
| 2006/0147959 A1 | 7/2006 | Bell |
| 2006/0154334 A1 | 7/2006 | Tarnowski |
| 2006/0165685 A1 | 7/2006 | Kreysch |
| 2006/0182750 A1 | 8/2006 | Chari |
| 2006/0183887 A1 | 8/2006 | Jakobovits |
| 2006/0229253 A1 | 10/2006 | Doronina |
| 2006/0234343 A1 | 10/2006 | Ward |
| 2006/0247295 A1 | 11/2006 | Gangwar |
| 2007/0020261 A1* | 1/2007 | Sliwkowski et al. ...... 424/141.1 |
| 2007/0031402 A1 | 2/2007 | Zhang |
| 2007/0037972 A1 | 2/2007 | Ho |
| 2007/0048314 A1 | 3/2007 | Dai |
| 2007/0071675 A1 | 3/2007 | Wu |
| 2007/0092940 A1 | 4/2007 | Eigenbrot |
| 2007/0112188 A1 | 5/2007 | Widdison |
| 2007/0116707 A1 | 5/2007 | Goldstein |
| 2007/0134243 A1 | 6/2007 | Gazzard |
| 2007/0135346 A1 | 6/2007 | Zhao |
| 2007/0202101 A1 | 8/2007 | Rosen |
| 2007/0264266 A1 | 11/2007 | Chari |
| 2007/0269447 A1 | 11/2007 | Chari |
| 2007/0270585 A1 | 11/2007 | Chari |
| 2008/0008704 A1 | 1/2008 | Rubin |
| 2008/0025983 A1 | 1/2008 | Adams |
| 2008/0114153 A1 | 5/2008 | Steeves |
| 2008/0145374 A1 | 6/2008 | Steeves |
| 2008/0171040 A1 | 7/2008 | Ebens |
| 2008/0171856 A1 | 7/2008 | Steeves |
| 2008/0171865 A1 | 7/2008 | Steeves |
| 2008/0226657 A1 | 9/2008 | Doronina |
| 2008/0226659 A1 | 9/2008 | Erickson |
| 2008/0241128 A1 | 10/2008 | Jeffrey |
| 2008/0248051 A1 | 10/2008 | Doronina |
| 2008/0248053 A1 | 10/2008 | Doronina |
| 2008/0249085 A1 | 10/2008 | Cassady |
| 2008/0260685 A1 | 10/2008 | Zhao |
| 2008/0267960 A1 | 10/2008 | Drachman |
| 2008/0279868 A1 | 11/2008 | Boyd |
| 2008/0281102 A1 | 11/2008 | Gangwar |
| 2008/0293800 A1 | 11/2008 | Gangwar |
| 2008/0300192 A1 | 12/2008 | Doronina |
| 2008/0305044 A1 | 12/2008 | McDonagh |
| 2008/0311136 A1 | 12/2008 | Beusker |
| 2009/0010945 A1 | 1/2009 | Alley |
| 2009/0018086 A1 | 1/2009 | Doronina |
| 2009/0028821 A1 | 1/2009 | Zhao |
| 2009/0041791 A1 | 2/2009 | Feng |
| 2009/0047296 A1 | 2/2009 | Doronina |
| 2009/0053240 A1 | 2/2009 | Lazar |
| 2009/0111756 A1 | 4/2009 | Doronina |
| 2009/0137782 A1 | 5/2009 | Old |
| 2009/0142361 A1 | 6/2009 | Amphlett |
| 2009/0155282 A1 | 6/2009 | Weber |
| 2009/0156790 A1 | 6/2009 | Weber |
| 2009/0175865 A1 | 7/2009 | Eigenbrot |
| 2009/0175887 A1 | 7/2009 | Weber |
| 2009/0175888 A1 | 7/2009 | Ng |
| 2009/0202536 A1 | 8/2009 | Ebens |
| 2009/0214541 A1 | 8/2009 | Gillies |
| 2009/0220510 A1 | 9/2009 | Old |
| 2009/0240038 A1 | 9/2009 | Weber |
| 2009/0269343 A1 | 10/2009 | Bigner |
| 2009/0274713 A1 | 11/2009 | Chari |
| 2009/0280503 A1 | 11/2009 | Fiore |
| 2009/0281158 A1 | 11/2009 | Zhao |
| 2009/0304693 A1 | 12/2009 | Ghayur |
| 2009/0306101 A1 | 12/2009 | Solca |
| 2009/0318668 A1 | 12/2009 | Beusker |

(56) References Cited

U.S. PATENT DOCUMENTS

| | | |
|---|---|---|
| 2009/0324621 A1 | 12/2009 | Senter |
| 2010/0008929 A1 | 1/2010 | Van De Winkel |
| 2010/0056762 A1 | 3/2010 | Old |
| 2010/0092475 A1 | 4/2010 | Johns |
| 2010/0166744 A1 | 7/2010 | Wong |
| 2010/0196265 A1 | 8/2010 | Adams |
| 2010/0203007 A1 | 8/2010 | Li |
| 2010/0322937 A1 | 12/2010 | Johns |
| 2011/0008766 A1 | 1/2011 | Ghayur |
| 2011/0076232 A1 | 3/2011 | Old |
| 2011/0150759 A1 | 6/2011 | Johns |

FOREIGN PATENT DOCUMENTS

| | | |
|---|---|---|
| EP | 0519596 A1 | 12/1992 |
| EP | 0586002 A2 | 3/1994 |
| EP | 0699755 A2 | 3/1996 |
| EP | 1392359 B1 | 10/2009 |
| EP | 2163256 A1 | 3/2010 |
| WO | WO 85/03357 A1 | 8/1985 |
| WO | WO 91/03489 A1 | 3/1991 |
| WO | WO 91/16350 A1 | 10/1991 |
| WO | WO 92/15683 A1 | 9/1992 |
| WO | WO 9311161 | 6/1993 |
| WO | WO 9413804 | 6/1994 |
| WO | WO 95/25167 A1 | 9/1995 |
| WO | WO 96/16988 A1 | 6/1996 |
| WO | WO 9640210 | 12/1996 |
| WO | WO 99/44645 A1 | 9/1999 |
| WO | WO 02/11677 A2 | 2/2002 |
| WO | WO 02092771 | 11/2002 |
| WO | WO 03/014159 A1 | 2/2003 |
| WO | WO 03068920 | 8/2003 |
| WO | WO 2004/003019 A2 | 1/2004 |
| WO | WO 2004/056847 A2 | 7/2004 |
| WO | WO 2004/085474 A2 | 10/2004 |
| WO | WO 2005/081854 A2 | 9/2005 |
| WO | WO 2005094357 | 10/2005 |
| WO | WO 2007/089149 A2 | 8/2007 |
| WO | WO 2007/103288 A2 | 9/2007 |
| WO | WO 2008/033495 A2 | 3/2008 |
| WO | WO 2008/091701 A2 | 7/2008 |
| WO | WO 2008/115404 A1 | 9/2008 |
| WO | WO 2008/154927 A1 | 12/2008 |
| WO | WO 2009/017394 A1 | 2/2009 |
| WO | WO 2009/023265 A1 | 2/2009 |
| WO | WO 2010/096434 A2 | 8/2010 |
| WO | WO 2011/035465 A1 | 3/2011 |
| WO | WO 2011/041319 A2 | 4/2011 |

OTHER PUBLICATIONS

WO, 02/092771 A1 International Preliminary Examination Report, Old, Nov. 3, 2003.
WO, 02/092771 A3 International Search Report, Old, Apr. 30, 2003.
WO, 2005/081854 A1 International Preliminary Report on Patentability, Johns, Aug. 22, 2006.
WO, 2005/081854 A1 International Search Report, Johns, Nov. 8, 2005.
WO, 2008/033495 A1 International Preliminary Report on Patentability, Fiore, Mar. 17, 2009.
WO, 2008/033495 A1 International Search Report, Fiore, Apr. 15, 2008.
WO, 2008/115404 A1 International Preliminary Report on Patentability, Johns, Sep. 15, 2009.
WO, 2008/115404 A1 International Search Report, Johns, Aug. 1, 2008.
WO, 2009/023265 A1 International Preliminary Report on Patentability, Johns, Feb. 16, 2010.
WO, 2009/023265 A1 International Search Report, Johns, May 1, 2009.
Abbruzzese et al., "Phase II study of anti-epidermal growth factor receptor (EGFR) antibody cetuximab (IMC-C225) in combination with gemcitabine in patients with advanced pancreatic cancer (Abstract 518)" *Proceedings of the American Society of Clinical Oncology* (2001) 130a, 20.
Aboud-Pirak et al., "Efficacy of antibodies to epidermal growth factor receptor against KB carcinoma in vitro and in nude mice" *Chemical Abstracts* (1989) 69068k, 110(9).
Aboud-Pirak et al., "Inhibition of human tumor growth in nude mice by a conjugate of doxorubicin with monoclonal antibodies to epidermal growth factor receptor." *Proceedings of the National Academy of Sciences of the United States of America* (1989) 3778-3781, 86(10).
Aboud-Pirak et al., "Efficacy of antibodies to epidermal growth factor receptor against KB carcinoma in vitro and in nude mice." *J. Natl. Cancer Inst.* (1988) 1605-1611, 80(20).
WO, 2010/096434 A1 International Preliminary Report on Patentability, Old, Aug. 23, 2011.
WO, 2010/096434 A3 International Search Report, Old, Aug. 26, 2010.
WO, 2010/096434 Invitation to Pay Fees, Apr. 6, 2010.
WO, 2011/041319 A1 International Search Report, Old, May 10, 2011.
Adams et al., "Monoclonal antibody therapy of cancer." *Nat. Biotechnol.* (2005) 1147-1157, 23(9).
Aden et al., "Cell Surface Antigens Coded for by the Human Chromosome 7" *Immunogenetics* (1976) 209-221, 3.
Aghajanian et al., "A phase II study of cetuximab/ paclitaxel/ carboplatin for the initial treatment of advanced stage ovarian, primary peritoneal, and fallopian tube cancer" *Journal of Clinical Oncology*, 2005 ASCO Annual Meeting Proceedings (2005) Abstract 5047, 23(16S; Part I of II: Jun. 1 Supplement).
Agosti et al., "Expression of the epidermal growth factor receptor in astrocytic tumours is specifically associated with glioblastoma multiforme." *Virchows Archiv. A, Pathological anatomy and histopathology* (1992) 321-325, 420(4).
Agulnik et al., "Predictive and pharmacodynamic biomarker studies in tumor and skin tissue samples of patients with recurrent or metastatic squamous cell carcinoma of the head and neck treated with erlotinib." *Journal of Clinical Oncology* (2007) 2184-2190, 25(16).
Agus et al., "Phase I clinical study of pertuzumab, a novel HER dimerization inhibitor, in patients with advanced cancer." *J. Clin. Oncol.* (2005) 2534-2543, 23(11).
Agus et al., "Targeting ligand-activated ErbB2 signaling inhibits breast and prostate tumor growth." *Cancer Cell* (2002) 127-137, 2(2).
Akiyama et al., "Genistein, a specific inhibitor of tyrosine-specific protein kinases." *JBC* (1987) 5592-5595, 262(12).
Albanell et al., "Activated extracellular signal-regulated kinases: association with epidermal growth factor receptor/transforming growth factor alpha expression in head and neck squamous carcinoma and inhibition by anti-epidermal growth factor receptor treatments." *Cancer Res.* (2001) 6500-6510, 61(17).
Albanell et al., "Pharmacodynamic studies of the epidermal growth factor receptor inhibitor ZD1839 in skin from cancer patients: histopathologic and molecular consequences of receptor inhibition." *J. Clin. Oncol.* (2002) 110-124, 20(1).
Albanell et al., "Pharmacodynamic studies with the epidermal growth factor receptor tyrosine kinase inhibitor ZD1839" *Seminars in Oncology* (2001) 56-66, 28.
Aldape et al., "Immunohistochemical detection of EGFRvIII in high malignancy grade astrocytomas and evaluation of prognostic significance." *Journal of neuropathology and experimental neurology* (2004) 700-707, 63(7).
Alimirah et al., "DU-145 and PC-3 human prostate cancer cell lines express androgen receptor: implications for the androgen receptor functions and regulation." *FEBS letters* (2006) 2294-2300, 580(9).
Alroy et al., "The ErbB signaling network in embryogenesis and oncogenesis: signal diversification through combinatorial ligand-receptor interactions." *FEBS letters* (1997) 83-86, 410(1).
Anderson et al., "ZD1839 (Iressa), a novel epidermal growth factor receptor (EGFR) tyrosine kinase inhibitor, potently inhibits the growth of EGFR-positive cancer cell lines with or without erbB2 overexpression." *Int. J. Cancer* (2001) 774-782, 94(6).
Andrews et al., "Cellular pharmacology of cisplatin: perspectives on mechanisms of acquired resistance." *Cancer cells* (Cold Spring Harbor, N.Y.: 1989) (1990) 35-43, 2(2).

(56) References Cited

OTHER PUBLICATIONS

Ang et al., "Epidermal growth factor receptor and response of head-and-neck carcinoma to therapy." *Int. J. Radiat. Oncol. Biol. Phys.* (2004) 959-965, 58(3).

Ang et al., "Impact of epidermal growth factor receptor expression on survival and pattern of relapse in patients with advanced head and neck carcinoma." *Cancer Res.* (2002) 7350-7356, 62(24).

Anido et al., "ZD1839, a specific epidermal growth factor receptor (EGFR) tyrosine kinase inhibitor, induces the formation of inactive EGFR/HER2 and EGFR/HER3 heterodimers and prevents heregulin signaling in HER2-overexpressing breast cancer cells." *Clin. Cancer Res.* (2003) 1274-1283, 9(4).

Archer et al., "Regional treatment of epidermal growth factor receptor vIII-expressing neoplastic meningitis with a single-chain immunotoxin, MR-1." *Clin. Cancer Res.* (1999) 2646-2652, 5(9).

Arteaga et al., "Antibodies Against p185HER2 Enhance Etoposide-Induced Cytotoxicity Against Human Breast Carcinoma Cells." *Proceedings of the American Society of Clinical Oncology* (1993) 75 (Abstract 101), 12.

Arteaga et al., "Tyrosine kinase inhibitors-ZD1839 (Iressa)." *Current opinion in oncology* (2001) 491-498, 13(6).

Arteaga, "The epidermal growth factor receptor: from mutant oncogene in nonhuman cancers to therapeutic target in human neoplasia." *J. Clin. Oncol.* (2001) 32S-40S, 19(18; Supplement).

Arteaga et al., "Unliganded epidermal growth factor receptor dimerization induced by direct interaction of quinazolines with the ATP binding site." *JBC* (1997) 23247-23254, 272(37).

Arteaga et al., "Tyrosine kinase inhibitors: why does the current process of clinical development not apply to them?" *Cancer Cell* (2004) 525-531, 5(6).

Arteaga, "Overview of epidermal growth factor receptor biology and its role as a therapeutic target in human neoplasia." *Semin. Oncol.* (2002) 3-9, 29(5 Suppl 14).

Arteaga et al., "Overview of rationale and clinical trials with signal transduction inhibitors in lung cancer." *Semin. Oncol.* (2002) 15-26, 29(1; Suppl. 4).

Arteaga, "Epidermal growth factor receptor dependence in human tumors: more than just expression?" *Oncologist* (2002) 31-39, 7(Suppl. 4).

Ashley et al., "Monoclonal antibodies to growth factors and growth factor receptors: their diagnostic and therapeutic potential in brain tumors." *Journal of neuro-oncology* (1997) 259-273, 35(3).

Atlas et al., "Growth regulation of human renal carcinoma cells: role of transforming growth factor alpha." *Cancer Res.* (1992) 3335-3339, 52(12).

Aujame et al., "High affinity human antibodies by phage display." *Human antibodies* (1997) 155-168, 8(4).

Austin et al., "Endocytosis and sorting of ErbB2 and the site of action of cancer therapeutics trastuzumab and geldanamycin." *Mol. Biol. Cell* (2004) 5268-5282, 15(12).

Azzazy et al., "Phage display technology: clinical applications and recent innovations." *Clinical biochemistry* (2002) 425-445, 35(6).

Baerga-Ortiz et al., "Epitope mapping of a monoclonal antibody against human thrombin by H/D-exchange mass spectrometry reveals selection of a diverse sequence in a highly conserved protein." *Protein science* (2002) 1300-1308, 11(6).

Bailey et al., "Evaluation of epidermal growth factor receptor (EGFR) as a predictive marker in patients with non-small-cell lung cancer (NSCLC) receiving first-line gefitinib combined with platinum-based chemotherapy" *Journal of Clinical Oncology*, 2004 ASCO Annual Meeting Proceedings (Post-Meeting Edition) (2004) Abstract 7013, 22(14S; Jul. 15 Supplement).

Balaban et al., "The effect of ionizing radiation on signal transduction: antibodies to EGF receptor sensitize A431 cells to radiation." *Biochimica et biophysica acta* (1996) 147-156, 1314(1-2).

Baly et al., "Development and characterization of a rhuMAb HER2 antibody ADCC assay for clinical evaluation of cytotoxic potency." *Proceedings of the American Association for Cancer Research* (1997) 27-28 (Abstract 181), 38.

Bandyopadhyay et al., "Physical interaction between epidermal growth factor receptor and DNA-dependent protein kinase in mammalian cells." *JBC* (1998) 1568-1573, 273(3).

Barendswaard et al., "Rapid and specific targeting of monoclonal antibody A33 to a colon cancer xenograft in nude mice." *Int. J. Oncol.* (1998) 45-53, 12(1).

Barnette et al., "Association of the anti-inflammatory activity of phosphodiesterase 4 (PDE4) inhibitors with either inhibition of PDE4 catalytic activity or competition for [3H]rolipram binding." *Biochemical pharmacology* (1996) 949-956, 51(7).

Baselga et al., "Phase I study of AEE788, a novel multitargeted inhibitor of ErbB and VEGF receptor family tyrosine kinases (A pharmacokinetic (PK)-pharmacodynamic (PD) study to identify the optimal therapeutic dose regimen)." *J. Clinical Oncology* (2005) Abstract 3028, 23.

Baselga et al., "Cetuximab (C225) plus cisplatin/carboplatin is active in patients (pts) with recurrent/metastatic squamous cell carcinoma of the head and neck (SCCHN) progressing on a same dose and schedule platinum-based regimen" *Proceedings of the American Society of Clinical Oncology* (2002) Abstract 900, 21.

Baselga et al., "Antitumor activity of paclitaxel in combination with anti-growth factor receptor monoclonal antibodies in breast cancer xenografts." *Proceedings of the American Association for Cancer Research* (1994) 380 (Abstract 2262), 35.

Baselga, "Combining the Anti-EGFR Agent Gefitinib With Chemotherapy in Non-Small-Cell Lung Cancer: How Do We Go From INTACT to Impact?" *Journal of Clinical Oncology* (2004) 759-761, 22(5).

Baselga et al., "Phase I safety, pharmacokinetic, and pharmacodynamic trial of ZD1839, a selective oral epidermal growth factor receptor tyrosine kinase inhibitor, in patients with five selected solid tumor types." *J. Clin. Oncol.* (2002) 4292-4302, 20(21).

Baselga et al., "Mechanism of action of trastuzumab and scientific update." *Semin. Oncol.* (2001) 4-11, 28(5; Suppl. 16).

Baselga, "Targeting the epidermal growth factor receptor: a clinical reality." *J. Clin. Oncol.* (2001) 41S-44S, 19(18; Supplement).

Baselga, "The EGFR as a target for anticancer therapy—focus on cetuximab." *Eur. J. Cancer* (2001) S16-22, 37 Suppl 4.

Baselga, "Clinical trails of Herceptin(R) (trastuzumab)." *Eur. J. Cancer* (2001) 18-24, 37 Suppl. 1.

Baselga, "Herceptin alone or in combination with chemotherapy in the treatment of HER2-positive metastatic breast cancer: pivotal trials." *Oncology* (2001) 14-21, 61(Suppl. 2).

Baselga et al., "Mechanism of action of anti-HER2 monoclonal antibodies." *Ann Oncol.* (2001) S35-41, 12(Suppl. 1).

Baselga et al., "Phase I studies of anti-epidermal growth factor receptor chimeric antibody C225 alone and in combination with cisplatin." *J. Clin. Oncol.* (2000) 904-914, 18(4).

Baselga et al., "Continuous Administration of ZD1839 (Iressa), a Novel Oral Epidermal Growth Factor Receptor Tyrosine Kinase Inhibitor (EGFR-TKI), in Patients with Five Selected Tumor Types: Evidence of Activity and Good Tolerability (Abstract 686)" *Proceedings of the American Society of Clinical Oncology* (2000) 177a, 19.

Baselga et al., "ZD1839 ('Iressa') as an anticancer agent." *Drugs* (2000) 33-40;.discussion 41-2, 60(Suppl. 1).

Baselga et al., "Recombinant humanized anti-HER2 antibody (Herceptin) enhances the antitumor activity of paclitaxel and doxorubicin against HER2/neu overexpressing human breast cancer xenografts." *Cancer Res.* (1998) 2825-2831, 58(13).

Baselga et al., "Phase II study of weekly intravenous recombinant humanized anti-p185HER2 monoclonal antibody in patients with HER2/neu-overexpressing metastatic breast cancer." *J. Clin. Oncol.* (1996) 737-744, 14(3).

Baselga et al., "Receptor blockade with monoclonal antibodies as anti-cancer therapy." *Pharmacology & Therapeutics* (1994) 127-154, 64(1).

Baselga et al., "Antitumor effects of doxorubicin in combination with anti-epidermal growth factor monoclonal antibodies." *J. Natl. Cancer Inst.* (1993) 1327-1333, 85(16).

Baselga, "Targeting tyrosine kinases in cancer: the second wave." *Science* (2006) 1175-1178, 312(5777).

Baselga et al., "Phase II multicenter study of the antiepidermal growth factor receptor monoclonal antibody cetuximab in combina-

(56) References Cited

OTHER PUBLICATIONS tion with platinum-based chemotherapy in patients with platinum-refractory metastatic and/or recurrent squamous cell carcinoma of the head and neck." *J. Clin. Oncol.* (2005) 5568-5577, 23(24).
Baselga et al., "Phase II and tumor pharmacodynamic study of gefitinib in patients with advanced breast cancer." *J. Clin. Oncol.* (2005) 5323-5333, 23(23).
Baselga et al., "Critical update and emerging trends in epidermal growth factor receptor targeting in cancer." *J. Clin. Oncol.* (2005) 2445-2459, 23(11).
Baselga et al., "Phase II study of efficacy, safety, and pharmacokinetics of trastuzumab monotherapy administered on a 3-weekly schedule." *J. Clin. Oncol.* (2005) 2162-2171, 23(10).
Baselga, "Why the epidermal growth factor receptor? The rationale for cancer therapy." *Oncologist* (2002) 2-8, 7(Suppl. 4).
Batra et al., "Epidermal growth factor ligand-independent, unregulated, cell-transforming potential of a naturally occurring human mutant EGFRvIII gene." *Cell growth & differentiation : the molecular biology journal of the American Association for Cancer Research* (1995) 1251-1259, 6(10).
Beckmann et al., "Expression analyses of epidermal growth factor receptor and HER-2/neu: no advantage of prediction of recurrence or survival in breast cancer patients." *Oncology* (1996) 441-447, 53(6).
Beers et al., "Immunotoxins with increased activity against epidermal growth factor receptor vIII-expressing cells produced by antibody phage display." *Clin. Cancer Res.* (2000) 2835-2843, 6(7).
Behr et al., "Radioimmunotherapy of small volume disease of colorectal cancer metastatic to the liver: preclinical evaluation in comparison to standard chemotherapy and initial results of a phase I clinical study." *Clin. Cancer Res.* (1999) 3232s-3242s, 5(10; Supplement).
Bell et al., "Inherited susceptibility to lung cancer may be associated with the T790M drug resistance mutation in EGFR." *Nature Genetics* (2005) 1315-1316, 37(12).
Bell et al., "Epidermal growth factor receptor mutations and gene amplification in non-small-cell lung cancer: molecular analysis of the IDEAL/INTACT gefitinib trials." *J. Clin. Oncol.* (2005) 8081-8092, 23(31).
Bender et al., "Immunotherapy of human glioma xenografts with unlabeled, 131I-, or 125I-labeled monoclonal antibody 425 to epidermal growth factor receptor." *Cancer Res.* (1992) 121-126, 52(1).
Benichou et al., "Random fragment libraries using yeast expression plasmid." *Methods Mol. Biol.* (1996) 241-255, 66.
Bequinot et al., "Down-regulation of the epidermal growth factor receptor in KB cells is due to receptor internalization and subsequent degradation in lysosomes" *Chemical Abstracts* (1984) Abstract,1592k, p. 141, 101(1).
Berkers et al., "The effects of receptor density and cell shape on epidermal growth factor binding." *Journal of Receptor Research* (1992) 71-100, 12(1).
Bernier, "Cetuximab in the treatment of head and neck cancer." *Expert review of anticancer therapy* (2006) 1539-1552, 6(11).
Bertics et al., "Alteration of epidermal growth factor receptor activity by mutation of its primary carboxyl-terminal site of tyrosine self-phosphorylation." *JBC* (1988) 3610-3617, 263(8).
Bertics et al., "Self-phosphorylation enhances the protein-tyrosine kinase activity of the epidermal growth factor receptor." *JBC* (1985) 14642-14647, 260(27).
Bhattacharya-Chatterjee et al., "The anti-idiotype vaccines for immunotherapy." *Current opinion in molecular therapeutics* (2001) 63-69, 3(1).
Bianco et al., "Antitumor activity of combined treatment of human cancer cells with ionizing radiation and anti-epidermal growth factor receptor monoclonal antibody C225 plus type I protein kinase A antisense oligonucleotide." *Clin. Cancer Res.* (2000) 4343-4350, 6(11).
Bianco et al., "Loss of PTEN/MMAC1/TEP in EGF receptor-expressing tumor cells counteracts the antitumor action of EGFR tyrosine kinase inhibitors." *Oncogene* (2003) 2812-2822, 22(18).

Bier et al., "Clinical trial with escalating doses of the antiepidermal growth factor receptor humanized monoclonal antibody EMD 72 000 in patients with advanced squamous cell carcinoma of the larynx and hypopharynx." *Cancer chemotherapy and pharmacology* (2001) 519-524, 47(6).
Bier et al., "Anti-(epidermal growth factor) receptor monoclonal antibodies for the induction of antibody-dependent cell-mediated cytotoxicity against squamous cell carcinoma lines of the head and neck." *Cancer Immunol. Immunother.* (1998) 167-173, 46(3).
Bier et al., "Dose-dependent access of murine anti-epidermal growth factor receptor monoclonal antibody to tumor cells in patients with advanced laryngeal and hypopharyngeal carcinoma." *European archives of oto-rhino-laryngology : official journal of the European Federation of Oto-Rhino-Laryngological Societies (EUFOS) : affiliated with the German Society for Oto-Rhino-Laryngology—Head and Neck Surgery* (1995) 433-439, 252(7).
Biernat et al., "Predominant expression of mutant EGFR (EGFRvIII) is rare in primary glioblastomas." *Brain Pathology* (Zurich, Switzerland) (2004) 131-136, 14(2).
Bigner et al., "Characterization of the epidermal growth factor receptor in human glioma cell lines and xenografts." *Cancer Res.* (1990) 8017-8022, 50(24).
Bindon et al., "Importance of antigen specificity for complement-mediated lysis by monoclonal antibodies." *European Journal of Immunology* (1988) 1507-1514, 18(10).
Biscardi et al., "c-Src, receptor tyrosine kinases, and human cancer." *Advances in Cancer Research* (1999) 61-119, 76.
Bishop, "The molecular genetics of cancer." *Science* (1987) 305-311, 235(4786).
Bishop et al., "Differential sensitivity of cancer cells to inhibitors of the epidermal growth factor receptor family." *Oncogene* (2002) 119-127, 21(1).
Blagosklonny et al., "Why Iressa failed: toward novel use of kinase inhibitors (outlook)." *Cancer Biology & Therapy* (2003) 137-140, 2(2).
Bleeker et al., "Dual mode of action of a human anti-epidermal growth factor receptor monoclonal antibody for cancer therapy." *Journal of immunology* (Baltimore, Md : 1950) (2004) 4699-4707, 173(7).
Blume-Jensen et al., "Oncogenic kinase signalling." *Nature* (2001) 355-365, 411(6835).
Boder et al., "Phage Display and Its Applications" *Methods Enzymol.*, Chapter 25: "Yeast surface display for directed evolution of protein expression, affinity and sability", (2000) 430-444, 328.
Boder et al., "Directed evolution of antibody fragments with monovalent femtomolar antigen-binding affinity." *Proceedings of the National Academy of Sciences of the United States of America* (2000) 10701-10705, 97(20).
Boder et al., "Yeast surface display for screening combinatorial polypeptide libraries." *Nat. Biotechnol.* (1997) 553-557, 15(6).
Bogan et al., "Anatomy of hot spots in protein interfaces." *J. Mol. Biol.* (1998) 1-9, 280(1).
Boger, "Design, synthesis, and evaluation of DNA minor groove binding agents: the duocarmycins" *Pure & Appl. Chem.* (1994) 837-844, 66(4).
Boghaert et al., "Antibody-targeted chemotherapy with the calicheamicin conjugate hu3S193-N-acetyl gamma calicheamicin dimethyl hydrazide targets Lewisy and eliminates Lewisy-positive human carcinoma cells and xenografts." *Clin. Cancer Res.* (2004) 4538-4549, 10(13).
Bonner et al., "Cetuximab improves locoregional control and survival of locoregionally advanced head and neck cancer: independent review of mature data with a median follow-up of 45 months" *Presented at the Annual AACR-NCI-EORTC International Conference on Molecular Targets and Cancer Therapeutics: Discovery, Biology, and Clinical Applications*; Nov. 14-18, 2005. Philadelphia, Pa. (2011) Abstract B106.
Bonner et al., "Cetuximab prolongs survival in patients with locoregionally advanced squamous cell carcinoma of head and neck (A phase III study of high dose radiation therapy with or without cetuximab)" *Journal of Clinical Oncology*, 2004 ASCO Annual Meeting Proceedings (Post-Meeting Edition) (2004) Abstract 5507, 22(14S; Jul. 15 Supplement).

(56) References Cited

OTHER PUBLICATIONS

Bonner et al., "Continued response following treatment with IMC-C225, an EGFr MoAb combined with RD in advanced head and neck malignancies." *Proceedings of the Annual Meeting of the American Society of Clinical Oncology* (2000) 4a (Abstract 5F), 10.
Bonner et al., "Enhanced apoptosis with combination C225/radiation treatment serves as the impetus for clinical investigation in head and neck cancers." *J. Clin. Oncol.* (2000) 47S-53S, 18(21; Supplement).
Bonner et al., "Radiotherapy plus cetuximab for squamous-cell carcinoma of the head and neck." *N. Engl. J. Med.* (2006) 567-578, 354(6).
De Bono et al., "The ErbB receptor family: a therapeutic target for cancer." *Trends in molecular medicine* (2002) S19-26, 8(4; Supplement).
Boonstra et al., "The epidermal growth factor." *Cell biology international* (1995) 413-430, 19(5).
Bos et al., "Phase I studies of anti-epidermal growth factor receptor chimeric monoclonal antibody C225 in patients with EGFR overexpressing tumors" *American Society of Clinical Oncology* (1966) 443 (Abstract 1381), 15.
Bos et al., "PD153035, a tyrosine kinase inhibitor, prevents epidermal growth factor receptor activation and inhibits growth of cancer cells in a receptor number-dependent manner." *Clin. Cancer Res.* (1997) 2099-2106, 3(11).
Boschelli, "Small molecule inhibitors of receptor tyrosine kinases" *Drugs of thr Future* (1999) 515-537, 24(5).
Bouyain et al., "The extracellular region of ErbB4 adopts a tethered conformation in the absence of ligand." *Proceedings of the National Academy of Sciences of the United States of America* (2005) 15024-15029, 102(42).
Boyer et al., "Relative cytotoxic activity of immunotoxins reactive with different epitopes on the extracellular domain of the c-erbB-2 (HER-2/neu) gene product p185." *Int. J. Cancer* (1999) 525-531, 82(4).
Brady et al., "Malignant astrocytomas treated with iodine-125 labeled monoclonal antibody 425 against epidermal growth factor receptor: a phase II trial." *Int. J. Radiat. Oncol. Biol. Phys.* (1992) 225-230, 22(1).
Brock et al., "Current perspectives in gliomas." *Medical oncology* (Northwood, London, England) (1997) 103-120, 14(2).
Brown et al., "Antibodies vol. 1: A practical approach" *Murine Monoclonal Antibodies. Antibodies vol. 1. A Practical Approach*. D. Catty. Oxford England, IRL Press (1988) 81-104.
Brown et al., "Antiepidermal growth factor receptor antibodies augment cytotoxicity of chemotherapeutic agents on squamous cell carcinoma cell lines." *Otolaryngology—Head and Neck Surgery : Official Journal of American Academy of Otolaryngology—Head and Neck Surgery* (2000) 75-83, 122(1).
Brüggemann et al., "The immunogenicity of chimeric antibodies." *The Journal of Experimental Medicine* (1989) 2153-2157, 170(6).
Bruns et al., "Blockade of the epidermal growth factor receptor signaling by a novel tyrosine kinase inhibitor leads to apoptosis of endothelial cells and therapy of human pancreatic carcinoma." *Cancer Res.* (2000) 2926-2935, 60(11).
Bruns et al., "Epidermal growth factor receptor blockade with C225 plus gemcitabine results in regression of human pancreatic carcinoma growing orthotopically in nude mice by antiangiogenic mechanisms." *Clin. Cancer Res.* (2000) 1936-1948, 6(5).
Bucci et al., "EGF-R expression in ductal breast cancer: proliferation and prognostic implications." *Anticancer research* (1997) 769-774, 17(1B).
Bucholtz, "Radiolabeled antibody therapy." *Seminars in oncology nursing* (1987) 67-73, 3(1).
Buchsbaum et al., "Experimental radioimmunotherpy." *Medical physics* (1993) 551-567, 20(2; Part 2).
Budillon et al., "ZD1839, An Epidermal Growth Factor Receptor Tyrosine Kinase Inhibitor, Upgregulates P27KIP1 Inducing G1 Arrest and Enhancing the Antitumor Effect of Interferon" *Proceedings of the Annual Meeting of the American Association for Cancer Research* (2000) 773 (Abstract 4910), 41.
Burgess et al., "Murine epidermal growth factor: heterogeneity on high resolution ion-exchange chromatography." *EMBO J.* (1983) 2065-2069, 2(11).
Burgess, "EGFR family: structure physiology signalling and therapeutic targets." *Growth Factors* (2008) 263-274, 26(5).
Burgess et al., "An open-and-shut case? Recent insights into the activation of EGF/ErbB receptors." *Mol. Cell* (2003) 541-552, 12(3).
Burris et al., "Phase I safety, pharmacokinetics, and clinical activity study of lapatinib (GW572016), a reversible dual inhibitor of epidermal growth factor receptor tyrosine kinases, in heavily pretreated patients with metastatic carcinomas." *J. Clin. Oncol.* (2005) 5305-5313, 23(23).
Burstein et al., "A phase II, open-label, multicenter study of lapatinib in two cohorts of patients with advanced or metastatic breast cancer who have progressed while receiving Trastuzumab-containing regimens." *Annals of Oncology* (2004) 27 (Abstract 1040), 15(Suppl. 3).
Burstein et al., "Trastuzumab and vinorelbine as first-line therapy for HER2-overexpressing metastatic breast cancer: multicenter phase II trial with clinical outcomes, analysis of serum tumor markers as predictive factors, and cardiac surveillance algorithm." *J. Clin. Oncol.* (2003) 2889-2895, 21(15).
Burtness et al., "Phase III trial comparing cisplatin (C) + placebo to C + anti-epidermal growth factor antibody (EGF-R) C225 in patients (pts) with metastatic/recurrent head & neck cancer (HNC) (Abstract 901)" *Proceedings of the American Society of Clinical Oncology* (2002) 226a, 21.
Burtness et al., "Phase III randomized trial of cisplatin plus placebo compared with cisplatin plus cetuximab in metastatic/recurrent head and neck cancer: an Eastern Cooperative Oncology Group study." *J. Clin. Oncol.* (2005) 8646-8654, 23(34).
Busam et al., "Cutaneous side-effects in cancer patients treated with the antiepidermal growth factor receptor antibody C225." *The British journal of dermatology* (2001) 1169-1176, 144(6).
Buss et al., "Altered epidermal growth factor (EGF)-stimulated protein kinase activity in variant A431 cells with altered growth responses ro EGF." *Proceedings of the National Academy of Sciences of the United States of America* (1982) 2574-2578, 79(8).
Cadena et al., "Receptor protein tyrosine kinases." *In: Protein Phosphorylation* (Chapter 9) (Editor: Marks; Publisher: VCH Publishers, Inc., New York, NY). (1996) 265-284.
Cadena et al., "The intracellular tyrosine kinase domain of the epidermal growth factor receptor undergoes a conformational change upon autophosphorylation." *JBC* (1994) 260-265, 269(1).
Cai et al., "Quantitative PET of EGFR expression in xenograft-bearing mice using 64Cu-labeled cetuximab, a chimeric anti-EGFR monoclonal antibody." *European Journal of Nuclear Medicine and Molecular Imaging* (2007) 850-858, 34(6).
Caldas et al., "Humanization of the anti-CD18 antibody 6.7: an unexpected effect of a framework residue in binding to antigen." *Mol. Immunol.* (2003) 941-952, 39(15).
Callaghan et al., "A complete description of the EGF-receptor exon structure: implication in oncogenic activation and domain evolution." *Oncogene* (1993) 2939-2948, 8(11).
Campos-González et al., "Immunodetection of the ligand-activated receptor for epidermal growth factor." *Growth Factors* (1991) 305-316, 4(4).
Cappuzzo et al., "Increased HER2 gene copy number is associated with response to gefitinib therapy in epidermal growth factor receptor-positive non-small-cell lung cancer patients." *J. Clin. Oncol.* (2005) 5007-5018, 23(22).
Cappuzzo et al., "Epidermal growth factor receptor gene and protein and gefitinib sensitivity in non-small-cell lung cancer." *J. Natl. Cancer Inst.* (2005) 643-655, 97(9).
Carlin et al., "S6 is the human receptor for epidermal growth factor (EGF)" *Cell Genet* (1982) 256, 32.
Carlin et al., "Identity of human epidermal growth factor (EGF) receptor with glycoprotein SA-7: evidence for differential phosphorylation of the two components of the EGF receptor from A431 cells." *Proceedings of the National Academy of Sciences of the United States of America* (1982) 5026-5030, 79(16).
Carpenter, "Receptors for epidermal growth factor and other polypeptide mitogens." *Annual review of Biochemistry* (1987) 881-914, 56.

(56) References Cited

OTHER PUBLICATIONS

Carpenter, "Properties of the receptor for epidermal growth factor." *Cell* (1984) 357-358, 37(2).
Carteni et al., "Panitumumab a novel drug in cancer treatment." *Ann Oncol.* (2007) vi16-21, 18 Suppl 6.
Carter, "Identification and validation of cell surface antigens for antibody targeting in oncology" *Endocrine-Related Cancer* (2004) 659-687, 11(4).
Carter, "Improving the efficacy of antibody-based cancer therapies." *Nature Rev. Cancer* (2001) 118-129, 1(2).
Carter et al., "Humanization of an anti-p185HER2 antibody for human cancer therapy." *Proceedings of the National Academy of Sciences of the United States of America* (1992) 4285-4289, 89(10).
Carter et al., "Tissue-specific transformation by oncogenic mutants of epidermal growth factor receptor." *Critical reviews in oncogenesis* (1994) 389-428, 5(4).
Cartron et al., "Therapeutic activity of humanized anti-CD20 monoclonal antibody and polymorphism in IgG Fc receptor FcγRIIIa gene." *Blood* (2002) 754-758, 99(3).
Casado et al., "A phase I/IIA pharmacokinetic (PK) and serial skin and tumor pharmacodynamic (PD) study of the EGFR irreversible tyrosine kinase inhibitor EKB-569 in combination with 5-fluorouracil (5FU), leucovorin (LV) and irinotecan (CPT-11) (FOLFIRI regimen) in patients (pts) with advanced colorectal cancer (ACC)." *Journal of Clinical Oncology* (2004) 255s (Abstract 3543), 22.
Casset et al., "A peptide mimetic of an anti-CD4 monoclonal antibody by rational design." *Biochem. Biophys. Res. Commun.* (2003) 198-205, 307(1).
Catimel et al., "Purification and characterization of a novel restricted antigen expressed by normal and transformed human colonic epithelium." *JBC* (1996) 25664-25670, 271(41).
Chaffanet et al., "EGF receptor amplification and expression in human brain tumours." *Eur. J. Cancer* (1992) 11-17, 28(1).
Chakravarti et al., "Insulin-like growth factor receptor I mediates resistance to anti-epidermal growth factor receptor therapy in primary human glioblastoma cells through continued activation of phosphoinositide 3-kinase signaling." *Cancer Res.* (2002) 200-207, 62(1).
Chan et al., "EGFR Tyrosine Kinase Inhibition Decreases Epithelial Proliferation in DCIS of the Breast, Whereas C-ERBB2 Blockade Does Not" *Proceedings of the Annual Meeting of the American Association for Cancer Research* (2000) 482 (Abstract 3074), 41.
Chang et al., "Ligand-induced internalization of the epidermal growth factor receptor is mediated by multiple endocytic codes analogous to the tyrosine motif found in constitutively internalized receptors." *JBC* (1993) 19312-19320, 268(26).
Chantry, "The kinase domain and membrane localization determine intracellular interactions between epidermal growth factor receptors." *JBC* (1995) 3068-3073, 270(7).
Chao, "Characterizing and engineering antibodies against the epidermal growth factor receptor (PhD Thesis)" *Submission to the Department of Chemical Engineering in partial fulfillment of the requirements for the degree of Doctor of Philosophy in Chemical Engineering at the Massachusetts Institute of Technology* (2008) 53, 54 and 78.
Chao et al., "Fine epitope mapping of anti-epidermal growth factor receptor antibodies through random mutagenesis and yeast surface display." *J. Mol. Biol.* (2004) 539-550, 342(2).
Chau et al., "The association between EGFR variant III, HPV, p16, c-MET, EGFR gene copy number and response to EGFR inhibitors in patients with recurrent or metastatic squamous cell carcinoma of the head and neck." *Head & neck oncology* (2011) 11, 3.
Chen et al., "Mice mutant for EGFR and Shp2 have defective cardiac semilunar valvulogenesis." *Nature Genetics* (2000) 296-299, 24(3).
Cherk et al., "Lack of correlation of hypoxic cell fraction and angiogenesis with glucose metabolic rate in non-small cell lung cancer assessed by 18F-Fluoromisonidazole and 18F-FDG PET." *J. Nucl. Med.* (2006) 1921-1926, 47(12).
Chien et al., "Significant structural and functional change of an antigen-binding site by a distant amino acid substitution: proposal of a structural mechanism." *Proceedings of the National Academy of Sciences of the United States of America* (1989) 5532-5536, 86(14).
Ching et al., "Expression of mRNA for epidermal growth factor, transforming growth factor-alpha and their receptor in human prostate tissue and cell lines." *Molecular and cellular biochemistry* (1993) 151-158, 126(2).
Chinkers et al., "Rapid induction of morphological changes in human carcinoma cells A-431 by epidermal growth factors." *The Journal of Cell Biology* (1979) 260-265, 83(1).
Cho et al., "Structure of the extracellular region of HER2 alone and in complex with the Herceptin Fab." *Nature* (2003) 756-760, 421(6924).
Cho et al., "Structure of the extracellular region of HER3 reveals an interdomain tether." *Science* (2002) 1330-1333, 297(5585).
Chong et al., "Phase I trial of 131I-huA33 in patients with advanced colorectal carcinoma." *Clin. Cancer Res.* (2005) 4818-4826, 11(13).
Chopra, "111In-Labeled CHX-A"-DTPA conjugated monoclonal antibody (mAb) 806 targeting the epidermal growth factor receptor deletion variant de2-7 (EGFRvIII)." *Molecular Imaging and Contrast Agent Database (MICAD)* [Internet]. Bethesda(MD): National Center for Biotechnology Information (US) (2010) 1-5.
Chopra, "125I-Labeled monoclonal antibody (mAb) 806 targeting the epidermal growth factor receptor deletion variant de2-7 (EGFRvIII)." *Molecular Imaging and Contrast Agent Database (MICAD)* [Internet]. Bethesda(MD): National Center for Biotechnology Information (US) (2010) 1-4.
Chopra, "111In-Labeled chimeric monoclonal antibody, ch806, targeting the epidermal growth factor receptor deletion variant de2-7 (EGFRvIII)." *Molecular Imaging and Contrast Agent Database (MICAD)* [Internet]. Bethesda(MD): National Center for Biotechnology Information (US) (2010) 1-5.
Chopra, "124I-Labeled residulizing ligand IMP-R4 conjugated chimeric monoclonal antibody ch806 targeting the epidermal growth factor receptor deletion variant de2-7(EGFRvIII)." *Molecular Imaging and Contrast Agent Database (MICAD)* [Internet]. Bethesda(MD): National Center for Biotechnology Information (US) (2010) 1-5.
Christensen et al., "High levels of HER-2 expression alter the ability of epidermal growth factor receptor (EGFR) family tyrosine kinase inhibitors to inhibit EGFR phosphorylation in vivo." *Clin. Cancer Res.* (2001) 4230-4238, 7(12).
Christensen et al., "Immunohistochemical detection of epidermal growth factor receptor in laryngeal squamous cell carcinomas." *Acta Otolaryngologica* (1992) 734-738, 112(4).
Christmann et al., "Epitope mapping and affinity purification of monospecific antibodies by *Escherichia coli* cell surface display of gene-derived random peptide libraries." *J. Immunol. Methods* (2001) 163-173, 257(1-2).
Chu et al., "Receptor dimerization is not a factor in the signalling activity of a transforming variant epidermal growth factor receptor (EGFRvIII)." *Biochem. J.* (1997) 855-861, 324 ( Pt 3).
Chung et al., "Increased epidermal growth factor receptor gene copy number is associated with poor prognosis in head and neck squamous cell carcinomas." *Journal of Clinical Oncology* (2006) 4170-4176, 24(25).
Chung et al., "Cetuximab shows activity in colorectal cancer patients with tumors that do not exprress the epidermal growth factor receptor by immunohistochemistry." *J. Clin. Oncol.* (2005) 1803-1810, 23(9).
Ciardiello et al., "Potentiation of cytotoxic drugs activity in human cancer cells by ZD-1839 (IRESSA), and EGFR-selective tyrosine kinase inhibitor." *Proceedings of the American Association for Cancer Research* (2000) 482 (Abstract 3075), 41.
Ciardiello et al., "Epidermal growth factor receptor (EGFR) as a target in cancer therapy: understanding the role of receptor expression and other molecular determinants that could influence the response to anti-EGFR drugs." *Eur. J. Cancer* (2003) 1348-1354, 39(10).
Ciardiello et al., "A novel approach in the treatment of cancer: targeting the epidermal growth factor receptor." *Clin. Cancer Res.* (2001) 2958-2970, 7(10).

(56) References Cited

OTHER PUBLICATIONS

Ciardiello et al., "Inhibition of growth factor production and angiogenesis in human cancer cells by ZD1839 (Iressa), a selective epidermal growth factor receptor tyrosine kinase inhibitor." *Clin. Cancer Res.* (2001) 1459-1465, 7(5).
Ciardiello et al., "Antiangiogenic and antitumor activity of anti-epidermal growth factor receptor C225 monoclonal antibody in combination with vascular endothelial growth factor antisense oligonucleotide in human GEO colon cancer cells." *Clin. Cancer Res.* (2000) 3739-3747, 6(9).
Ciardiello et al., "Antitumor effect and potentiation of cytotoxic drugs activity in human cancer cells by ZD-1839 (Iressa), an epidermal growth factor receptor-selective tyrosine kinase inhibitor." *Clin. Cancer Res.* (2000) 2053-2063, 6(5).
Ciardiello, "Epidermal growth factor receptor tyrosine kinase inhibitors as anticancer agents." *Drugs* (2000) 25-32; discussion 41-2, 60(Suppl. 1).
Ciardiello et al., "Antitumor activity of sequential treatment with topotecan and anti-epidermal growth factor receptor monoclonal antibody C225." *Clin. Cancer Res.* (1999) 909-916, 5(4).
Ciardiello et al., "Cooperative inhibition of renal cancer growth by anti-epidermal growth factor receptor antibody and protein kinase A antisense oligonucleotide." *J. Natl. Cancer Inst.* (1998) 1087-1094, 90(14).
Ciardiello et al., "Antitumor activity of combined blockade of epidermal growth factor receptor and protein kinase A." *J. Natl. Cancer Inst.* (1996) 1770-1776, 88(23).
Ciardiello et al., "Cooperative antiproliferative effects of 8-chloro-cyclic AMP and 528 anti-epidermal growth factor receptor monoclonal antibody on human cancer cells." *Clin. Cancer Res.* (1995) 161-167, 1(2).
Ciesielski et al., "Oncogenic epidermal growth factor receptor mutants with tandem duplication: gene structure and effects on receptor function." *Oncogene* (2000) 810-820, 19(6).
Clark, "Antibody humanization: a case of the 'Emperor's new clothes'?" *Immunology today* (2000) 397-402, 21(8).
Clarke et al., "Therapeutic efficacy of anti-Lewis (y) humanized 3S 193 radioimmunotherapy in a breast cancer model: enhanced activity when combined with Taxol chemotherapy" *Clin. Cancer Res.* (2000) 3621-3628, 6.
Clarke et al., "Mutant epidermal growth factor receptor enhances induction of vascular endothelial growth factor by hypoxia and insulin-like growth factor-1 via a PI3 kinase dependent pathway." *British Journal of Cancer* (2001) 1322-1329, 84(10).
Clarke et al., "In vivo biodistribution of a humanized anti-Lewis Y monoclonal antibody (hu3S193) in MCF-7 xenografted BALB/c nude mice." *Cancer Res.* (2000) 4804-4811, 60(17).
Clayton et al., "Unligated epidermal growth factor receptor forms higher order oligomers within microclusters on A431 cells that are sensitive to tyrosine kinase inhibitor binding." *Biochemistry* (2007) 4589-4597, 46(15).
Clayton et al., "Ligand-induced dimer-tetramer transition during the activation of the cell surface epidermal growth factor receptor—A multidimensional microscopy analysis." *JBC* (2005) 30392-30399, 280(34).
Clynes et al., "Inhibitory Fc receptors modulate in vivo cytotoxicity against tumor targets." *Nature Med.* (2000) 443-446, 6(4).
Co et al., "Humanized antibodies for therapy." *Nature* (1991) 501-502, 351(6326).
Cobleigh et al., "Multinational study of the efficacy and safety of humanized anti-HER2 monoclonal antibody in women who have HER2-overexpressing metastatic breast cancer that has progressed after chemotherapy for metastatic disease." *J. Clin. Oncol.* (1999) 2639-2648, 17(9).
Cochran et al., "Domain-level antibody epitope mapping through yeast surface display of epidermal growth factor receptor fragments." *J. Immunol. Methods* (2004) 147-158, 287(1-2).

Cohen et al., "Phase II study of ZD1839 (Iressa) in recurrent or metastatic squamous cell carcinoma of the head and neck (SCCHN)." *Proceedings of the American Society of Clinical Oncology* (2002) 225a (Abstract 899), 21.
Cohen et al., "Safety profile of the monoclonal antibody (MoAb) IMC-C255, an anti-epidermal growth factor receptor (EGFR) used in the treatment of EGFR-positive tumors." *Proceedings of the American Society of Clinical Oncology* (2000) 474a (Abstract 1862), 19.
Cohen et al., "United States Food and Drug Administration Drug Approval summary: Gefitinib (ZD1839; Iressa) tablets." *Clin. Cancer Res.* (2004) 1212-1218, 10(4).
Cohen et al., "Epidermal growth factor-receptor-protein kinase interactions. Co-purification of receptor and epidermal growth factor-enhanced phosphorylation activity." *Journal of Biological Chemistry* (1980) 4834-4842, 255(10).
Cokgor et al., "Phase I trial results of iodine-131-labeled antitenascin monoclonal antibody 81C6 treatment of patients with newly diagnosed malignant gliomas." *J. Clin. Oncol.* (2000) 3862-3872, 18(22).
Colapinto et al., "Comparative localization of murine monoclonal antibody Mel-14 F(ab')2 fragment and whole IgG2a in human glioma xenografts." *Cancer Res.* (1988) 5701-5707, 48(20).
Collins, "Gene amplification in human gliomas." *Glia* (1995) 289-296, 15(3).
Collins, "Amplified genes in human gliomas." *Seminars in cancer biology* (1993) 27-32, 4(1).
Cortez et al., "Influence of size, surface, cell line, and kinetic properties on the specific binding of A33 antigen-targeted multilayered particles and capsules to colorectal cancer cells." *ACS nano* (2007) 93-102, 1(2).
Cortez et al., "Targeting and Uptake of Multilayered Particles to Colorectal Cancer Cells" *Advanced Materials* (2006) 1998-2003, 18.
Corti et al., "Idiotope determining regions of a mouse monoclonal antibody and its humanized versions. Identification of framework residues that affect idiotype expression." *J. Mol. Biol.* (1994) 53-60, 235(1).
Cowley et al., "Increased EGF receptors on human squamous carcinoma cell lines." *British Journal of Cancer* (1986) 223-229, 53(2).
Cragg et al., "Signaling antibodies in cancer therapy." *Curr. Opin. Immunol.* (1999) 541-547, 11(5).
Crawford et al., "ABX-EGF in combination with paclitaxel and carboplatin for advanced non-small cell lung cancer (NSCLC)" *Journal of Clinical Oncology*, 2004 ASCO Annual Meeting Proceedings (Post-Meeting Edition) (2004) 7083, 22(14S).
Crombet et al., "Use of the anti-EGFR antibody h-R3 in combination with radiotherapy in the treatment of advanced head and neck cancer (Abstract 53)" *Proceedings of the American Society of Clinical Oncology* (2002) 14a, 21.
Crombet et al., "Phase I clinical evaluation of a neutralizing monoclonal antibody against epidermal growth factor receptor in advanced brain tumor patients: preliminary study." *Hybridoma* (2001) 131-136, 20(2).
Crombet et al., "Use of the humanized anti-epidermal growth factor receptor monoclonal antibody h-R3 in combination with radiotherapy in the treatment of locally advanced head and neck cancer patients." *J. Clin. Oncol.* (2004) 1646-1654, 22(9).
Cunningham et al., "High-resolution epitope mapping of hGH-receptor interactions by alanine-scanning mutagenesis." *Science* (1989) 1081-1085, 244(4908).
Cunningham et al., "Cetuximab monotherapy and cetuximab plus irinotecan in irinotecan-refractory metastatic colorectal cancer." *N. Engl. J. Med.* (2004) 337-345, 351(4).
Cvrljevic et al., "Activation of Src induces mitochondrial localisation of de2-7EGFR (EGFRvIII) in glioma cells: implications for glucose metabolism." *Journal of cell science* (2011) 2938-2950, 124(Part 17).
Dadparvar et al., "Indium-111-labeled anti-EGFr-425 scintigraphy in the detection of malignant gliomas." *Cancer* (1994) 884-889, 73(3; Supplement).
Daley et al., "Transformation of an interleukin 3-dependent hematopoietic cell line by the chronic myelogenous leukemia-specific P210bcr/abl protein." *Proceedings of the National Academy of Sciences of the United States of America* (1988) 9312-9316, 85(23).

(56) References Cited

OTHER PUBLICATIONS

Damjanov et al., "Immunohistochemical localization of the epidermal growth factor receptor in normal human tissues." *Laboratory investigation; a journal of technical methods and pathology* (1986) 588-592, 55(5).
Damle, "Antibody-drug conjugates ace the tolerability test." *Nat. Biotechnol.* (2008) 884-885, 26(8).
Damstrup et al., "In vitro invasion of small-cell lung cancer cell lines correlates with expression of epidermal growth factor receptor." *British Journal of Cancer* (1998) 631-640, 78(5).
Damstrup et al., "Epidermal growth factor receptor mutation type III transfected into a small cell lung cancer cell line is predominantly localized at the cell surface and enhances the malignant phenotype." *Int. J. Cancer* (2002) 7-14, 97(1).
Daugherty et al., "Polymerase chain reaction facilitates the cloning, CDR-grafting, and rapid expression of a murine monoclonal antibody directed against the CD18 component of leukocyte integrins." *Nucleic acids research* (1991) 2471-2476, 19(9).
Davies et al., "Affinity improvement of single antibody VH domains: residues in all three hypervariable regions affect antigen binding." *Immunotechnology : an international journal of immunological engineering* (1996) 169-179, 2(3).
Davies et al., "Genetic analysis of epidermal growth factor action: assignment of human epidermal growth factor receptor gene to chromosome 7." *Proceedings of the National Academy of Sciences of the United States of America* (1980) 4188-4192, 77(7).
Davies et al., "Specificity and mechanism of action of some commonly used protein kinase inhibitors." *Biochem. J.* (2000) 95-105, 351(Part 1).
Davis et al., "Transgenic mice as a source of fully human antibodies for the treatment of cancer." *Cancer Metastasis Rev.* (1999) 421-425, 18(4).
Dawson et al., "A phase II trial of gefitinib (Iressa, ZD1839) in stage IV and recurrent renal cell carcinoma." *Clin. Cancer Res.* (2004) 7812-7819, 10(23).
Dazzi et al., "Expression of epidermal growth factor receptor (EGF-R) in non-small cell lung cancer. Use of archival tissue and correlation of EGF-R with histology, tumour size, node status and survival." *British Journal of Cancer* (1989) 746-749, 59(5).
Dechant et al., "Effect of combinations of EGF-R antibodies on complement-dependent tumor cell lysis" *Journal of Clinical Oncolocy* (2008) 14005, 26(15S).
Decker, "Transmembrane signaling by epidermal growth factor receptors lacking autophosphorylation sites." *Journal of Biological Chemistry* (1993) 9176-9179, 268(13).
Decker, "Aspects of the metabolism of the epidermal growth factor receptor in A431 human epidermoid carcinoma cells." *Mol. Cell Biol.* (1984) 571-575, 4(4).
Deen et al., "Brain Tumor Working Group Report on the 9th International Conference on Brain Tumor Research and Therapy. Organ System Program, National Cancer Institute." *Journal of neuro-oncology* (1993) 243-272, 16(3).
Dehm et al., "SRC gene expression in human cancer: the role of transcriptional activation." *Biochemistry and cell biology* (2004) 263-274, 82(2).
Denardo et al., "Strategies for developing effective radioimmunotherapy for solid tumors." *Clin. Cancer Res.* (1999) 3219s-3223s, 5(10; Supplement).
Denardo et al., "A new era for radiolabeled antibodies in cancer?" *Curr. Opin. Immunol.* (1999) 563-569, 11(5).
Dewitt et al., "Quantitative analysis of the EGF receptor autocrine system reveals cryptic regulation of cell response by ligand capture." *Journal of cell science* (2001) 2301-2313, 114(Part 12).
Dicosimo et al., "Schedule-dependent effects of the epidermal growth factor receptor (EGFR) tyrosine kinase inhibitor gefitinib in combination with the mammalian target of rapamycin (mTOR) inhibitor everolimus (RAD001)." *Proceedings of the American Society of Clinical Oncology* (2004) 213s (Abstract 3074).

Diedrich et al., "Distribution of epidermal growth factor receptor gene amplification in brain tumours and correlation to prognosis." *Journal of Neurology* (1995) 683-688, 242(10).
Van Dijk et al., "Human antibodies as next generation therapeutics." *Current opinion in chemical biology* (2001) 368-374, 5(4).
Discafani et al., "Irreversible inhibition of epidermal growth factor receptor tyrosine kinase with in vivo activity by N-[4-[(3-bromophenyl)amino]-6-quinazolinyl]-2-butynamide (CL-387,785)." *Biochemical pharmacology* (1999) 917-925, 57(8).
Dittadi et al., "Epidermal growth factor receptor in lung malignancies. Comparison between cancer and normal tissue." *British Journal of Cancer* (1991) 741-744, 64(4).
Divgi et al., "Phase I and imaging trial of indium 111-labeled anti-epidermal growth factor receptor monoclonal antibody 225 in patients with squamous cell lung carcinoma." *J. Natl. Cancer Inst.* (1991) 97-104, 83(2).
Domagala et al., "Stoichiometry, kinetic and binding analysis of the interaction between epidermal growth factor (EGF) and the extracellular domain of the EGF receptor." *Growth Factors* (2000) 11-29, 18(1).
Van Doorn et al., "Follicular and epidermal alterations in patients treated with ZD1839 (Iressa), an inhibitor of the epidermal growth factor receptor." *The British journal of dermatology* (2002) 598-601, 147(3).
Doronina et al., "Enhanced Activity of Monomethylauristatin F through Monoclonal Antibody Delivery: Effects of Linker Technology on Efficacy and Toxicity" *Bioconjugate chemistry* (2006) 114-124, 17(1).
Downward et al., "Close similarity of epidermal growth factor receptor and v-erb-B oncogene protein sequences." *Nature* (1984) 521-527, 307(5951).
Eberhard et al., "Mutations in the epidermal growth factor receptor and in KRAS are predictive and prognostic indicators in patients with non-small-cell lung cancer treated with chemotherapy alone and in combination with erlotinib." *J. Clin. Oncol.* (2005) 5900-5909, 23(25).
Egloff et al., "Targeting epidermal growth factor receptor and SRC pathways in head and neck cancer." *Semin. Oncol.* (2008) 286-297, 35(3).
Ekstrand et al., "Altered subcellular location of an activated and tumour-associated epidermal growth factor receptor." *Oncogene* (1995) 1455-1460, 10(7).
Ekstrand et al., "Functional characterization of an EGF receptor with a truncated extracellular domain expressed in glioblastomas with EGFR gene amplification." *Oncogene* (1994) 2313-2320, 9(8).
Ekstrand et al., "Amplified and rearranged epidermal growth factor receptor genes in human glioblastomas reveal deletions of sequences encoding portions of the N- and/or C-terminal tails." *Proceedings of the National Academy of Sciences of the United States of America* (1992) 4309-4313, 89(10).
Ekstrand et al., "Genes for epidermal growth factor receptor, transforming growth factor alpha, and epidermal growth factor and their expression in human gliomas in vivo." *Cancer Res.* (1991) 2164-2172, 51(8).
Elleman et al., "Identification of a determinant of epidermal growth factor receptor ligand-binding specificity using a truncated, high-affinity form of the ectodomain." *Biochemistry* (2001) 8930-8939, 40(30).
Eller et al., "Activity of anti-epidermal growth factor receptor monoclonal antibody C225 against glioblastoma multiforme." *Neurosurgery* (2002) 1005-13; discussion 1013-4, 51(4).
Ellgaard et al., "Quality control in the endoplasmic reticulum." *Nat. Rev. Mol. Cell Biol.* (2003) 181-191, 4(3).
Ellis et al., "Preclinical analysis of the analinoquinazoline AG1478, a specific small molecule inhibitor of EFG receptor tyrosine kinase." *Biochemical pharmacology* (2006) 1422-1434, 71(10).
Emsley et al., "Coot: model-building tools for molecular graphics." *Acta Crystallogr. D. Biol. Crystallogr.* (2004) 2126-2132, 60(Pt 12 Pt 1).
Ennis, "Monoclonal Anti-EGF Receptor Antibodies Inhibit the Growth of Malignant and Nonmalignant Human Mammary Epithelial Cells." *J. Cell Biochem.* (1989) 104 (Abstract E207)(Suppl. 13B).

(56) References Cited

OTHER PUBLICATIONS

Ennis et al., "The EGF receptor system as a target for antitumor therapy." *Cancer investigation* (1991) 553-562, 9(5).
Ennis et al., "Anti-epidermal growth factor receptor antibodies inhibit the autocrine-stimulated growth of MDA-468 human breast cancer cells." *Molecular endocrinology* (Baltimore, Md.) (1989) 1830-1838, 3(11).
Epenetos et al., "Long term survival of patients with advanced ovarian cancer treated with intraperitoneal radioimmunotherapy." *International journal of gynecological cancer : official journal of the International Gynecological Cancer Society* (2000) 44-46, 10(Suppl. 1).
Epenetos et al., "Antibody guided irradiation of brain glioma by arterial infusion of radioactive monoclonal antibody against epidermal growth factor receptor and blood group A antigen." *British medical journal (Clinical research ed.)* (1985) 1463-1466, 290(6480).
Erickson, "Antibody-Maytansinoid Conjugates Are Activated in Targeted Cancer Cells by Lysosomal Degradation and Linker-Dependent Intracellular Processing" *Cancer Research* (2006) 4426-4433, 66(8).
Eriksen et al., "The EGFRvIII variant in squamous cell carcinomas of the head and neck: Expression and correlation with clinico-pathological parameters in 675 patients from the randomised DAHANCA 6/7 study." *ECCO 15—34th ESMO Multidisciplinary Congress* (Berlin) (2009) 472 (Abstract P-8507).
Van Den Eynde et al., "Tumor Antigens" *Tumor Antigens. In : P. J. Delves and I. M. Roitt* (eds.) Encyclopedia of Immunology, Second Edition (London: Academic Press) (1998) 2424-2431.
Ezekiel et al., "Phase I trial of chimerized anti-epidermal growth factor receptor (Anti-EGFr) antibody in combination with either once-daily or twice-daily irradiation for locally advanced head and neck malignancies." *Proceedings of the American Society of Clinical Oncology* (1999) 388a (Abstract 1501), 18.
Faillot et al., "A phase I study of an anti-epidermal growth factor receptor monoclonal antibody for the treatment of malignant gliomas." *Neurosurgery* (1996) 478-483, 39(3).
Fairlie et al., "A fusion protein system for the recombinant production of short disulfide-containing peptides." *Protein Expr. Purif.* (2002) 171-178, 26(1).
Fan et al., "Blockade of epidermal growth factor receptor by anti-EGFR monoclonal antibody 225 causes GI arrest of A431 cells with induction of p27KIPI" *Proceedings of the American Association for Cancer Research* (1996) 10 (Abstract #69), 37.
Fan et al., "Therapeutic application of anti-growth factor receptor antibodies." *Current opinion in oncology* (1998) 67-73, 10(1).
Fan et al., "Antibody-induced epidermal growth factor receptor dimerization mediated inhibition of autocrine proliferation of A431 squamous carcinoma cells." *Journal Biological Chemistry* (1994) 27595-27602, 269(44).
Fan et al., "Antitumor effect of anti-epidermal growth factor receptor monoclonal antibodies plus cis-diamminedichloroplatinum on well established A431 cell xenografts." *Cancer Res.* (1993) 4637-4642, 53(19).
Fan et al., "Blockade of epidermal growth factor receptor function by bivalent and monovalent fragments of 225 anti-epidermal growth factor receptor monoclonal antibodies." *Cancer Res.* (1993) 4322-4328, 53(18).
Fantl et al., "Signalling by receptor tyrosine kinases." *Annual review of biochemistry* (1993) 453-481, 62.
Farrugia et al., "A possible role for metallic ions in the carbohydrate cluster recognition displayed by a Lewis Y specific antibody." *PLoS ONE* (2009) e7777, 4(11).
Feldhaus et al., "Flow-cytometric isolation of human antibodies from a nonimmune *Saccharomyces cerevisiae* surface display library." *Nat. Biotechnol.* (2003) 163-170, 21(2).
Feldkamp et al., "Expression of activated epidermal growth factor receptors, Ras-guanosine triphosphate, and mitogen-activated protein kinase in human glioblastoma multiforme specimens." *Neurosurgery* (1999) 1442-1453, 45(6).

Fendly et al., "Characterization of murine monoclonal antibodies reactive to either the human epidermal growth factor receptor or HER2/neu gene product." *Cancer Res.* (1990) 1550-1558, 50(5).
Fenstermaker et al., "Deletion and tandem duplication of exons 2-7 in the epidermal growth factor receptor gene of a human malignant glioma." *Oncogene* (2000) 4542-4548, 19(39).
Ferguson, "Structure-based view of epidermal growth factor receptor regulation." *Annual review of biophysics* (2008) 353-373, 37.
Ferguson et al., "EGF activates its receptor by removing interactions that autoinhibit ectodomain dimerization." *Mol. Cell* (2003) 507-517, 11(2).
Fernandes et al., "Glycosylation-induced conformational modification positively regulates receptor-receptor association: a study with an aberrant epidermal growth factor receptor (EGFRvIII/DeltaEGFR) expressed in cancer cells." *JBC* (2001) 5375-5383, 276(7).
Ferrara et al., "Discovery and development of bevacizumab, an anti-VEGF antibody for treating cancer." *Nature reviews. Drug discovery* (2004) 391-400, 3(5).
Ferry et al., "Intermittent Oral ZD1839 (Iressa), a Novel Epidermal Growth Factor Receptor Tyrosine Kinase Inhibitor (EGFR-TKI), Show Evidence of Good Tolerability and Activity: Final Results from a Phase I Study (Abstract 5E)" *Proceedings of the American Society of Clinical Oncology* (2000) 3a, 19.
Figlin et al., "ABX-EGF, a fully human anti-epidermal growth factor receptor (EGFR) monoclonal antibody (mAb) in patients with advanced cancer: phase 1 clinical results (Abstract 35)" *Proceedings of the American Society of Clinical Oncology* (2002) 10a, 21.
Filmus et al., "Epidermal growth factor receptor gene-amplified MDA-468 breast cancer cell line and its nonamplified variants." *Mol. Cell Biol.* (1987) 251-257, 7(1).
Filmus et al., "Amplified, overexpressed and rearranged epidermal growth factor receptor gene in a human astrocytoma cell line." *Biochem. Biophys. Res. Commun.* (1985) 207-215, 131(1).
Filmus et al., "MDA-468, a human breast cancer cell line with a high number of epidermal growth factor (EGF) receptors, has an amplified EGF receptor gene and is growth inhibited by EGF." *Biochem. Biophys. Res. Commun.* (1985) 898-905, 128(2).
Finkler et al., "Phase 2 Evaluation of OSI-774, a Potent Oral Antagonist of the EGFR-TK in Patients with Advanced Ovarian Carcinoma." *Proceedings of the American Society of Clinical Oncology* (2001) 208a (Abstract 831), 20.
Di Fiore et al., "Overexpression of the human EGF receptor confers an EGF-dependent transformed phenotype to NIH 3T3 cells." *Cell* (1987) 1063-1070, 51(6).
Fischer-Colbrie et al., "EGFR and steroid receptors in ovarian carcinoma: comparison with prognostic parameters and outcome of patients." *Anticancer research* (1997) 613-619, 17(1B).
Flynn et al., "Campath-1H monoclonal antibody therapy." *Current opinion in oncology* (2000) 574-581, 12(6).
Fong et al., "Epidermal growth factor receptor monoclonal antibody inhibits constitutive receptor phosphorylation, reduces autonomous growth, and sensitizes androgen-independent prostatic carcinoma cells to tumor necrosis factor alpha." *Cancer Res.* (1992) 5887-5892, 52(21).
Foo et al., "Functional imaging of intratumoral hypoxia." *Molecular imaging and biology : MIB : the official publication of the Academy of Molecular Imaging* (2004) 291-305, 6(5).
Forastiere et al., "Head and neck cancer." *N. Engl. J. Med.* (2001) 1890-1900, 345(26).
Ford et al., "Pharmacogenomic approaches for identifying markers predictive of tumor response to Cetuximab (Erbitux)" *Proc. Amer. Assoc. Cancer Res.* (2004) Abstract 2032, 45.
Ford et al., "Targeting epidermal growth factor receptor in head and neck cancer." *Head & neck* (2003) 67-73, 25(1).
Fornier et al., "Trastuzumab in combination with chemotherapy for the treatment of metastatic breast cancer." *Semin. Oncol.* (2000) 38-45; discussion 92-100, 27(6; Suppl. 11).
Foulon et al., "Positively charged templates for labeling internalizing antibodies: comparison of N-succinimidyl 5-iodo-3-pyridinecarboxylate and the D-amino acid peptide KRYRR." *Nucl. Med. Biol.* (2001) 769-777, 28(7).

(56) References Cited

OTHER PUBLICATIONS

Fowler et al., "A mutation in the epidermal growth factor receptor in waved-2 mice has a profound effect on receptor biochemistry that results in impaired lactation." *Proceedings of the National Academy of Sciences of the United States of America* (1995) 1465-1469, 92(5).
Fox et al., "Tumour angiogenesis." *The Journal of pathology* (1996) 232-237, 179(3).
Fraker et al., "Protein and cell membrane iodinations with a sparingly soluble chloroamide, 1,3,4,6-tetrachloro-3a,6a-diphrenylglycoluril." *Biochem. Biophys. Res. Commun.* (1978) 849-857, 80(4).
Frame, "Newest findings on the oldest oncogene; how activated src does it." *Journal of cell science* (2004) 989-998, 117(Part 7).
Francisco, "cAC10-vcMMAE, an anti-CD30-monomethyl auristatin E conjugate with potent and selective antitumor activity" *Blood* (2003) 1458-1465, 102(4).
Frank et al., "SPOT synthesis. Epitope analysis with arrays of synthetic peptides prepared on cellulose membranes." *Methods Mol. Biol.* (1996) 149-169, 66.
Franklin et al., "Association between activation of ErbB pathway genes and survival following gefitinib treatment in advanced BAC (SWOG 0126)." *Proceedings of the Annual Meeting of the American Society of Clinical Oncology* (2004) 620s (Abstract 7015), 22.
Frederick et al., "Analysis of genomic rearrangements associated with EGRFvIII expression suggests involvement of Alu repeat elements." *Neuro-oncology* (2000) 159-163, 2(3).
Frederick et al., "Diversity and frequency of epidermal growth factor receptor mutations in human glioblastomas." *Cancer Res.* (2000) 1383-1387, 60(5).
Friedman et al., "Temozolomide and treatment of malignant glioma." *Clin. Cancer Res.* (2000) 2585-2597, 6(7).
Friedman et al., "Glioblastoma multiforme and the epidermal growth factor receptor." *N. Engl. J. Med.* (2005) 1997-1999, 353(19).
Friedman et al., "Synergistic down-regulation of receptor tyrosine kinases by combinations of mAbs: implications for cancer immunotherapy." *Proceedings of the National Academy of Sciences of the United States of America* (2005) 1915-1920, 102(6).
Friess et al., "Combination treatment with erlotinib and pertuzumab against human tumor xenografts is superior to monotherapy." *Clin. Cancer Res.* (2005) 5300-5309, 11(14).
Fry, "Site-directed irreversible inhibitors of the erbB family of receptor tyrosine kinases as novel chemotherapeutic agents for cancer." *Anti-cancer drug design* (2000) 3-16, 15(1).
Fry, "Inhibition of the epidermal growth factor receptor family of tyrosine kinases as an approach to cancer chemotherapy: progression from reversible to irreversible inhibitors." *Pharmacology & therapeutics* (1999) 207-218, 82(2-3).
Fry et al., "Specific, irreversible inactivation of the epidermal growth factor receptor and erbB2, by a new class of tyrosine kinase inhibitor." *Proceedings of the National Academy of Sciences of the United States of America* (1998) 12022-12027, 95(20).
Fry et al., "Biochemical and antiproliferative properties of 4-[ar(alk)ylamino]pyridopyrimidines, a new chemical class of potent and specific epidermal growth factor receptor tyrosine kinase inhibitor." *Biochemical pharmacology* (1997) 877-887, 54(8).
Fry et al., "A specific inhibitor of the epidermal growth factor receptor tyrosine kinase." *Science* (1994) 1093-1095, 265(5175).
Fujino et al., "A comparison of epidermal growth factor receptor levels and other prognostic parameters in non-small cell lung cancer." *Eur. J. Cancer* (1996) 2070-2074, 32A(12).
Fukai et al., "Antitumor activity of cetuximab against malignant glioma cells overexpressing EGFR deletion mutant variant III." *Cancer science* (2008) 2062-2069, 99(10).
Fukuoka et al., "Final results from a phase II trial of ZD1839 ('Iressa') for patients with advanced non-small cell lung carcinoma (IDEAL 1)." *Proceedings of the American Society of Clinical Oncology* (2002) 298a (Abstract 1188), 21.
Fukuoka et al., "Multi-institutional randomized phase II trial of gefitinib for previously treated patients with advanced non-small-cell lung cancer (The IDEAL 1 Trial) [corrected]." *J. Clin. Oncol.* (2003) 2237-2246, 21(12).

Gadella et al., "Oligomerization of epidermal growth factor receptors on A431 cells studied by time-resolved fluorescence imaging microscopy. A stereochemical model for tyrosine kinase receptor activation." *The Journal of cell biology* (1995) 1543-1558, 129(6).
Gamou et al., "Glycosylation of the epidermal growth factor receptor and its relationship to membrane transport and ligand binding." *Journal of biochemistry* (1988) 388-396, 104(3).
Gan et al., "Targeting a unique EGFR epitope with monoclonal antibody 806 activates NF-kappaB and initiates tumour vascular normalization." *Journal of cellular and molecular medicine* (2009) 3993-4001, 13(9B).
Gan et al., "The EGFRvIII variant in glioblastoma multiforme." *Journal of clinical neuroscience : official iournal of the Neurosurgical Society of Australasia* (2009) 748-754, 16(6).
Gan et al., "The epidermal growth factor receptor (EGFR) tyrosine kinase inhibitor AG1478 increases the formation of inactive untethered EGFR dimers. Implications for combination therapy with monoclonal antibody 806." *JBC* (2007) 2840-2850, 282(5).
Garcia De Palazzo et al., "Expression of mutated epidermal growth factor receptor by non-small cell lung carcinomas." *Cancer Res.* (1993) 3217-3220, 53(14).
Garinchesa et al., "Organ-specific expression of the colon cancer antigen A33, a cell surface target for antibody-based therapy." *Int. J. Oncol.* (1996) 465-471, 9(3).
Garrett et al., "Antibodies specifically targeting a locally misfolded region of tumor associated EGFR." *Proceedings of the National Academy of Sciences of the United States of America* (2009) 5082-5087, 106(13).
Garrett et al., "The crystal structure of a truncated ErbB2 ectodomain reveals an active conformation, poised to interact with other ErbB receptors." *Mol. Cell* (2003) 495-505, 11(2).
Garrett et al., "Crystal structure of a truncated epidermal growth factor receptor extracellular domain bound to transforming growth factor alpha." *Cell* (2002) 763-773, 110(6).
Ge et al., "Evidence of high incidence of EGFRvIII expression and coexpression with EGFR in human invasive breast cancer by laser capture microdissection and immunohistochemical analysis." *Int. J. Cancer* (2002) 357-361, 98(3).
George et al., "Differential effects of anti-beta2-glycoprotein I antibodies on endothelial cells and on the manifestations of experimental antiphospholipid syndrome." (1998) 900-906, 97(9).
Giaccone et al., "Combination therapy with ZD1839 (Iressa), an orally active, selective, epidermal growth factor receptor tyrosine kinase inhibitor (EGFR-TKI), gemcitabine and cisplatin, in patients with advanced solid tumors: promising preliminary results on tolerability, efficacy, and pharmacokinetics." *Clinical Cancer Research* (2001) 3765s (Abstract 553), 7.
Gibson et al., "Randomized phase III trial results of panitumumab, a fully human anti-epidermal growth factor receptor monoclonal antibody, in metastatic colorectal cancer." *Clin. Colorectal Cancer* (2006) 29-31, 6(1).
Gill et al., "Relationship between production of epidermal growth factor receptors, gene amplification, and chromosome 7 translocation in variant A431 cells." *Somatic cell and molecular genetics* (1985) 309-318, 11(4).
Gill et al., "Monoclonal anti-epidermal growth factor receptor antibodies which are inhibitors of epidermal growth factor binding and antagonists of epidermal growth factor binding and antagonists of epidermal growth factor-stimulated tyrosine protein kinase activity." *JBC* (1984) 7755-7760, 259(12).
Gill et al., "New targeted therapies in gastrointestinal cancers." *Current treatment options in oncology* (2003) 393-403, 4(5).
Giusti et al., "Somatic diversification of S107 from an antiphosphocholine to an anti-DNA autoantibody is due to a single base change in its heavy chain variable region." *Proceedings of the National Academy of Sciences of the United States of America* (1987) 2926-2930, 84(9).
Glennie et al., "Clinical trials of antibody therapy." *Immunology today* (2000) 403-410, 21(8).
Glennie et al., "Renaissance of cancer therapeutic antibodies." *Drug discovery today* (2003) 503-510, 8(11).
Goldberg, "Cetuximab." *Nature reviews. Drug discovery* (2005) S10-1(Suppl. 10).

(56) References Cited

OTHER PUBLICATIONS

Goldenberg et al., "Imaging of human tumor xenografts with an indium-111-labeled anti-epidermal growth factor receptor monoclonal antibody." *J. Natl. Cancer Inst.* (1989) 1616-1625, 81(21).

Goldenberg, "Advancing role of radiolabeled antibodies in the therapy of cancer." *Cancer Immunol. Immunother.* (2003) 281-296, 52(5).

Goldenberg, "Targeted therapy of cancer with radiolabeled antibodies." *J. Nucl. Med.* (2002) 693-713, 43(5).

Goldman et al., "Epidermal growth factor stimulates vascular endothelial growth factor production by human malignant glioma cells: a model of glioblastoma multiforme pathophysiology." *Mol. Biol. Cell* (1993) 121-133, 4(1).

Goldman et al., "Heterodimerization of the erbB-1 and erbB-2 receptors in human breast carcinoma cells: a mechanism for receptor transregulation." *Biochemistry* (1990) 11024-11028, 29(50).

Goldstein et al., "Biological efficacy of a chimeric antibody to the epidermal growth factor receptor in a human tumor xenograft model." *Clin. Cancer Res.* (1995) 1311-1318, 1(11).

Gonzalez, "Epidermal growth factor-based cancer vaccine for non-small-cell lung cancer therapy" *Annals of Oncology* (2003) 461-466, 14(3).

Gorgoulis et al., "Molecular and immunohistochemical evaluation of epidermal growth factor receptor and c-erb-B-2 gene product in transitional cell carcinomas of the urinary bladder: a study in Greek patients." *Modern pathology : an official journal of the United States and Canadian Academy of Pathology, Inc* (1995) 758-764, 8(7).

Gorre et al., "Clinical resistance to STI-571 cancer therapy caused by BCR-ABL gene mutation or amplification." *Science* (2001) 876-880, 293(5531).

Goss et al., "Final results of the dose escalation phase of a phase I pharmacokinetics (PK), pharmacodynamic (PD), and biological activity study of ZD1839." *Proceedings of the American Society of Clinical Oncology* (2001) 85a (Abstract 335), 20.

Graeven et al., "Phase I study of the humanised anti-EGFR monoclonal antibody matuzumab (EMD 72000) combined with gemcitabine in advanced pancreatic cancer." *British Journal of Cancer* (2006) 1293-1299, 94(9).

Grandal et al., "EGFRvIII escapes down-regulation due to impaired internalization and sorting to lysosomes." *Carcinogenesis* (2007) 1408-1417, 28(7).

Grandis et al., "Elevated levels of transforming growth factor alpha and epidermal growth factor receptor messenger RNA are early markers of carcinogenesis in head and neck cancer." *Cancer Res.* (1993) 3579-3584, 53(15).

Grandis et al., "Levels of TGF-alpha and EGFR protein in head and neck squamous cell carcinoma and patient survival." *J. Natl. Cancer Inst.* (1998) 824-832, 90(11).

Graness et al., "Protein-tyrosine-phosphatase-mediated epidermal growth factor (EGF) receptor transinactivation and EGF receptor-independent stimulation of mitogen-activated protein kinase by bradykinin in A431 cells." *Biochem. J.* (2000) 441-447, 347(Part 2).

Graus-Porta et al., "Single-chain antibody-mediated intracellular retention of ErbB-2 impairs Neu differentiation factor and epidermal growth factor signaling." *Mol. Cell Biol.* (1995) 1182-1191, 15(3).

Green et al., "Monoclonal antibody therapy for solid tumors." *Cancer Treat Rev.* (2000) 269-286, 26(4).

Greenspan et al., "Defining epitopes: It's not as easy as it seems." *Nat. Biotechnol.* (1999) 936-937, 17(10).

Grunwald et al., "Development of the epidermal growth factor receptor inhibitor OSI-774" *Seminars in Oncology* (2003) 23-31, 30(3; Suppl. 6).

Gschwind et al., "The discovery of receptor tyrosine kinases: targets for cancer therapy." *Nature Rev. Cancer* (2004) 361-370, 4(5).

Gullick, "Type I growth factor receptors: current status and future work." *Biochemical Society symposium* (1998) 193-198, 63.

Gullick, "A new model for the interaction of EGF-like ligands with their receptors: the new one-two." *Eur. J. Cancer* (1994) 2186, 30A(14).

Gullick, "Growth factors, growth factor receptors and neoplasia." *Human & experimental toxicology* (1991) 398-400, 10(6).

Gullick, "Prevalence of aberrant expression of the epidermal growth factor receptor in human cancers." *British medical bulletin* (1991) 87-98, 47(1).

Gulliford et al., "Intensification of growth factor receptor signalling by phorbol treatment of ligand-primed cells implies a dimer-stabilizing effect of protein kinase C-dependent juxtamembrane domain phosphorylation." *Cellular signalling* (1999) 245-252, 11(4).

Gunnett et al., "Phase II study of antiepidermal growth factor receptor (EGFR) antibody C225 alone in patients (pts) with metastatic renal carcinoma (RCC)." *Annual Meeting of the American Society of Clinical Oncology* (1999) 340a (Abstract 1309), 18.

Günther et al., "The secreted form of the epidermal growth factor receptor. Characterization and crystallization of the receptor-ligand complex." *JBC* (1990) 22082-22085, 265(36).

Gupta et al., "Development of an EGFRvIII specific recombinant antibody." *BMC biotechnology* (2010) 72, 10.

Güssow et al., "Humanization of monoclonal antibodies." *Methods in Enzymology* (1991) 99-121, 203.

Haas-Kogan et al., "Epidermal growth factor receptor, protein kinase B/Akt, and glioma response to erlotinib." *J. Natl. Cancer Inst.* (2005) 880-887, 97(12).

Hackel et al., "Epidermal growth factor receptors: critical mediators of multiple receptor pathways." *Current opinion in cell biology* (1999) 184-189, 11(2).

Haigler et al., "Visualization by fluorescence of the binding and internalization of epidermal growth factor in human carcinoma cells A-431." *Proceedings of the National Academy of Sciences of the United States of America* (1978) 3317-3321, 75(7).

Halatsch et al., "Marked inhibition of glioblastoma target cell tumorigenicity in vitro by retrovirus-mediated transfer of a hairpin ribozyme against deletion-mutant epidermal growth factor receptor messenger RNA." *J. Neurosurg.* (2000) 297-305, 92(2).

Halatsch et al., "Inverse correlation of epidermal growth factor receptor messenger RNA induction and suppression of anchorage-independent growth by OSI-774, an epidermal growth factor receptor tyrosine kinase inhibitor, in glioblastoma multiforme cell lines." *J. Neurosurg.* (2004) 523-533, 100(3).

Haley et al., "The human EGF receptor gene: structure of the 110 kb locus and identification of sequences regulating its transcription." *Oncogene research* (1987) 375-396, 1(4).

Haley, "Regulation of epidermal growth factor receptor expression and activation: a brief review." *Symposia of the Society for Experimental Biology* (1990) 21-37, 44.

Hambek et al., "Tumor Necrosis Factor α Sensitizes Low Epidermal Growth Factor Receptor (EGFR)-expressing Carcinomas for Anti-EGFR Therapy." *Cancer Res.* (2001) 1045-1049, 61.

Hamblett et al., "Effects of drug loading on the antitumor activity of a monoclonal antibody drug conjugate." *Clin. Cancer Res.* (2004) 7063-7070, 10(20).

Han et al., "Predictive and prognostic impact of epidermal growth factor receptor mutation in non-small-cell lung cancer patients treated with gefitinib." *J. Clin. Oncol.* (2005) 2493-2501, 23(11).

Han et al., "Tyrphostin AG 1478 preferentially inhibits human glioma cells expressing truncated rather than wild-type epidermal growth factor receptors." *Cancer Res.* (1996) 3859-3861, 56(17).

Hanahan et al., "The hallmarks of cancer." *Cell* (2000) 57-70, 100(1).

Hanks et al., "The protein kinase family: conserved features and deduced phylogeny of the catalytic domains." *Science* (1988) 42-52, 241(4861).

Hanna et al., "Phase II trial of cetuximab in patients with previously treated non-small-cell lung cancer." *Journal of Clinical Oncology* (2006) 5253-5258, 24(33).

Harari et al., "Combining radiation with molecular blockade of the EGF receptor in cancer therapy." *Proceedings of the American Association for Cancer Research* (1999) 3747s (Abstract 88), 5.

Harari et al., "Molecular mechanisms underlying ErbB2/HER2 action in breast cancer." *Oncogene* (2000) 6102-6114, 19(53).

Harari, "Epidermal growth factor receptor inhibition strategies in oncology." *Endocrine-related cancer* (2004) 689-708, 11(4).

(56) References Cited

OTHER PUBLICATIONS

Harari et al., "Head and neck cancer as a clinical model for molecular targeting of therapy: combining EGFR blockade with radiation." *Int. J. Radiat. Oncol. Biol. Phys.* (2001) 427-433, 49(2).

Harries et al., "The development and clinical use of trastuzumab (Herceptin)." *Endocrine-related cancer* (2002) 75-85, 9(2).

Harris et al., "The Role of ERBB2 Extracellular Domain in Predicting Response to Chemotherapy in Breast Cancer Patients." *Proceedings of the Annual Meeting of the American Society of Clinical Oncology* (1996) 108 (Abstract 96), 15.

Harris et al., "Epidermal Growth Factor Receptor: A Marker of Early Relapse in Breast Cancer and Tumor Stage Progression in Bladder Cancer; Interactions with neu." *In: The Molecular Diagnostics of Human Cancer* (Editors: Furth and Greaves; Publisher: Cold Spring Harbor, NY: Cold Spring Harbor Laboratory). (1989) 353-357.

Harris et al., "Therapeutic antibodies—the coming of age." *Trends in biotechnology* (1993) 42-44, 11(2).

Hatanpaa et al., "Epidermal growth factor receptor in glioma: signal transduction, neuropathology, imaging, and radioresistance." *Neoplasia* (2010) 675-684, 12(9).

Hayman et al., "Cell transformation by the epidermal growth factor receprot and v-erbB." *Cancer cells* (Cold Spring Harbor, N.Y. : 1989) (1991) 302-307, 3(8).

He et al., "Inhibition of human squamous cell carcinoma growth in vivo by epidermal growth factor receptor antisense RNA transcribed from the U6 promoter." *J. Natl. Cancer Inst.* (1998) 1080-1087, 90(14).

Heath et al., "The human A33 antigen is a transmembrane glycoprotein and a novel member of the immunoglobulin superfamily." *Proceedings of the National Academy of Sciences of the United States of America* (1997) 469-474, 94(2).

Hecht et al., "ABX-EGF monotherapy in patients (pts) with metastatic colorectal cancer (mCRC) (An updated analysis)." *Proceedings of the American Society of Clinical Oncology* (2004) 247s (Abstract 3511), 23.

Heimberger et al., "The natural history of EGFR and EGFRvIII in glioblastoma patients." *Journal of translational medicine* (2005) 38, 3.

Heimberger et al., "Prognostic effect of epidermal growth factor receptor and EGFRvIII in glioblastoma multiforme patients." *Clin. Cancer Res.* (2005) 1462-1466, 11(4).

Heimberger et al., "Epidermal growth factor receptor VIII peptide vaccination is efficacious against established intracerebral tumors." *Clin. Cancer Res.* (2003) 4247-4254, 9(11).

Heimberger et al., "Brain tumors in mice are susceptible to blockade of epidermal growth factor receptor (EGFR) with the oral, specific, EGFR-tyrosine kinase inhibitor ZD1839 (iressa)." *Clin. Cancer Res.* (2002) 3496-3502, 8(11).

Helin et al., "Internalization and down-regulation of the human epidermal growth factor receptor are regulated by the carboxyl-terminal tyrosines." *Journal of Biological Chemistry* (1991) 8363-8368, 266(13).

Helin et al., "The biological activity of the human epidermal growth factor receptor is positively regulated by its C-terminal tyrosines." *Oncogene* (1991) 825-832, 6(5).

Hendler et al., "Human squamous cell lung cancers express increased epidermal growth factor receptors." *J. Clin. Invest.* (1984) 647-651, 74(2).

Henn et al., "Polysomy of chromosome 7 is correlated with overexpression of the erbB oncogene in human glioblastoma cell lines." *Human genetics* (1986) 104-106, 74(1).

Henry et al., "A prostate-specific membrane antigen-targeted monoclonal antibody-chemotherapeutic conjugate designed for the treatment of prostate cancer." *Cancer Res.* (2004) 7995-8001, 64(21).

Hens et al., "Anti-EGFRvIII monoclonal antibody armed with 177Lu: in vivo comparison of macrocyclic and acyclic ligands." *Nucl. Med. Biol.* (2010) 741-750, 37(7).

Hens et al., "Labeling internalizing anti-epidermal growth factor receptor variant III monoclonal antibody with (177)Lu: in vitro comparison of acyclic and macrocyclic ligands." *Nucl. Med. Biol.* (2009) 117-128, 36(2).

Herbertson et al., "Phase I biodistribution and pharmacokinetic study of Lewis Y-targeting immunoconjugate CMD-193 in patients with advanced epithelial cancers." *Clin. Cancer Res.* (2009) 6709-6715, 15(21).

Herbst et al., "Regulation of postendocytic trafficking of the epidermal growth factor receptor through endosomal retention." *Journal of Biological Chemistry* (1994) 12865-12873, 269(17).

Herbst, "Dose-comparative monotherapy trials of ZD1839 in previously treated non-small cell lung cancer patients" *Seminars in Oncology* (2003) 30-38, 30(1).

Herbst et al., "IMC-C225, an anti-epidermal growth factor receptor monoclonal antibody, for treatment of head and neck cancer." *Expert opinion on biological therapy* (2001) 719-732, 1(4).

Herbst et al., "Phase II multicenter study of the epidermal growth factor receptor antibody cetuximab and cisplatin for recurrent and refractory squamous cell carcinoma of the head and neck." *J. Clin. Oncol.* (2005) 5578-5587, 23(24).

Herbst et al., "Phase I/II trial evaluating the anti-vascular endothelial growth factor monoclonal antibody bevacizumab in combination with the HER-1/epidermal growth factor receptor tyrosine kinase inhibitor erlotinib for patients with recurrent non-small-cell lung cancer." *J. Clin. Oncol.* (2005) 2544-2555, 23(11).

Herbst, "Erlotinib (Tarceva): An update on the clinical trial program" *Seminars in Oncology* (2003) 34-46, 30(3H).

Herbst et al., "IMC-C225, an anti-epidermal growth factor receptor monoclonal antibody for treatment of head and neck cancer." *Semin. Oncol.* (2002) 18-30, 29(5; Suppl. 14).

Herbst et al., "Selective oral epidermal growth factor receptor tyrosine kinase inhibitor ZD1839 is generally well-tolerated and has activity in non-small-cell lung cancer and other solid tumors: results of a phase I trial." *J. Clin. Oncol.* (2002) 3815-3825, 20(18).

Herbst et al., "Monoclonal antibodies to target epidermal growth factor receptor-positive tumors: a new paradigm for cancer therapy." *Cancer* (2002) 1593-1611, 94(5).

Herbst et al., "Epidermal growth factor receptors as a target for cancer treatment: the emerging role of IMC-C225 in the treatment of lung and head and neck cancers." *Semin. Oncol.* (2002) 27-36, 29(1 Suppl 4).

Hertler et al., "Immunotoxins: a clinical review of their use in the treatment of malignancies." *J. Clin. Oncol.* (1989) 1932-1942, 7(12).

Van Der Heyden et al., "Identification of an intracellular domain of the EGF receptor required for high-affinity binding of EGF." *FEBS letters* (1997) 265-268, 410(2-3).

Hidalgo et al., "Phase 1 trial of EKB-569, an irreversible inhibitor of the epidermal growth factor receptor (EGFR), in patients with advanced solid tumors." *Proceedings of the American Society of Clinical Oncology* (2002) 17a (Abstract 65), 21.

Hidalgo et al., "Phase I and pharmacologic study of OSI-774, an epidermal growth factor receptor tyrosine kinase inhibitor, in patients with advanced solid malignancies." *J. Clin. Oncol.* (2001) 3267-3279, 19(13).

Hirata et al., "ZD1839 (Iressa) induces antiangiogenic effects through inhibition of epidermal growth factor receptor tyrosine kinase." *Cancer Res.* (2002) 2554-2560, 62(9).

Hird et al., "Immunotherapy with Monoclonal Antibodies." *In: Genes and Cancer* (Chapter 17) (Editor: Carry; Publisher: John Wiley & Sons, Ltd). (1990) 183-189.

Hirsch et al., "Increased epidermal growth factor receptor gene number detected by fluorescence in situ hybridization associates with increased sensitivity to gefitinib in patients with bronchioloalveolar carcinoma subtypes: a Southwest Oncology Group Study." *J. Clin. Oncol.* (2005) 6838-6845, 23(28).

Hirsch et al., "Epidermal growth factor receptor in non-small-cell lung carcinomas: correlation between gene number and protein expression and impact on prognosis." *J. Clin. Oncol.* (2003) 3798-3807, 21(20).

(56) References Cited

OTHER PUBLICATIONS

Hoffman et al., "Phase I Trials of CDR-Grafted Humanized Monoclonal Antibody Hu3S193 in Patients with Lewis-Y Expressing Solid Tumors." *Proc. Am. Soc. Clin. Oncol.* (2001) Abstract 2634, 20.

Hoffmann et al., "Antitumor activity of anti-epidermal growth factor receptor monoclonal antibodies and cisplatin in ten human head and neck squamous cell carcinoma lines." *Anticancer research* (1997) 4419-4425, 17(6D).

Hogg, "Disulfide bonds as switches for protein function." *Trends Biochem. Sci.* (2003) 210-214, 28(4).

Holbro et al., "ErbB receptors: directing key signaling networks throughout life." *Annual review of pharmacology and toxicology* (2004) 195-217, 44.

Holbro et al., "The ErbB receptors and their role in cancer progression." *Exp. Cell Res.* (2003) 99-110, 284(1).

Holbrook et al., "Thermodynamic mixing of molecular states of the epidermal growth factor receptor modulates macroscopic ligand binding affinity." *Biochem. J.* (2000) 99-108, 352(Part 1).

Holland, "Glioblastoma multiforme: the terminator." *Proceedings of the National Academy of Sciences of the United States of America* (2000) 6242-6244, 97(12).

Holland et al., "A constitutively active epidermal growth factor receptor cooperates with disruption of G1 cell-cycle arrest pathways to induce glioma-like lesions in mice." *Genes Dev.* (1998) 3675-3685, 12(23).

Hollstein et al., "Amplification of epidermal growth factor receptor gene but no evidence of ras mutations in primary human esophageal cancers." *Cancer Res.* (1988) 5119-5123, 48(18).

Holm et al., "Functional mapping and single chain construction of the anti-cytokeratin 8 monoclonal antibody TS1." *Mol. Immunol.* (2007) 1075-1084, 44(6).

Holmes et al., "Structural consequences of humanizing an antibody." *Journal of immunology* (1997) 2192-2201, 158(5).

Holt et al., "Domain antibodies: proteins for therapy." *Trends in biotechnology* (2003) 484-490, 21(11).

Honegger et al., "Biological activities of EGF-receptor mutants with individually altered autophosphorylation sites." *EMBO J.* (1988) 3045-3052, 7(10).

Hong et al., "Efficacy and Safety of the Anti-Epidermal Growth Factor Antibody (EGFR) IMC-225, in Combination with Cisplatin in Patients with Recurrent Squamous Cell Carcinoma of the Head and Neck (SCCHN) Refractory to Cisplatin Containing Chemotherapy." *Proceedings of the American Society of Clinical Oncology* (2001) 224a (Abstract 895), 20.

Hooft et al., "Errors in protein structures." *Nature* (1996) 272, 381(6580).

Hortobagyi, "Overview of Treatment Results With Trastuzumab (Herceptin) in Metastatic Breast Cancer." *Seminars in Oncology* (2001) 43-47, 28(6; Suppl. 18).

Hosoi et al., "Exogenous ATP and other nucleoside phosphates modulate epidermal growth factor receptors of A-431 epidermoid carcinoma cells." *Proceedings of the National Academy of Sciences of the United States of America* (1989) 4510-4514, 86(12).

Huang et al., "The enhanced tumorigenic activity of a mutant epidermal growth factor receptor commom in the human cancers is mediated by threshold levels of constitutive tyrosine phosphorylation and unattenuated signaling." *JBC* (1997) 2927-2935, 272(5).

Huang et al., "Phosphotyrosine signaling analysis of site-specific mutations on EGFRvIII identifies determinants governing glioblastoma cell growth." *Molecular bioSystems* (2010) 1227-1237, 6(7).

Huang et al., "Uncovering therapeutic targets for glioblastoma: a systems biology approach." *Cell cycle* (Georgetown, Tex.) (2007) 2750-2754, 6(22).

Huang et al., "Quantitative analysis of EGFRvIII cellular signaling networks reveals a combinatorial therapeutic strategy for glioblastoma." *Proceedings of the National Academy of Sciences of the United States of America* (2007) 12867-12872, 104(31).

Huang et al., "Modulation of radiation response after epidermal growth factor receptor blockade in squamous cell carcinomas: inhibition of damage repair, cell cycle kinetics, and tumor angiogenesis." *Clin. Cancer Res.* (2000) 2166-2174, 6(6).

Huang et al., "Epidermal growth factor receptor blockade with C225 modulates proliferation, apoptosis, and radiosensitivity in squamous cell carcinomas of the head and neck." *Cancer Res.* (1999) 1935-1940, 59(8).

Huang et al., "Epidermal growth factor receptor inhibition in cancer therapy: biology, rationale and preliminary clinical results." *Investigational new drugs* (1999) 259-269, 17(3).

Huang et al., "Modulation of radiation response and tumor-induced angiogenesis after epidermal growth factor receptor inhibition by ZD1839 (Iressa)." *Cancer Res.* (2002) 4300-4306, 62(15).

Huang et al., "Dual-agent molecular targeting of the epidermal growth factor receptor (EGFR): combining anti-EGFR antibody with tyrosine kinase inhibitor." *Cancer Res.* (2004) 5355-5362, 64(15).

Hubbard et al., "Protein tyrosine kinase structure and function." *Annual review of biochemistry* (2000) 373-398, 69.

Hubbard, "EGF receptor inhibition: attacks on multiple fronts." *Cancer Cell* (2005) 287-288, 7(4).

Huber et al., "Trimodal cancer treatment: beneficial effects of combined antiangiogenesis, radiation, and chemotherapy." *Cancer Res.* (2005) 3643-3655, 65(9).

Hudson et al., "Engineered antibodies." *Nature Med.* (2003) 129-134, 9(1).

Humphrey et al., "Deletion-mutant epidermal growth factor receptor in human gliomas: effects of type II mutation on receptor function." *Biochem. Biophys. Res. Commun.* (1991) 1413-1420, 178(3).

Humphrey et al., "Anti-synthetic peptide antibody reacting at the fusion junction of deletion-mutant epidermal growth factor receptors in human glioblastoma." *Proceedings of the National Academy of Sciences of the United States of America* (1990) 4207-4211, 87(11).

Humphrey et al., "Amplification and expression of the epidermal growth factor receptor gene in human glioma xenografts." *Cancer Res.* (1988) 2231-2238, 48(8).

Humphreys et al., "Therapeutic antibody production technologies: molecules, applications, expression and purification." *Current opinion in drug discovery & development* (2001) 172-185, 4(2).

Hunts et al., "Hyperproduction and gene amplification of the epidermal growth factor receptor in squamous cell carcinomas." *Japanese journal of cancer research : Gann* (1985) 663-666, 76(8).

Hurtt et al., "Amplification of epidermal growth factor receptor gene in gliomas: histopathology and prognosis." *Journal of neuropathology and experimental neurology* (1992) 84-90, 51(1).

Hurwitz et al., "Bevacizumab plus irinotecan, fluorouracil, and leucovorin for metastatic colorectal cancer." *N. Engl. J. Med.* (2004) 2335-2342, 350(23).

Illidge et al., "Antibody therapy of lymphoma." *Expert opinion on pharmacotherapy* (2001) 953-961, 2(6).

Inoue et al., "Paclitaxel enhances the effects of the anti-epidermal growth factor receptor monoclonal antibody ImClone C225 in mice with metastatic human bladder transitional cell carcinoma." *Clin. Cancer Res.* (2000) 4874-4884, 6(12).

Ishida et al., "[The expression technology of chimeric and humanized antibodies]." *Nippon rinsho. Japanese journal of clinical medicine* (2002) 439-444, 60(3). English abstract of Japanese document.

Ishitoya et al., "Gene amplification and overexpression of EGF receptor in squamous cell carcinomas of the head and neck." *British Journal of Cancer* (1989) 559-562, 59(4).

Ishizawar et al., "c-Src and cooperating partners in human cancer." *Cancer Cell* (2004) 209-214, 6(3).

Iznaga-Escobar et al., "Technetium-99m-antiepidermal growth factor-receptor antibody in patients with tumors of epithelial origin: part II. Pharmacokinetics and clearances." *J. Nucl. Med.* (1998) 1918-1927, 39(11).

Jamnongjit et al., "Epidermal growth factor receptor signaling is required for normal ovarian steroidogenesis and oocyte maturation." *Proceedings of the National Academy of Sciences of the United States of America* (2005) 16257-16262, 102(45).

Janmaat et al., "Response to epidermal growth factor receptor inhibitors in non-small cell lung cancer cells: limited antiproliferative effects and absence of apoptosis associated with persistent activity of

(56) References Cited

OTHER PUBLICATIONS extracellular signal-regulated kinase or Akt kinase pathways." *Clin. Cancer Res.* (2003) 2316-2326, 9(6).

Jaros et al., "Prognostic implications of p53 protein, epidermal growth factor receptor, and Ki-67 labelling in brain tumours." *British Journal of Cancer* (1992) 373-385, 66(2).

Jay et al., "Chemical synthesis of a biologically active gene for human immune interferon-gamma. Prospect for site-specific mutagenesis and structure-function studies." *Journal of Biological Chemistry* (1984) 6311-6317, 259(10).

Jiang et al., "A novel peptide isolated from a phage display peptide library with trastuzumab can mimic antigen epitope of HER-2." *JBC* (2005) 4656-4662, 280(6).

Jiang et al., "Growth suppression of human hepatocellular carcinoma xenografts by a monoclonal antibody CH12 directed to epidermal growth factor receptor variant III." (2011) 5913-5920, 286(7).

Johns, "Targeting the Transition State" *Science's STKE* (2004) tw259, 2004(242).

Johns et al., "A Novel Antibody Directed to the Epidermal Growth Factor Receptor (EGFR) Displays Additive and Synergistic Anti-tumour Activity when used in Combination with Standard EGFR Therapeutics." *The Proceedings of the 15th Annual Lorne Cancer Conference*, Lorne, Victoria, Australia. (2003) Abstract P212.

Johns et al., "A Novel Antibody Directed to the Epidermal Growth Factor Receptor (EGFR) Displays Additive and Synergistic Anti-Tumor Activity When Used in Combination with Standard EGFR Therapeutics." *Proceedings of the International Symposium sponsored by the Cancer Research Institute*, New York, U.S.A. (2002) Abstract P-08.

Johns et al., "Biological Properties of the Glioma Associated Delta2-7 Epidermal Growth Factor Receptor." *The 11th International Conference on Second Messengers and Phosphoproteins*, Melbourne, Australia (2001) Abstract P183.

Johns et al., "Annual Branch Report 1998 ("Pre-clinical evaluation of antibodies directed to the de2-7 epidermal growth factor receptors")" *Ludwig Institute for Cancer Research* (2000) 118-119.

Johns et al., "A Novel Antibody Directed to the Epidermal Growth Factor Receptor (EGFR) Displays Additive and Synergistic Anti-tumor Activity When Used in Combination with Standard EGFR therapeutics (Abstract 2877)" *Proceedings of the American Association of Cancer Research* (2002) 580, 43.

Johns et al., "The antitumor monoclonal antibody 806 recognizes a high-mannose form of the EGF receptor that reaches the cell surface when cells over-express the receptor" *FASEB J.* (2005) 1-18, 19(3).

Johns et al., "MAb 806 enhances the efficacy of ionizing radiation in glioma xenografts expressing the de2-7 epidermal growth factor receptor." *Int. J. Radiat. Oncol. Biol. Phys.* (2010) 572-578, 78(2).

Johns et al., "The efficacy of epidermal growth factor receptor-specific antibodies against glioma xenografts is influenced by receptor levels, activation status, and heterodimerization." *Clin. Cancer Res.* (2007) 1911-1925, 13(6).

Johns et al., "The antitumor monoclonal antibody 806 recognizes a high-mannose form of the EGF receptor that reaches the cell surface when cells over-express the receptor." *FASEB J.* (2005) 780-782, 19(7).

Johns et al., "Antitumor efficacy of cytotoxic drugs and the monoclonal antibody 806 is enhanced by the EGF receptor inhibitor AG1478." *Proceedings of the National Academy of Sciences of the United States of America* (2003) 15871-15876, 100(26).

Jones et al., "A quantitative protein interaction network for the ErbB receptors using protein microarrays." *Nature* (2006) 168-174, 439(7073).

De Jong et al., "Expression of growth factors, growth-inhibiting factors, and their receptors in invasive breast cancer. II: Correlations with proliferation and angiogenesis." *The Journal of pathology* (1998) 53-57, 184(1).

Jorgensen et al., "Immunoconjugates: A Therapy Whose Time Has Come?" *Preclinica* (2004) 1-4, 2.

Jorissen et al., "Characterization of a comparative model of the extracellular domain of the epidermal growth factor receptor." *Protein science* (2000) 310-324, 9(2).

Jorissen et al., "Epidermal growth factor receptor: mechanisms of activation and signalling." *Exp. Cell Res.* (2003) 31-53, 284(1).

Jost et al., "The EGF receptor—an essential regulator of multiple epidermal functions." *European journal of dermatology : EJD* (2000) 505-510, 10(7).

Jung et al., "Local immunotherapy of glioma patients with a combination of 2 bispecific antibody fragments and resting autologous lymphocytes: evidence for in situ t-cell activation and therapeutic efficacy." *Int. J. Cancer* (2001) 225-230, 91(2).

Jutten et al., "Binding of cetuximab to the EGFRvIII deletion mutant and its biological consequences in malignant glioma cells." *Radiotherapy and oncology* (2009) 393-398, 92(3).

Kalofonos et al., "Antibody guided diagnosis and therapy of brain gliomas using radiolabeled monoclonal antibodies against epidermal growth factor receptor and placental alkaline phosphatase." *J. Nucl. Med.* (1989) 1636-1645, 30(10).

Kamat et al., "Enhanced EGFR inhibition and distinct epitope recognition by EGFR antagonistic mAbs C225 and 425." *Cancer biology & therapy* (2008) 726-733, 7(5).

Kamb et al., "A cell cycle regulator potentially involved in genesis of many tumor types." *Science* (1994) 436-440, 264(5157).

Kaminski et al., "Iodine-131-anti-B1 radioimmunotherapy for B-cell lymphoma." *J. Clin.Oncol.* (1996) 1974-1981, 14(7).

Karnes et al., "Inhibition of epidermal growth factor receptor kinase induces protease-dependent apoptosis in human colon cancer cells." *Gastroenterology* (1998) 930-939, 114(5).

Karnes et al., "Autonomous proliferation of colon cancer cells that coexpress transforming growth factor alpha and its receptor. Variable effects of receptor-blocking antibody." *Gastroenterology* (1992) 474-485, 102(2).

Karpel-Massler et al., "Therapeutic inhibition of the epidermal growth factor receptor in high-grade gliomas: where do we stand?" *Molecular cancer research : MCR* (2009) 1000-1012, 7(7).

Kashmiri et al., "Development of a minimally immunogenic variant of humanized anti-carcinoma monoclonal antibody CC49." *Crit. Rev. Oncol. Hematol.* (2001) 3-16, 38(1).

Kasprzyk et al., "Therapy of an animal model of human gastric cancer using a combination of anti-erbB-2 monoclonal antibodies." *Cancer Res.* (1992) 2771-2776, 52(10).

Katzel et al., "Recent advances of novel targeted therapy in non-small cell lung cancer." *Journal of hematology & oncology* (2009) 2, 2.

Kawagoe et al., "Immunohistochemical demonstration of epidermal growth factor (EGF) receptors in normal human placental villi." *Placenta* (1990) 7-15, 11(1).

Kawamoto et al., "Relation of epidermal growth factor receptor concentration to growth of human epidermoid carcinoma A431 cells." *Journal of Biological Chemistry* (1984) 7761-7766, 259(12).

Kawamoto et al., "Growth stimulation of A431 cells by epidermal growth factor: identification of high-affinity receptors for epidermal growth factor by an anti-receptor monoclonal antibody." *Proceedings of the National Academy of Sciences of the United States of America*(1983) 1337-1341, 80(5).

Ke et al., "Differential expression of epidermal growth factor receptor in human head and neck cancers." *Head & neck* (1998) 320-327, 20(4).

Kelly et al., "ZD1839 ('Iressa'), an oral EGFR-TKI (epidermal growth factor receptor tyrosine kinase inhibitor): Pharmacokinetic results of a phase I study in patients with advanced cancer." *Proceedings of the Annual Meeting of the American Association for Cancer Research* (2000) 612-613 (Abstract 3896), 41.

Kelly et al., "Therapeutic efficacy of 177Lu-CHX-A-DTPA-hu3S193 radioimmunotherapy in prostate cancer is enhanced by EGFR inhibition or docetaxel chemotherapy." *The Prostate* (2009) 92-104, 69(1).

Khazaeli et al., "Low Immunogenicity of a Chimeric Monoclonal Antibody (MoAb), IMC-C225, Used to Treat Epidermal Growth Factor Receptor-Positive Tumors." *Proceedings of the American Society of Clinical Oncology* (2000) 207a (Abstract 808), 19.

(56) References Cited

OTHER PUBLICATIONS

Khazaeli et al., "Human immune response to monoclonal antibodies." *Journal of immunotherapy with emphasis on tumor immunology : official journal of the Society for Biological Therapy* (1994) 42-52, 15(1).

Khazaeli et al., "Pharmacokinetics and immune response of 131I-chimeric mouse/human B72.3 (human gamma 4) monoclonal antibody in humans." *Cancer Res.* (1991) 5461-5466, 51(20).

Khazaie et al., "EGF receptor in neoplasia and metastasis." *Cancer Metastasis Rev.* (1993) 255-274, 12(3-4).

Kies et al., "Final report of the efficacy and safety of the anti-epidermal growth factor antibody Erbitux (IMC-C225), in combination with cisplatin in patients with recurrent squamous cell carcinoma of the head and neck (SCCHN) refractory to cisplatin containing chemotherapy." *Proceedings of the American Society of Clinical Oncology* (2002) 232a (Abstract 925), 21.

Kikkawa et al., "[Immunohistochemical and histopathological study of expression of epidermal growth factor receptors in gastric cancer]." *Nippon Geka Gakkai zasshi* (1993) 1231-1238, 94(12). Abstract in English of Japanese Document.

Kil et al., "A leucine-based determinant in the epidermal growth factor receptor juxtamembrane domain is required for the efficient transport of ligand-receptor complexes to lysosomes." *JBC* (1999) 3141-3150, 274(5).

Kim et al., "A phase II study of Erbitux (IMC-225), an epidermal growth factor receptor (EGFR) blocking antibody, in combination with docetaxel in chemotherapy refractory/resistant patients with advanced non-small cell lung cancer (NSCLC) (Abstract 1168)" *Proceedings of the American Society of Clinical Oncology* (2011) 293a, 21.

Kim et al., "Epidermal growth factor receptor biology (IMC-C225)." *Current opinion in oncology* (2001) 506-513, 13(6).

Kim et al., "Regulation of epidermal growth factor receptor internalization by G protein-coupled receptors." *Biochemistry* (2003) 2887-2894, 42(10).

King et al., "Preparation and preclinical evaluation of humanised A33 immunoconjugates for radioimmunotherapy." *British Journal of Cancer* (1995) 1364-1372, 72(6).

Kiyota et al., "Expression of a truncated epidermal growth factor receptor in oral squamous cell carcinomas." *Cancer Letters* (2000) 9-15, 161(1).

Kiyota et al., "Anti-epidermal growth factor receptor monoclonal antibody 225 upregulates p27(KIP1) and p15(INK4B) and induces G1 arrest in oral squamous carcinoma cell lines." *Oncology* (2002) 92-98, 63(1).

Klapper et al., "Tumor-inhibitory antibodies to HER-2/ErbB-2 may act by recruiting c-Cbl and enhancing ubiquitination of HER-2." *Cancer Res.* (2000) 3384-3388, 60(13).

Klapper et al., "Biochemical and clinical implications of the ErbB/HER signaling network of growth factor receptors." *Advances in cancer research* (2000) 25-79, 77.

Klijn et al., "The prognostic value of epidermal growth factor receptor (EGF-R) in primary breast cancer: results of a 10 year follow-up study." *Breast cancer research and treatment* (1994) 73-83, 29(1).

Klijn et al., "The clinical significance of epidermal growth factor receptor (EGF-R) in human breast cancer: a review on 5232 patients." *Endocrine reviews* (1992) 3-17, 13(1).

Klingbeil et al., "Analysis of substrate recognition determinants in a synthetic peptide containing the Tyr 1173 autophosphorylation site of the epidermal growth factor receptor." *Archives of biochemistry and biophysics* (1995) 745-750, 316(2).

Klingler-Hoffmann et al., "Inhibition of phosphatidylinositol 3-kinase signaling negates the growth advantage imparted by a mutant epidermal growth factor receptor on human glioblastoma cells." *Int. J. Cancer* (2003) 331-339, 105(3).

Klohs et al., "Inhibitors of tyrosine kinase." *Current opinion in oncology* (1997) 562-568, 9(6).

Knecht et al., "Carcinomas unresponsive to either cisplatinum or anti-EGFR therapy can be growth inhibited by combination therapy of both agents." *Anticancer research* (2003) 2577-2583, 23(3B).

Knutson et al., "Rapid, reversible internalization of cell surface insulin receptors. Correlation with insulin-induced down-regulation." *JBC* (1983) 12139-12142, 258(20).

Kondo et al., "Mapping of the human gene for epidermal growth factor receptor (EGFR) on the p13 leads to q22 region of chromosome 7." *Cytogenet. Cell Genet.* (1983) 9-14, 35(1).

Kopetz, "Synergistic effects of combination therapy with anti-EGFR and anti-Src therapy in vitro in colon cancer" *Gastrointestinal Cancers Symposium* (2007) Abstract 406.

Koprivica et al., "EGFR activation mediates inhibition of axon regeneration by myelin and chondroitin sulfate proteoglycans." *Science* (2005) 106-110, 310(5745).

Korshunov et al., "Prognostic value of tumour associated antigen immunoreactivity and apoptosis in cerebral glioblastomas: an analysis of 168 cases." *Journal of clinical pathology* (1999) 574-580, 52(8).

Kosaka et al., "Mutations of the epidermal growth factor receptor gene in lung cancer: biological and clinical implications." *Cancer Res.* (2004) 8919-8923, 64(24).

Kramer et al., "Regulation of daily locomotor activity and sleep by hypothalamic EGF receptor signaling." *Science* (2001) 2511-2515, 294(5551).

Kris et al., "A phase II trial of ZD1839 ('Iressa') in advanced non-small cell lung cancer (NSCLC) patients who had failed platinum- and docetaxel-based regimens (IDEAL 2)." *Proceedings of the American Society of Clinical Oncology* (2002) 292a (Abstract 1166), 21.

Kris et al., "Objective regressions in non-small-cell lung cancer patients treated in phase I trials of oral ZD1839 (Iressa), a selective tyrosine kinase inhibitor that blocks the epidermal growth factor receptor (EGFR) (Abstract 233)" *Lung Cancer* (2000) 72, 29.

Krug et al., "Targeting Lewis Y (Le(y)) in small cell lung cancer with a humanized monoclonal antibody, hu3S193: a pilot trial testing two dose levels." *Journal of thoracic oncology : official publication of the International Association for the Study of Lung Cancer* (2007) 947-952, 2(10).

Kuan et al., "EGF mutant receptor villas a molecular target in cancer therapy." *Endocrine-related cancer* (2001) 83-96, 8(2).

Kuan et al., "Increased binding affinity enhances targeting of glioma xenografts by EGFRvIII-specific scFv." *Int. J. Cancer* (2000) 962-969, 88(6).

Kuan et al., "EGFRvIII as a promising target for antibody-based brain tumor therapy." *Brain tumor pathology* (2000) 71-78, 17(2).

Kuan et al., "125I-labeled anti-epidermal growth factor receptor-vIII single-chain Fv exhibits specific and high-level targeting of glioma xenografts." *Clin. Cancer Res.* (1999) 1539-1549, 5(6).

Kumar et al., "Regulation of phosphorylation of the c-erbB-2/HER2 gene product by a monoclonal antibody and serum growth factor(s) in human mammary carcinoma cells." *Mol. Cell Biol.* (1991) 979-986, 11(2).

Kunkel et al., "Inhibition of the epidermal growth factor receptor tyrosine kinase by PD153035 in human A431 tumors in athymic nude mice." *Investigational new drugs* (1996) 295-302, 13(4).

Kurpad et al., "Tumor antigens in astrocytic gliomas." *Glia* (1995) 244-256, 15(3).

Kwok et al., "Cell cycle dependence of epidermal growth factor induced radiosensitization." *Int. J. Radiat. Oncol. Biol. Phys.* (1992) 525-527, 22(3).

Kwok et al., "Differences in EGF related radiosensitisation of human squamous carcinoma cells with high and low numbers of EGF receptors." *British Journal of Cancer* (1991) 251-254, 64(2).

Lackmann et al., "Eph, a protein family coming of age: more confusion, insight, or complexity?" *Science signaling* (2008) re2, 1(15).

Lacouture, "Mechanisms of cutaneous toxicities to EGFR inhibitors." *Nature Rev Cancer* (2006) 803-812, 6(10).

Laderoute et al., "Epidermal growth factor modifies cell cycle control in A431 human squamous carcinoma cells damaged by ionizing radiation." *Cancer Res.* (1994) 1407-1411, 54(6).

Lakowicz, "Principles of Fluorescence Spectroscopy" *Principles of fluorescence spectroscopy*. 2nd edit, Kluwer Academic/Plenum, New York (1999) Table of Contents.

(56) References Cited

OTHER PUBLICATIONS

Lal et al., "Mutant epidermal growth factor receptor up-regulates molecular effectors of tumor invasion." *Cancer Res.* (2002) 3335-3339, 62(12).
Lammering et al., "Radiosensitization of malignant glioma cells through overexpression of dominant-negative epidermal growth factor receptor." *Clin. Cancer Res.* (2001) 682-690, 7(3).
Lammering et al., "Inhibition of the type III epidermal growth factor receptor variant mutant receptor by dominant-negative EGFR-CD533 enhances malignant glioma cell radiosensitivity." *Clin. Cancer Res.* (2004) 6732-6743, 10(19).
Lammering et al., "EGFRvIII-mediated radioresistance through a strong cytoprotective response." *Oncogene* (2003) 5545-5553, 22(36).
Lammerts Van Bueren et al., "The antibody zalutumumab inhibits epidermal growth factor receptor signaling by limiting intra- and intermolecular flexibility." *Proceedings of the National Academy of Sciences of the United States of America* (2008) 6109-6114, 105(16).
Lammerts Van Bueren et al., "Effect of target dynamics on pharmacokinetics of a novel therapeutic antibody against the epidermal growth factor receptor: implications for the mechanisms of action." *Cancer Res.* (2006) 7630-7638, 66(15).
Landry et al., "Antibody recognition of a conformational epitope in a peptide antigen: Fv-peptide complex of an antibody fragment specific for the mutant EGF receptor, EGFRvIII." *J. Mol. Biol.* (2001) 883-893, 308(5).
Langedijk et al., "Antigenic structure of the central conserved region of protein G of bovine respiratory syncytial virus." *Journal of virology* (1997) 4055-4061, 71(5).
Lango et al., "Targeting growth factor receptors: integration of novel therapeutics in the management of head and neck cancer." *Current opinion in oncology* (2001) 168-175, 13(3).
Lanzetti et al., "The Eps8 protein coordinates EGF receptor signalling through Rac and trafficking through RabS." *Nature* (2000) 374-377, 408(6810).
Lapthorn et al., "Cystine nooses and protein specificity." *Nature structural biology* (1995) 266-268, 2(4).
De Larco et al., "Sarcoma growth factor from mouse sarcoma virus-transformed cells. Purification by binding and elution from epidermal growth factor receptor-rich cells." *JBC* (1980) 3685-3690, 255(8).
De Larco et al., "Epithelioid and fibroblastic rat kidney cell clones: epidermal growth factor (EGF) receptors and the effect of mouse sarcoma virus transformation." *Journal of cellular physiology* (1978) 335-342, 94(3).
Larysz et al., "Epidermal growth factor receptor gene expression in high grade gliomas?" *Folia neuropathologica / Association of Polish Neuropathologists and Medical Research Centre, Polish Academy of Sciences* (2011) 28-38, 49(1).
Laskowski et al., "PROCHECK: a program to check the stereochemical quality of protein structures" *J. Appl. Cryst.* (1993) 283-291, 26.
Lassman et al., "Response of glioblastomas to EGFR kinase inhibitors." *N. Engl. J. Med.* (2006) 525-6; author reply 525-6, 354(5).
Lautrette et al., "Angiotensin II and EGF receptor cross-talk in chronic kidney diseases: a new therapeutic approach." *Nature Med.* (2005) 867-874, 11(8).
Lawrentschuk et al., "Assessing regional hypoxia in human renal tumours using 18F-fluoromisonidazole positron emission tomography." *BJU international* (2005) 540-546, 96(4).
Lax et al., "Epidermal growth factor (EGF) induces oligomerization of soluble, extracellular, ligand-binding domain of EGF receptor. A low resolution projection structure of the ligand-binding domain." *JBC* (1991) 13828-13833, 266(21).
Lax et al., "Noncontiguous regions in the extracellular domain of EGF receptor define ligand-binding specificity." *Cell regulation* (1991) 337-345, 2(5).
Lax et al., "Functional analysis of the ligand binding site of EGF-receptor utilizing chimeric chicken/human receptor molecules." *EMBO J.* (1989) 421-427, 8(2).

Leahy et al., "A mammalian expression vector for expression and purification of secreted proteins for structural studies." *Protein Expr. Purif.* (2000) 500-506, 20(3).
Learn et al., "Resistance to tyrosine kinase inhibition by mutant epidermal growth factor receptor variant III contributes to the neoplastic phenotype of glioblastoma multiforme." *Clin. Cancer Res.* (2004) 3216-3224, 10(9).
Lee et al., "ImmunoPET detection of xenografts expressing de2-7 EGFR using Iodine-124 labelled ch806 via residualising ligand IMPR4" *J. Nucl. Med.* (2006) 429P, 47(5, Suppl. 1).
Lee et al., "Immuno-PET of human colon xenograft-bearing BALB/c nude mice using 124I-CDR-grafted humanized A33 monoclonal antibody." *J. Nucl. Med.* (2001) 764-769, 42(5).
Lee et al., "Immuno-PET quantitation of de2-7 epidermal growth factor receptor expression in glioma using 124I-IMP-R4-labeled antibody ch806." *J. Nucl. Med.* (2010) 967-972, 51(6).
Lee et al., "Enhanced efficacy of radioimmunotherapy with 90Y-CHX-A"-DTPA-hu3S193 by inhibition of epidermal growth factor receptor (EGFR) signaling with EGFR tyrosine kinase inhibitor AG1478." *Clin. Cancer Res.* (2005) 7080s-7086s, 11.
Lee et al., "Immuno-PET for tumor targeting." *J. Nucl. Med.* (2003) 1282-1283, 44(8).
Lee et al., "Therapeutic efficacy of antiglioma mesenchymal extracellular matrix 131I-radiolabeled murine monoclonal antibody in a human glioma xenograft model." *Cancer Res.* (1988) 559-566, 48(3).
Legge, "Computational Design of Humanized Antibodies against the Epidermal Growth Factor Receptor (PhD Thesis)" *Submitted in total fulfillment of the requirements of the degree of Doctor of Philosophy*. University of Melbourne. (2003) 1-278.
Lei et al., "Enhancement of chemosensitivity and programmed cell death by tyrosine kinase inhibitors correlates with EGFR expression in non-small cell lung cancer cells." *Anticancer research* (1999) 221-228, 19.
Lenferink et al., "Blockade of the epidermal growth factor receptor tyrosine kinase suppresses tumorigenesis in MMTV/Neu + MMTV/TGF-alpha bigenic mice." *Proceedings of the National Academy of Sciences of the United States of America* (2000) 9609-9614, 97(17).
Lenz et al., "Consistent Response to Treatment with Cetuximab Monotherapy in Patients with Metastatic Colorectal Cancer." *Journal of Clinical Oncology*, 2005 ASCO Annual Meeting Proceedings (2005) Abstract 3536, 23(16S; Part I of II: Jun. 1 Supplement).
Lenz et al., "Multicenter phase II and translational study of cetuximab in metastatic colorectal carcinoma refractory to irinotecan, oxaliplatin, and fluoropyrimidines." *Journal of Clinical Oncology* (2006) 4914-4921, 24(30).
Leon et al., "Genetic aberrations in human brain tumors." *Neurosurgery* (1994) 708-722, 34(4).
Leu et al., "Functional implication of the interaction between EGF receptor and c-Src." *Frontiers in bioscience : a journal and virtual library* (2003) s28-38, 8.
Levitzki et al., "Tyrosine kinase inhibition: an approach to drug development." *Science* (1995) 1782-1788, 267(5205).
Lewis Phillips et al., "Targeting HER2-Positive Breast Cancer with Trastuzumab-DM1, an Antibody-Cytotoxic Drug Conjugate" *Cancer Research* (2008) 9280-9290, 68(22).
Li et al., "Mutant epidermal growth factor receptor displays increased signaling through the phosphatidylinositol-3 kinase/AKT pathway and promotes radioresistance in cells of astrocytic origin." *Oncogene* (2004) 4594-4602, 23(26).
Li et al., "Resistance to small molecule inhibitors of epidermal growth factor receptor in malignant gliomas." *Cancer Res.* (2003) 7443-7450, 63(21).
Li et al., "Therapeutic anti-EGFR antibody 806 generates responses in murine de novo EGFR mutant-dependent lung carcinomas." *J. Clin. Invest.* (2007) 346-352, 117(2).
Li et al., "EGF receptor variant III as a target antigen for tumor immunotherapy." *Expert Review of Vaccines* (2008) 977-985, 7(7).
Li et al., "Structural basis for EGF receptor inhibition by the therapeutic antibody IMC-11F8." *Structure* (2008) 216-227, 16(2).
Libermann et al., "Amplification, enhanced expression and possible rearrangement of EGF receptor gene in primary human brain tumours of glial origin." *Nature* (1985) 144-147, 313(5998).

(56) References Cited

OTHER PUBLICATIONS

Libermann et al., "Expression of epidermal growth factor receptors in human brain tumors." *Cancer Res.* (1984) 753-760, 44(2).
Lichtner et al., "Signaling-inactive epidermal growth factor receptor/ligand complexes in intact carcinoma cells by quinazoline tyrosine kinase inhibitors." *Cancer Res.* (2001) 5790-5795, 61(15).
Lin et al., "Expression cloning of human EGF receptor complementary DNA: gene amplification and three related messenger RNA products in A431 cells." *Science* (1984) 843-848, 224(4651).
Lindmo et al., "Determination of the immunoreactive fraction of radiolabeled monoclonal antibodies by linear extrapolation to binding at infinite antigen excess." *J. Immunol. Methods* (1984) 77-89, 72(1).
Lipton et al., "Elevated Serum HER-2/neu Level Predicts Decreased Response to Hormone Therapy in Metastatic Breast Cancer." *Proceedings of the American Society of Clinical Oncology* (2000) 71a (Abstract 274), 19.
Little et al., "Of mice and men: hybridoma and recombinant antibodies." *Immunology Today* (2000) 364-370, 21(8).
Liu et al., "Epidermal growth factor receptor activation: an upstream signal for transition of quiescent astrocytes into reactive astrocytres after neural injury." *The Journal of neuroscience : the offical journal of the Society for Neuroscience* (2006) 7532-7540, 26(28).
Liu et al., "Clinical significance of EGFR amplification and the aberrant EGFRvIII transcript in conventionally treated astrocytic gliomas." *Journal of Molecular Medicine* (Berlin, Germany) (2005) 917-926, 83(11).
Liu et al., "The effect of epidermal growth factor receptor variant III on glioma cell migration by stimulating ERK phosphorylation through the focal adhesion kinase signaling pathway." *Archives of Biochemistry and Biophysics* (2010) 89-95, 502(2).
Liu et al., "Engineering therapeutic monoclonal antibodies." *Immunological reviews* (2008) 9-27, 222.
Liu et al., "Generation of anti-idiotype antibodies for application in clinical immunotherapy laboratory analyses." *Hybridoma and hybridomics* (2003) 219-228, 22(4).
Livneh et al., "Reconstitution of human epidermal growth factor receptors and its deletion mutants in cultured hamster cells." *Journal of Biological Chemistry* (1986) 12490-12497, 261(27).
Lo, "EGFR-targeted therapy in malignant glioma: novel aspects and mechanisms of drug resistance." *Current Molecular Pharmacology* (2010) 37-52, 3(1).
Lobuglio et al., "Mouse/human chimeric monoclonal antibody in man: kinetics and immune response." *Proceedings of the National Academy of Sciences of the United States of America* (1989) 4220-4224, 86(11).
Loew et al., "The epidermal growth factor receptor as a therapeutic target in glioblastoma multiforme and other malignant neoplasms." *Anti-Cancer Agents in Medicinal Chemistry* (2009) 703-715, 9(6).
Lofts et al., "c-erbB2 amplification and overexpression in human tumors." In: *Genes, Oncogenes, and Hormones: Advances in Cellular and Molecular Biology of Breast Cancer* (Editors: Dickson and Lippman; Publisher: Kluwer Academic, Boston, MA). (1992) 161-179.
Van De Loosdrecht et al., "A tetrazolium-based colorimetric MTT assay to quantitate human monocyte mediated cytotoxicity against leukemic cells from cell lines and patients with acute myeloid leukemia." *J. Immunol. Methods* (1994) 311-320, 174(1-2).
Di Lorenzo et al., "Expression of epidermal growth factor receptor correlates with disease relapse and progression to androgen-independence in human prostate cancer." *Clin. Cancer Res.* (2002) 3438-3444, 8(11).
Lorimer et al., "Activation of extracellular-regulated kinases by normal and mutant EGF receptors." *Biochimica et biohysica acta* (2001) 1-9, 1538(1).
Lorimer et al., "Recombinant immunotoxins specific for a mutant epidermal growth factor receptor: targeting with a single chain antibody variable domain isolated by phage display." *Proceedings of the National Academy of Sciences of the United States of America* (1996) 14815-14820, 93(25).
Lorimer et al., "Immunotoxins that target an oncogenic mutant epidermal growth factor receptor expressed in human tumors." *Clin. Cancer Res.* (1995) 859-864, 1(8).
Lorimer, "Mutant epidermal growth factor receptors as targets for cancer therapy." *Current Cancer Drug Targets* (2002) 91-102, 2(2).
Lorusso et al., "Improvements in quality of life and disease-related symptoms in phase I trials of the selective oral epidermal growth factor receptor tyrosine kinase inhibitor ZD1839 in non-small cell lung cancer and other solid tumors." *Clin. Cancer Res.* (2003) 2040-2048, 9(6).
Lu et al., "Fyn and SRC are effectors of oncogenic epidermal growth factor receptor signaling in glioblastoma patients." *Cancer Res.* (2009) 6889-6898, 69(17).
Ludwig Institute for Cancer Research, "Annual Branch Report 2005" *Ludwig Institute for Cancer Research* (2010) 1-7.
Ludwig Institute for Cancer Research, "Annual Research Report 2002-2003" *Ludwig Institute for Cancer Research* (2003) 1-7.
Ludwig Institute for Cancer Research, "Clinical Trial Confirms Novel EGFR Antibody Targets Tumours but not Normal Tissues" *Ludwig Institute for Cancer Research* (2010).
Ludwig Institute for Cancer Research, "Annual Research Highlights Report 2006" *Ludwig Institute for Cancer Research* (2007) 1-56.
Ludwig Institute for Cancer Research, "Annual Research Highlights Report 2005" *Ludwig Institute for Cancer Research* (2005) 3.
Ludwig Institute for Cancer Research, "Annual Research Report 2004" *Ludwig Institute for Cancer Research* (2004) 7, 12, 79, 83-84, 98, 204 and 240.
Ludwig Institute for Cancer Research, "Annual Research Report 2002" *Ludwig Institute for Cancer Research* (2003) 8, 84-86 and 99-100.
Ludwig Institute for Cancer Research, "Annual Research Report 2003" *Ludwig Institute for Cancer Research* (2003) 81-83, 93 and 152.
Ludwig Institute for Cancer Research, "Annual Report 1999-2000" *Ludwig Institute for Cancer Research* (2000) 1-13.
Lui et al., "EGFR-mediated cell cycle regulation." *Anticancer research* (2002) 1-11, 22(1A).
Lund et al., "Phosphorylation of the epidermal growth factor receptor at threonine 654 inhibits ligand-induced internalization and down-regulation." *Journal of Biological Chemistry* (1990) 20517-20523, 265(33).
Luwor et al., "A Soluble Form of the Epidermal Growth Factor Receptor (EGFR) Specific Tyrosine Kinase Inhibitor AG1478 Enhances the Efficacy of Chemotherapy." *Proceedings of the American Association for Cancer Research* (2002) 784 (Abstract 3885), 43.
Luwor et al., "The 806 Antibody Inhibits the Growth of Tumor Xenografts Expressing either the de2-7 or Amplified Epidermal Growth Factor Receptor (EGFR) but not Wild-Type EGFR." *Austin and Repatriation Medical Centre Research Week* (2001) Abstract 46.
Luwor et al., "The 806 Antibody Inhibits the Growth of Tumor Xenografts Expressing either the de2-7 or Amplified Epidermal Growth Factor Receptor (EGFR) but not Wild-Type EGFR." *Proceedings of the 13th Annual Lorne Cancer Conference*, Lorne, Victoria, Australia (2001) Abstract 208.
Luwor et al., "Monoclonal Antibody 806 Inhibits the Growth of Tumor Xenografts Expressing either the de2-7 or Amplified Epidermal Growth Factor Receptor (EGFR) but not Wild-Type EGFR." *Austin and Repatriation Medical Centre Research Week* (2000) Poster Presentation (Abstract 88).
Luwor et al., "Monoclonal Antibody 806 Inhibits the Growth of Tumor Xenografts Expressing either the de2-7 or Amplified Epidermal Growth Factor Receptor (EGFR) but not Wild-Type EGFR." *Austin and Repatriation Medical Centre Research Week* (2000) Abstract 88.
Luwor, "The Monoclonal Antibody 806 and tyrosine Kinase inhibitor AG1478: Novel epidermal growth factor receptor therapeutics (PhD Thesis)" *Submitted in Total Fulfilment of the Requirements for the Degree of Doctor of Philosophy*, University of Melbourne. (2003) 1-331.
Luwor et al., "The tumor-specific de2-7 epidermal growth factor receptor (EGFR) promotes cells survival and heterodimerizes with the wild-type EGFR." *Oncogene* (2004) 6095-6104, 23(36).

(56) References Cited

OTHER PUBLICATIONS

Lyall et al., "EGF induces receptor down-regulation with no receptor reycling in KB Cells" *Chemical Abstracts* (1985) 56832q, 102(7).

Lydon et al., "A potent protein-tyrosine kinase inhibitor which selectively blocks proliferation of epidermal growth factor receptor-expressing tumor cells in vitro and in vivo." *Int. J. Cancer* (1998) 154-163, 76(1).

Lynch et al., "A phase II trial of cetuximab as therapy for recurrent non-small cell lung cancer (NSCLC)." *Proceedings of the American Society of Clinical Oncology* (2004) 637s (Abstract 7084), 23.

Lynch et al., "Therapeutic potential of ABX-EGF: a fully human anti-epidermal growth factor receptor monoclonal antibody for cancer treatment." *Semin. Oncol.* (2002) 47-50, 29(1 Suppl 4).

MacCallum et al., "Antibody-antigen interactions: contact analysis and binding site topography." *J. Mol. Biol.* (1996) 732-745, 262(5).

MacDiarmid et al., "Sequential treatment of drug-resistant tumors with targeted minicells containing siRNA or a cytotoxic drug." *Nat. Biotechnol.* (2009) 643-651, 27(7).

MacDonald et al., "Production and response of a human prostatic cancer line to transforming growth factor-like molecules." *British Journal of Cancer* (1990) 579-584, 62(4).

Mach, "Monoclonal Antibodies." In: *Oxford Textbook of Oncology* (Chapter 1.8) (Editors: Peckham et al.; Publisher: Oxford Univ. Press, Oxford). (1995) 81-103, 1.

Machiels et al., "Zalutumumab plus best supportive care versus best supportive care alone in patients with recurrent or metastatic squamous-cell carcinoma of the head and neck after failure of platinum-based chemotherapy: an open-label, randomised phase 3 trial" *The Lancet Oncology* (2011) 333-343, 12(4).

Maciag, "The human epidermal growth factor receptor-kinase complex" *Trends in Biochemical Sciences* (1982) 197-198, 7.

Maeda et al., "pH-dependent receptor/ligand dissociation as a determining factor for intracellular sorting of ligands for epidermal growth factor receptors in rat hepatocytes." *Journal of controlled release : official journal of the Controlled Release Society* (2002) 71-82, 82(1).

Magné et al., "Influence of epidermal growth factor receptor (EGFR), p53 and intrinsic MAP kinase pathway status of tumour cells on the antiproliferative effect of ZD1839 ('Iressa')." *British Journal of Cancer* (2002) 1518-1523, 86(9).

Malden et al., "Selective amplification of the cytoplasmic domain of the epidermal growth factor receptor gene in glioblastoma multiforme." *Cancer Res.* (1988) 2711-2714, 48(10).

Malik et al., "Safety and efficacy of panitumumab monotherapy in patients with metastatic colorectal cancer (mCRC)" *Journal of Clinical Oncology*, 2005 ASCO Annual Meeting Proceedings (2005) Abstract 3520, 23(16S; Part I of II: Jun. 1 Supplement).

Malik et al., "Pharmacodynamic evaluation of the epidermal growth factor receptor inhibitor OSI-774 in human epidermis of cancer patients." *Clin. Cancer Res.* (2003) 2478-2486, 9(7).

Maloney et al., "IDEC-C2B8 (Rituximab) anti-CD20 monoclonal antibody therapy in patients with relapsed low-grade non-Hodgkin's lymphoma." *Blood* (1997) 2188-2195, 90(6).

Mamot et al., "Epidermal growth factor receptor-targeted immunoliposomes significantly enhance the efficacy of multiple anticancer drugs in vivo." *Cancer Res.* (2005) 11631-11638, 65(24).

Mamot et al., "Epidermal growth factor receptor (EGFR)-targeted immunoliposomes mediate specific and efficient drug delivery to EGFR- and EGFRvIII-overexpressing tumor cells." *Cancer Res.* (2003) 3154-3161, 63(12).

Mano et al., "Phase I trial of zalutumumab and irinotecan in metastatic colorectal cancer patients who have failed irinotecan- and cetuximab-based therapy" *ASCO Meeting* 2009).

Margolis et al., "All autophosphorylation sites of epidermal growth factor (EGF) receptor and HER2/neu are located in their carboxyl-terminal tails. Identification of a novel site in EGF receptor." *JBC* (1989) 10667-10671, 264(18).

Marie et al., "EGFR tyrosine kinase domain mutations in human gliomas." *Neurology* (2005) 1444-1445, 64(8).

Mariuzza et al., "The structural basis of antigen-antibody recognition." *Annual review of biophysics and biophysical chemistry* (1987) 139-159, 16.

Markowitz et al., "Growth stimulation by coexpression of transforming growth factor-alpha and epidermal growth factor-receptor in normal and adenomatous human colon epithelium." *J. Clin. Invest.* (1990) 356-362, 86(1).

Marks et al., "By-passing immunization: building high affinity human antibodies by chain shuffling." *Bio/technology* (Nature Publishing Company) (1992) 779-783, 10(7).

Martinazzi et al., "Epidermal growth factor receptor immunohistochemistry in different histological types of infiltrating breast carcinoma." *Journal of Clinical Pathology* (1993) 1009-1010, 46(11).

Maruo et al., "Immunohistochemical demonstration of elevated expression of epidermal growth factor receptor in the neoplastic changes of cervical squamous epithelium." *Cancer* (1992) 1182-1187, 69(5).

Masui et al., "Treatment with anti-EGF receptor monoclonal antibody causes regression of DiFi human colorectal carcinoma xenografts." *Proceedings of the American Association for Cancer Research* (1991) 394 (Abstract 2340), 32.

Masui et al., "Enhanced tumorigenesis of NR6 cells which express non-down-regulating epidermal growth factor receptors." *Cancer Res.* (1991) 6170-6175, 51(22).

Masui et al., "Cytotoxicity against human tumor cells mediated by the conjugate of anti-epidermal growth factor receptor monoclonal antibody to recombinant ricin A chain." *Cancer Res.* (1989) 3482-3488, 49(13).

Masui et al., "Mechanism of antitumor activity in mice for anti-epidermal growth factor receptor monoclonal antibodies with different isotypes." *Cancer Res.* (1986) 5592-5598, 46(11).

Masui et al., "Growth inhibition of human tumor cells in athymic mice by anti-epidermal growth factor receptor monoclonal antibodies." *Cancer Res.* (1984) 1002-1007, 44(3).

Matar et al., "Combined epidermal growth factor receptor targeting with the tyrosine kinase inhibitor gefitinib (ZD1839) and the monoclonal antibody cetuximab (IMC-C225): superiority over single-agent receptor targeting." *Clin. Cancer Res.* (2004) 6487-6501, 10(19).

Mateo et al., "Humanization of a mouse monoclonal antibody that blocks the epidermal growth factor receptor: recovery of antagonistic activity." *Immunotechnology : an International Journal of Immunological Engineering* (1997) 71-81, 3(1).

Matsumoto et al., "Blockade of EGF-R signaling with anti-EGFR monoclonal antibody (Mab) C225 inhibits matrix metalloproteinase-9 (MMP-9) expression and invasion of human transitional cell carcinoma (TCC) in vitro and in vivo." *Proceedings of the American Association for Cancer Research* (1998) 3 (Abstract 565), 39.

Matsuo et al., "ZD1839, a selective epidermal growth factor receptor tyrosine kinase inhibitor, shows antimetastatic activity using a hepatocellular carcinoma model." *Molecular Cancer Therapeutics* (2003) 557-561, 2(6).

Mattoon et al., "The tethered configuration of the EGF receptor extracellular domain exerts only a limited control of receptor function." *Proceedings of the National Academy o Sciences of the United States of America* (2004) 923-928, 101(4).

Maurizi et al., "Prognostic significance of epidermal growth factor receptor in laryngeal squamous cell carcinoma." *British Journal of Cancer* (1996) 1253-1257, 74(8).

Mayes et al., "Biosynthesis of the epidermal growth factor receptor in A431 cells." *Embo J.* (1984) 531-537, 3(3).

McCafferty et al., "Phage antibodies: filamentous phage displaying antibody variable domains." *Nature* (1990) 552-554, 348(6301).

McLeod et al., "In vivo pharmacology and anti-tumour evaluation of the tyrphostin tyrosine kinase inhibitor RG13022." *British Journal of Cancer* (1996) 1714-1718, 74(11).

Mehra et al., "Efficient mapping of protein antigenic determinants." *Proceedings of the National Academy of Sciences of the United States of America* (1986) 7013-7017, 83(18).

Meikrantz et al., "Apoptosis and the cell cycle." *J. Cell Biochem.* (1995) 160-174, 58(2).

(56) References Cited

OTHER PUBLICATIONS

Meilhoc et al., "High efficiency transformation of intact yeast cells by electric field pulses." *Bio/technology* (Nature Publishing Company) (1990) 223-227, 8(3).
Mellinghoff et al., "PTEN-mediated resistance to epidermal growth factor receptor kinase inhibitors." *Clin. Cancer Res.* (2007) 378-381, 13(2 Pt 1).
Mellinghoff et al., "Molecular determinants of the response of glioblastomas to EGFR kinase inhibitors." *N. Engl. J. Med.* (2005) 2012-2024, 353(19).
Mellstedt, "Monoclonal antibodies in human cancer." *Drugs of Today* (Barcelona, Spain : 1998) (2003) 1-16, 39(Suppl. C).
Mendelsohn et al., "A phase I study of chimerized anti-epidermal growth factor receptor (EGFR) monoclonal antibody, C225, in combination with cisplatin (CDDP) in patients (pts) with recurrent head and neck squamous cell carcinoma (SCC)." *Annual Meeting of the American Society of Clinical Oncology* (1999) 389a (Abstract 1502), 18.
Mendelsohn et al., "Antibodies to growth factors and receptors." *In: Biologic Therapy of Cancer* (Section 21.6) (Editors: DeVita, et al.: Publisher: JB Lippincott Co.) (1995) 607-623.
Mendelsohn et al., "Principles of molecular cell biology of cancer: growth factors." *In: Cancer: Principles and Practice of Oncology* (Chapter 7) (Editors: DeVita, et al.; Publisher: J.B. Lippincott, Philadelphia). (1993) 114-133.
Mendelsohn et al., "The Willet F. Whitmore, Jr., Lectureship: blockade of epidermal growth factor receptors as anticancer therapy." *The Journal of Urology* (2001) 1152-1157, 165(4).
Mendelsohn, "The epidermal growth factor receptor as a target for cancer therapy." *Endocrine-Related Cancer* (2001,) 3-9, 8(1).
Mendelsohn, "Blockade of receptors for growth factors: an anticancer therapy—the fourth annual Joseph H Burchenal American Association of Cancer Research Clinical Research Award Lecture." *Clin. Cancer Res.* (2000) 747-753, 6(3).
Mendelsohn, "Epidermal growth factor receptor inhibition by a monoclonal antibody as anticancer therapy." *Clin. Cancer Res.* (1997) 2703-2707, 3(12 Pt 2).
Mendelsohn et al., "Epidermal growth factor receptor family and chemosensitization." *J. Natl. Cancer Inst.* (1997) 341-343, 89(5).
Mendelsohn et al., *In Cellular and Molecular Bio. of Tumors and Preventative Clinical Applications* (New York: Alan R. Liss, Inc.) (1988) 307-312 (Reference not available).
Mendelsohn et al., "Anti-epidermal growth factor receptor monoclonal antibodies may inhibit A431 tumor cell proliferation by blocking an autocrine pathway." *Transactions of the Association of American Physicians* (1987) 173-178, 100.
Mendelsohn et al., "Epidermal growth factor receptor targeting in cancer." *Semin. Oncol.* (2006) 369-385, 33(4).
Mendelsohn et al., "Status of epidermal growth factor receptor antagonists in the biology and treatment of cancer." *J. Clin. Oncol.* (2003) 2787-2799, 21(14).
Mendelsohn, "Targeting the epidermal growth factor receptor for cancer therapy." *J. Clin. Oncol.* (2002) 1S-13S, 20(18 Suppl).
Merlino et al., "Structure and localization of genes encoding aberrant and normal epidermal growth factor receptor RNAs from A431 human carcinoma cells." *Mol. Cell. Biol.* (1985) 1722-1734, 5(7).
Messa et al., "EGF, TGF-alpha, and EGF-R in human colorectal adenocarcinoma." *Acta oncoloqica* (Stockholm, Sweden) (1998) 285-289, 37(3).
Messing et al., "Epidermal growth factor—interactions with normal and malignant urothelium: in vivo and in situ studies." *The Journal of Urology* (1987) 1329-1335, 138(5).
Mickey et al., "Heterotransplantation of a human prostatic adenocarcinoma cell line in nude mice." *Cancer Res.* (1977) 4049-4058, 37(11).
Milano et al., "EGFR-targeting drugs in combination with cytotoxic agents: from bench to bedside, a contrasted reality." *British Journal of Cancer* (2008) 1-5, 99(1).

Milas et al., "In vivo enhancement of tumor radioresponse by C225 antiepidermal growth factor receptor antibody." *Clin. Cancer Res.* (2000) 701-708, 6(2).
Miller et al., "A Pilot Trial Demonstrates the Safety of ZD1839 (Iressa), an Oral Epidermal Growth Factor Receptor Tyrosine Kinase Inhibitor (EGFR-TKI), in Combination with Carboplatin (C) and Paclitaxel (P) in Previously Untreated Advanced Non-Small Cell Lung Cancer (NSCLC)." *Proc. Am. Soc. Clin. Oncol.* (2001) Abstract 1301, 20.
Mills et al., "Fully human antibodies to MCAM/MUC18 inhibit tumor growth and metastasis of human melanoma." *Cancer Res.* (2002) 5106-5114, 62(17).
Mineo et al., "Regulated migration of epidermal growth factor receptor from caveolae." *JBC* (1999) 30636-30643, 274(43).
Mischel et al., "Targeted molecular therapy of GBM." *Brain Pathology* (Zurich, Switzerland) (2003) 52-61, 13(1).
Mishima et al., "Expression of a tumor-specific mutant epidermal growth factor receptor mediates glioma cell invasion in vivo" *Proc. Am. Assoc. Cancer Res.* (1999) 519, 40.
Mishima et al., "A peptide derived from the non-receptor-binding region of urokinase plasminogen activator inhibits glioblastoma growth and angiogenesis in vivo in combination with cisplatin." *Proceedings of the National Academy of Sciences of the United States of America* (2000) 8484-8489, 97(15).
Mitra et al., "Passive antibody-mediated immunotherapy for the treatment of malignant gliomas." *Neurosurgery Clinics of North America* (2010) 67-76, 21(1).
Moasser et al., "The tyrosine kinase inhibitor ZD1839 ('Iressa') inhibits HER2-driven signaling and suppresses the growth of HER2-overexpressing tumor cells." *Cancer Res.* (2001) 7184-7188, 61(19).
Modjtahedi et al., "EGFR blockade by tyrosine kinase inhibitor or monoclonal antibody inhibits growth, directs terminal differentiation and induces apoptosis in the human squamous cell carcinoma HN5." *Int. J. Oncol.* (1998) 335-342, 13(2).
Modjtahedi et al., "Phase I trial and tumour localisation of the anti-EGFR monoclonal antibody ICR62 in head and neck or lung cancer." *British Journal of Cancer* (1996) 228-235, 73(2).
Modjtahedi et al., "Differentiation or immune destruction: two pathways for therapy of squamous cell carcinomas with antibodies to the epidermal growth factor receptor." *Cancer Res.* (1994) 1695-1701, 54(7).
Modjtahedi et al., "The receptor for EGF and its ligands—expression, prognostic value and target for therapy in cancer (review)." *Int. J. Oncol.* (1994) 277-296, 4(2).
Modjtahedi et al., "Immunotherapy of human tumour xenografts overexpressing the EGF receptor with rat antibodies that block growth factor-receptor interaction." *British Journal of Cancer* (1993) 254-261, 67(2).
Modjtahedi et al., "The human EGF receptor as a target for cancer therapy: six new rat mAbs against the receptor on the breast carcinoma MDA-MB 468." *British Journal of Cancer* (1993) 247-253, 67(2).
Modjtahedi et al., "Targeting of cells expressing wild-type EGFR and type-III mutant EGFR (EGFRvIII) by anti-EGFR MAb ICR62: a two-pronged attack for tumour therapy." *Int. J. Cancer* (2003) 273-280, 105(2).
Moghal et al., "Multiple positive and negative regulators of signaling by the EGF-receptor." *Current Opinion in Cell Biology* (1999) 190-196, 11(2).
Montgomery et al., "Expression of oncogenic epidermal growth factor receptor family kinases induces paclitaxel resistance and alters beta-tubulin isotype expression." *Journal of Biological Chemistry* (2000) 17358-17363, 275(23).
Morales et al., "Humanized versus murine anti-human epidermal growth factor receptor monoclonal antibodies for immunoscintigraphic studies." *Nucl. Med. Biol.* (2000) 199-206, 27(2).
Morea et al., "Antibody structure, prediction and redesign." *Biophysical Chemistry* (1997) 9-16, 68(1-3).
Moriki et al., "Activation of preformed EGF receptor dimers by ligand-induced rotation of the transmembrane domain." *J. Mol. Biol.* (2001) 1011-1026, 311(5).

(56) References Cited

OTHER PUBLICATIONS

Moroni et al., "Gene copy number for epidermal growth factor receptor (EGFR) and clinical response to antiEGFR treatment in colorectal cancer: a cohort study." *The Lancet Oncology* (2005) 279-286, 6(5).
Morrison et al., "Recombinant chimeric monoclonal antibodies." *Important advances in oncology* (1990) 3-18.
Moscatello et al., "Constitutive activation of phosphatidylinositol 3-kinase by a naturally occurring mutant epidermal growth factor receptor." *JBC* (1998) 200-206, 273(1).
Moscatello et al., "A naturally occuring mutant human epidermal growth factor receptor as a target for peptide vaccine immunotherapy of tumors." *Cancer Res.* (1997) 1419-1424, 57(8).
Moscatello et al., "Transformational and altered signal transduction by a naturally occurring mutant EGF receptor." *Oncogene* (1996) 85-96, 13(1).
Moscatello et al., "Frequent expression of a mutant epidermal growth factor receptor in multiple human tumors." *Cancer Res.* (1995) 5536-5539, 55(23).
Motoyama et al., "The efficacy of ErbB receptor-targeted anticancer therapeutics is influenced by the availability of epidermal growth factor-related peptides." *Cancer Res.* (2002) 3151-3158, 62(11).
Moulder et al., "Epidermal growth factor receptor (HER1) tyrosine kinase inhibitor ZD1839 (Iressa) inhibits HER2/neu (erbB2)-overexpressing breast cancer cells in vitro and in vivo." *Cancer Res.* (2001) 8887-8895, 61(24).
Moyer et al., "Induction of apoptosis and cell cycle arrest by CP-358,774, an inhibitor of epidermal growth factor receptor tyrosine kinase." *Cancer Res.* (1997) 4838-4848, 57(21).
Murshudov et al., "Refinement of macromolecular structures by the maximum-likelihood likelihood method." *Acta Crystallogr. D. Biol. Crystallogr.* (1997) 240-255, 53(Pt 3).
Murthy et al., "Binding of an antagonistic monoclonal antibody to an intact and fragmented EGF-receptor polypeptide." *Archives of biochemistry and biophysics* (1987) 549-560, 252(2).
Muthuswamy et al., "Controlled dimerization of ErbB receptors provides evidence for differential signaling by homo- and heterodimers." *Mol. Cell Biol.* (1999) 6845-6857, 19(10).
Nagane et al., "Human glioblastoma xenografts overexpressing a tumor-specific mutant epidermal growth factor receptor sensitized to cisplatin by the AG1478 tyrosine kinase inhibitor." *J. Neurosurg.* (2001) 472-479, 95(3).
Nagane et al., "Aberrant receptor signaling in human malignant gliomas: mechanisms and therapeutic implications." *Cancer Letters* (2001) S17—S21, 162 Suppl.
Nagane et al., "Drug resistance of human glioblastoma cells conferred by a tumor-specific mutant epidermal growth factor receptor through modulation of Bcl-XL and caspase-3-like proteases." *Proceedings of the National Academy of Sciences of the United States of America* (1998) 5724-5729, 95(10).
Nagane et al., "A common mutant epidermal growth factor receptor confers enhanced tumorigenicity on human glioblastoma cells by increasing proliferation and reducing apoptosis." *Cancer Res.* (1996) 5079-5086, 56(21).
Nair et al., "Crystal structure of an antibody bound to an immunodominant peptide epitope: novel features in peptide-antibody recognition." *Journal of immunology* (Bethesda, MD : 1950) (2000) 6949-6955, 165(12).
Nakagawa et al., "A Phase I Intermittent Dose-Escalation Trial of ZD1939 (Iressa) in Japanese Patients with Solid malignant tumours." *Proceedings of the American Society of Clinical Oncology* (2000) 183 (Abstract 711), 19.
Naramura et al., "Therapeutic potential of chimeric and murine anti-(epidermal growth factor receptor) antibodies in a metastasis model for human melanoma." *Cancer Immunol. Immunother.* (1993) 343-349, 37(5).
Narita et al., "Mutant epidermal growth factor receptor signaling down-regulates p27 through activation of the phosphatidylinositol 3-kinase/Akt pathway in glioblastomas." *Cancer Res.* (2002) 6764-6769, 62(22).

Natale et al., "ZD1839 (Iressa): what's in it for the patient?" *Oncologist* (2002) 25-30, 7(Suppl. 4).
Neal et al., "The epidermal growth factor receptor and the prognosis of bladder cancer." *Cancer* (1990) 1619-1625, 65(7).
Neal et al., "Epidermal-growth-factor receptors in human bladder cancer: comparison of invasive and superficial tumours." *Lancet* (1985) 366-368, 1(8425).
Negri et al., "In vitro and in vivo stability and anti-tumour efficacy of an anti-EGFR/anti-CD3 F(ab')2 bispecific monoclonal antibody." *British Journal of Cancer* (1995) 928-933, 72(4).
Neidhardt et al., "Culture medium for enterobacteria." *Journal of bacteriology* (1974) 736-747, 119(3).
Nice et al., "Instrumental biosensors: new perspectives for the analysis of biomolecular interactions." *BioEssays : news and reviews in molecular, cellular and developmental biology* (1999) 339-352, 21(4).
Nicholson et al., "EGFR and cancer prognosis." *Eur. J. Cancer* (2001) S9-15, 37 Suppl 4.
Nikura et al., "Expression of epidermal growth factor-related proteins and epidermal growth factor receptor in common epithelial ovarian tumors." *International journal of gynecological pathology : official journal of the International Society of Gynecological Pathologists* (1997) 60-68, 16(1).
Nishikawa et al., "A mutant epidermal growth factor receptor common in human glioma confers enhanced tumorigenicity." *Proceedings of the National Academy of Sciences of the United States of America* (1994) 7727-7731, 91(16).
Nishikawa et al., "Immunohistochemical analysis of the mutant epidermal growth factor, ΔEGFR, in glioblastoma." *Brain tumor pathology* (2004) 53-56, 21(2).
Noonberg et al., "Tyrosine kinase inhibitors targeted to the epidermal growth factor receptor subfamily: role as anticancer agents." *Drugs* (2000) 753-767, 59(4).
Normanno et al., "Cooperative inhibitory effect of ZD1839 (Iressa) in combination with trastuzumab (Herceptin) on human breast cancer cell growth." *Ann. Oncol.* (2002) 65-72, 13(1).
Normanno et al., "Growth inhibition of human colon carcinoma cells by combinations of anti-epidermal growth factor-related growth factor antisense oligonucleotides." *Clin. Cancer Res.* (1996) 601-609, 2(3).
Normanno et al., "Epidermal growth factor receptor (EGFR) signaling in cancer." *Gene* (2006) 2-16, 366(1).
Norton et al., "Overall survival (OS) advantage to simultaneous chemotherapy (CRx) plus the humanized anti-HER2 monoclonal antibody Herceptin (H) in HER2-overexpressing (HER2+) metastatic breast cancer (MBC)." *Proceedings of the American Society of Clinical Oncology* (1999) 127a (Abstract 483), 18.
O-Charoenrat et al., "Overexpression of epidermal growth factor receptor in human head and neck squamous carcinoma cell lines correlates with matrix metalloproteinase-9 expression and in vitro invasion." *Int. J. Cancer* (2000) 307-317, 86(3).
O-Charoenrat et al., "Vascular endothelial growth factor family members are differentially regulated by c-erbB signaling in head and neck squamous carcinoma cells." *Clinical & experimental metastasis* (2000) 155-161, 18(2).
O-Charoenrat et al., "The role of c-erbB receptors and ligands in head and neck squamous cell carcinoma." *Oral oncology* (2002) 627-640, 38(7).
Ochiai et al., "EGFRvIII-targeted immunotoxin induces antitumor immunity that is inhibited in the absence of CD4+ and CD8+ T cells." *Cancer Immunol. Immunother.* (2008) 115-121, 57(1).
Oflazoglu et al., "Potent Anticarcinoma Activity of the Humanized Anti-CD70 Antibody h1F6 Conjugated to the Tubulin Inhibitor Auristatin via an Uncleavable Linker" *Clinical Cancer Research* (2008) 6171-6180, 14(19).
Ogiso et al., "Crystal structure of the complex of human epidermal growth factor and receptor extracellular domains." *Cell* (2002) 775-787, 110(6).
Ohman et al., "A new antibody recognizing the vIII mutation of human epidermal growth factor receptor." *Tumour biology : the journal of the International Society for Oncodevelopmental Biology and Medicine* (2002) 61-69, 23(2).

(56) References Cited

OTHER PUBLICATIONS

Okamoto et al., "Expression of constitutively activated EGFRvIII in non-small cell lung cancer." *Cancer Science* (2003) 50-56, 94(1).

Olapade-Olaopa et al., "Evidence for the differential expression of a variant EGF receptor protein in human prostate cancer." *British Journal of Cancer* (2000) 186-194, 82(1).

Olayioye et al., "The ErbB signaling network: receptor heterodimerization in development and cancer." *EMBO J.* (2000) 3159-3167, 19(13).

Olayioye et al., "ErbB-1 and ErbB-2 acquire distinct signaling properties dependent upon their dimerization partner." *Mol. Cell Biol.* (1998) 5042-5051, 18(9).

Old, "Immunotherapy for cancer." *Sci. Am.* (1996) 136-143, 275(3).

Olson et al., "Transmodulation of epidermal growth factor binding by platelet-derived growth factor and 12-O-tetradecanoylphorbol-13-acetate is not sodium-dependent in Balb/c/3T3 cells." *JBC* (1990) 1847-1851, 265(4).

Omidfar et al., "Production of a novel camel single-domain antibody specific for the type III mutant EGFR." *Tumor biology : the journal of the International Society for Oncodevelopmental Biology and Medicine* (2004) 296-305, 25(5-6).

Omidfar et al., "Production and characterizastion of a new antibody specific for the mutant EGF receptor, EGFRvIII, in *Camelus bactrianus.*" *Tumor biology : the journal of the International Society for Oncodevelopmental Biology and Medicine* (2004) 179-187, 25(4).

Opresko et al., "Endocytosis and lysosomal targeting of epidermal growth factor receptors are mediated by distinct sequences independent of the tyrosine kinase domain." *JBC* (1995) 4325-4333, 270(9).

Orntoft et al., "Clinical aspects of altered glycosylation of glycoproteins in cancer." *Electrophoresis* (1999) 362-371, 20(2).

Osband et al., "Problems in the investigational study and clinical use of cancer immunotherapy." *Immunology Today* (1990) 193-195, 11(6).

Ostermann et al., "Effective Immunoconjugate Therapy in Cancer Models Targeting a Serine Protease of Tumor Fibroblasts" *Clinical Cancer Research* (2008) 4584-4592, 14(14).

Otwinowski et al., "Processing of X-ray diffraction data collected in oscillation mode" *Methods in Enzymology* (1997) 307-326, 276.

Overdijk et al., "Role of ADCC in the in vivo antitumor effects of zalutumumab, a human anti-EGF receptor antibody" *ASCO Meeting* (2010).

Overholser et al., "Epidermal growth factor receptor blockade by antibody IMC-C225 inhibits growth of a human pancreatic carcinoma xenograft in nude mice." *Cancer* (2000) 74-82, 89(1).

Owens et al., "The genetic engineering of monoclonal antibodies." *J. Immunol. Methods* (1994) 149-165, 168(2).

Ozanne et al., "Over-expression of the EGF receptor is a hallmark of squamous cell carcinomas." *The Journal of Pathology* (1986) 9-14, 149(1).

Ozawa et al., "Prognostic significance of epidermal growth factor receptor in esophageal squamous cell carcinomas." *Cancer* (1989) 2169-2173, 63(11).

Padlan et al., "Identification of specificity-determining residues in antibodies." *FASEB J.* (1995) 133-139, 9(1).

Padlan, "Anatomy of the antibody molecule." *Mol. Immunol.* (1994) 169-217, 31(3).

Padlan, "A possible procedure for reducing the immunogenicity of antibody variable domains while preserving their ligand-binding properties." *Mol. Immunol.* (1991) 489-498, 28(4-5).

Padlan, "On the nature of antibody combining sites: unusual structural features that may confer on these sites an enhanced capacity for binding ligands." *Proteins* (1990) 112-124, 7(2).

Paganelli et al., "Antibody-guided three-step therapy for high grade glioma with yttrium-90 biotin." *European Journal of Nuclear Medicine* (1999) 348-357, 26(4).

Pai et al., "The use of immunotoxins for cancer therapy." *Eur. J. Cancer* (1993) 1606-1609, 29A(11).

Pai et al., "Prostaglandin E2 transactivates EGF receptor: a novel mechanism for promoting colon cancer growth and gastrointestinal hypertrophy." *Nature Med.* (2002) 289-293, 8(3).

Palacios et al., "Interleukin-3 supports growth of mouse pre-B-cell clones in vitro." *Nature* (1984) 126-131, 309(5964).

Pao et al., "Epidermal growth factor receptor mutations, small-molecule kinase inhibitors, and non-small-cell lung cancer: current knowledge and future directions." *J. Clin. Oncol.* (2005) 2556-2568, 23(11).

Pao et al., "Acquired resistance of lung adenocarcinomas to gefitinib or erlotinib is associated with a second mutation in the EGFR kinase domain." *PLoS Medicine* (2005) e73, 2(3).

Pao et al., "KRAS mutations and primary resistance of lung adenocarcinomas to gefitinib or erlotinib." *PLoS Medicine* (2005) e17, 2(1).

Parker et al., "Preferential activation of the epidermal growth factor receptor in human colon carcinoma liver metastases in nude mice." *The Journal of Histochemistry and Cytochemistry : Official Journal of the Histochemistry Society* (1998) 595-602, 46(5).

De Pascalis et al., "Grafting of 'abbreviated' complementarity-determining regions containing specificity-determining residues essential for ligand contact to engineer a less immunogenic humanized monoclonal antibody." *Journal of immunology* (Baltimore, Md : 1950) (2002) 3076-3084, 169(6).

Pastan, "Targeted therapy of cancer with recombinant immunotoxins." *Biochimica et Biophysica Acta* (1997) C1-6, 1333(2).

Patel et al., "Monoclonal antibody cetuximab binds to and down-regulates constitutively activated epidermal growth factor receptor vIII on the cell surface." *Anticancer research* (2007) 3355-3366, 27(5A).

Pavelic et al., "Evidence for a role of EGF receptor in the progression of human lung carcinoma." *Anticancer Research* (1993) 1133-1137, 13(4).

Pawson et al., "SH2 and SH3 domains." *Current Biology* (1993) 434-442, 3(7).

Pawson, "Protein modules and signalling networks." *Nature* (1995) 573-580, 373.

Pedersen et al., "The type III epidermal growth factor receptor mutation. Biological significance and potential target for anti-cancer therapy." *Ann Oncol.* (2001) 745-760, 12(6).

Pedersen et al., "Analysis of the epidermal growth factor receptor specific transcriptome: effect of receptor expression level and an activating mutation." *J. Cell Biochem.* (2005) 412-427, 96(2).

Pegram et al., "Antibody dependent cell-mediated cytotoxicity in breast cancer patients in Phase III clinical trials of a humanized anti-HER2 antibody." *Proceedings of the Annual Meeting of the American Association for Cancer Research* (1997) 602 (Abstract 4044), 39.

Pegram et al., "Inhibitory effects of combinations of HER-2/neu antibody and chemotherapeutic agents used for treatment of human breast cancers." *Oncogene* (1999) 2241-2251, 18(13).

Pegram et al., "Phase II study of receptor-enhanced chemosensitivity using recombinant humanized anti-p185HER2/neu monoclonal antibody plus cisplatin in patients with HER2/neu-overexpressing metastatic breast cancer refractory to chemotherapy treatment." *J. Clin. Oncol.* (1998) 2659-2671, 16(8).

Pegram et al., "The effect of HER-2/neu overexpression on chemotherapeutic drug sensitivity in human breast and ovarian cancer cells." *Oncogene* (1997) 537-547, 15(5).

Pegram et al., "Rational combinations of trastuzumab with chemotherapeutic drugs used in the treatment of breast cancer." *J. Natl. Cancer Inst.* (2004) 739-749, 96(10).

Pelloski et al., "Epidermal growth factor receptor variant III status defines clinically distinct subtypes of glioblastoma." *Journal of Clinical Oncology* (2007) 2288-2294, 25(16).

Peng et al., "Anti-epidermal growth factor receptor monoclonal antibody 225 up-regulates p27KIP1 and induces G1 arrest in prostatic cancer cell line DU145." *Cancer Res.* (1996) 3666-3669, 56(16).

Perera et al., "Internalisation and Trafficking of the Monoclonal Antibody 806 Reactive Epidermal Growth Factor Receptor." *Austin Health Research Week*, Austin Hospital, Melbourne, Australia (2003) Abstract 112.

(56) References Cited

OTHER PUBLICATIONS

Perera et al., "The Influence of Epidermal Growth Factor Receptor (EGFR) Number and Activation on the Efficacy of Antibodies Directed to the Receptor." *Proceedings of the 14th Annual Lorne Cancer Conference*, Lorne, Victoria, Australia (2002) Abstract 216.

Perera et al., "Requirement for the von Hippel-Lindau tumor suppressor gene for functional epidermal growth factor receptor blockade by monoclonal antibody C225 in renal cell carcinoma." *Clin. Cancer Res.* (2000) 1518-1523, 6(4).

Perera, "Therapeutic Efficacy and Intracellular Trafficking of Anti-Epidermal Growth Factor Receptor Antibodies (PhD Thesis)" *Submitted in Total Fulfilment of the Requirements for the Degree of Doctor of Philosophy*, University of Melbourne. (2004) 1-239.

Perera et al., "Internalization, intracellular trafficking, and biodistribution of monoclonal antibody 806: a novel anti-epidermal growth factor receptor antibody." *Neoplasia* (2007) 1099-1110, 9(12).

Perera et al., "Treatment of human tumor xenografts with monoclonal antibody 806 in combination with a prototypical epidermal growth factor receptor-specific antibody generates enhanced antitumor activity." *Clin. Cancer Res.* (2005) 6390-6399, 11(17).

Perez-Soler et al., "A phase II trial of the epidermal growth factor receptor (EGFR) tyrosine kinase inhibitor OSI-774, following platinum-based chemotherapy in patients (pts) with advanced EGFR-expressing, non-small cell lung cancer (NSCLC)." *Proceedings of the American Society of Clinical Oncology* (2001) 310a (Abstract 1235), 20.

Perez-Soler et al., "Tumor Studies in Patients With Head & Neck Cancer Treated With Humanized Anti-Epidermal Growth Factor (EGFR) Monoclonal Antibdoy C225 in Combination With Cisplatin." *Proceedings of the American Society of Clinical Oncology* (1998) 393a (Abstract 1514), 17.

Perez-Soler et al., "Tumor epidermal growth factor receptor studies in patients with non-small-cell lung cancer or head and neck cancer treated with monoclonal antibody RG 83852." *J. Clin. Oncol.* (1994) 730-739, 12(4).

Pérez-Soler, "HER1/EGFR targeting: refining the strategy." *Oncologist* (2004) 58-67, 9(1).

Perrotte et al., "Anti-epidermal growth factor receptor antibody C225 inhibits angiogenesis in human transitional cell carcinoma growing orthotopically in nude mice." *Clin. Cancer Res.* (1999) 257-265, 5(2).

Petit et al., "Neutralizing antibodies against epidermal growth factor and ErbB-2/neu receptor tyrosine kinases down-regulate vascular endothelial growth factor production by tumor cells in vitro and in vivo: angiogenic implications for signal transduction therapy of solid tumors." *The American Journal of Pathology* (1997) 1523-1530, 151(6).

Petrides et al., "Modulation of pro-epidermal growth factor, pro-transforming growth factor alpha and epidermal growth factor receptor gene expression in human renal carcinomas." *Cancer Res.* (1990) 3934-3939, 50(13).

Pfister et al., "A phase I trial of the epidermal growth factor receptor (EGFR)-directed bispecific antibody (BsAB) MDX-447 in patients with solid tumors." *Proceedings of the American Society of Clinical Oncology* (1999) 433a (Abstract 1667), 18.

Pfosser et al., "Role of target antigen in bispecific-antibody-mediated killing of human glioblastoma cells: a pre-clinical study." *Int. J. Cancer* (1999) 612-616, 80(4).

Pfreundschuh et al., "Serological analysis of cell surface antigens of malignant human brain tumors." *Proceedings of the National Academy of Sciences of the United States of America* (1978) 5122-5126, 75(10).

Pietras et al., "Monoclonal antibody to HER-2/neureceptor modulates repair of radiation-induced DNA damage and enhances radiosensitivity of human breast cancer cells overexpressing this oncogene." *Cancer Res.* (1999) 1347-1355, 59(6).

Pietras et al., "Remission of human breast cancer xenografts on therapy with humanized monoclonal antibody to HER-2 receptor and DNA-reactive drugs." *Oncogene* (1998) 2235-2249, 17(17).

Pillay et al., "The plasticity of oncogene addiction: implications for targeted therapies directed to receptor tyrosine kinases." *Neoplasia* (2009) 448-458, 11(5).

Pontén et al., "Long term culture of normal and neoplastic human glia." *Acta pathologica et microbiologica Scandinavica* (1968) 465-486, 74(4).

Power et al., "Construction, expression and characterisation of a single-chain diabody derived from a humanised anti-Lewis Y cancer targeting antibody using a heat-inducible bacterial secretion vector." *Cancer Immunol. Immunother.* (2001) 241-250, 50(5).

Power et al., "Noncovalent scFv multimers of tumor-targeting anti-Lewis(y) hu3S193 humanized antibody." *Protein Science* (2003) 734-747, 12(4).

Prados et al., "Biology and treatment of malignant glioma." *Semin. Oncol.* (2000) 1-10, 27(3; Suppl. 6).

Prenzel et al., "The epidermal growth factor receptor family as a central element for cellular signal transduction and diversification." *Endocrine-Related Cancer* (2001) 11-31, 8(1).

Press et al., "Inhibition of catabolism of radiolabeled antibodies by tumor cells using lysosomotropic amines and carboxylic ionophores." *Cancer Res.* (1990) 1243-1250, 50(4).

Press et al., "Ricin A-chain containing immunotoxins directed against different epitopes on the CD2 molecule differ in their ability to kill normal and malignant T cells." *Journal of immunology* (1950) (1988) 4410-4417, 141(12).

Presta et al., "Humanization of an anti-vascular endothelial growth factor monoclonal antibody for the therapy of solid tumors and other disorders." *Cancer Res.* (1997) 4593-4599, 57(20).

Presta et al., "Humanization of an antibody diorected against IgE." *Journal of immunology* (Baltimore, Md : 1950) (1993) 2623-2632, 151(5).

Presta, "Molecular engineering and design of therapeutic antibodies." *Curr. Opin. Immunol.* (2008) 460-470, 20(4).

Presta, "Engineering of therapeutic antibodies to minimize immunogenicity and optimize function." *Advanced drug delivery reviews* (2006) 640-656, 58(5-6).

Prewett et al., "Mouse-human chimeric anti-epidermal growth factor receptor antibody C225 inhibits the growth of human renal cell carcinoma xenografts in nude mice." *Clin. Cancer Res.* (1998) 2957-2966, 4(12).

Prewett et al., "The biologic effects of C225, a chimeric monoclonal antibody to the EGFR, on human prostate carcinoma." *Journal of Immunotherapy with Emphasis on Tumor Immunology : Official Journal of the Society for Biological Therapy* (1996) 419-427, 19(6).

Prewett et al., "Anti-tumor and cell cycle responses in KB cells treated with a chimeric anti-EGFR monoclonal antibody in combination with cisplatin." *Int. J. Oncol.* (1996) 217-224, 9(2).

Prewett et al., "Enhanced antitumor activity of anti-epidermal growth factor receptor monoclonal antibody IMC-C225 in combination with irinotecan (CPT-11) against human colorectal tumor xenografts." *Clin. Cancer Res.* (2002) 994-1003, 8(5).

Prigent et al., "Enhanced tumorigenic behavior of glioblastoma cells expressing a truncated epidermal growth factor receptor is mediated through the Ras-Shc-Grb2 pathway." *Journal of Biological Chemistry* (1996) 25639-25645, 271(41).

Prigent et al., "The type 1 (EGFR-related) family of growth factor receptors and their ligands." *Progress in growth factor research* (1992) 1-24, 4(1).

Privalsky et al., "The membrane glycoprotein encoded by the retroviral oncogene v-erb-B is structurally related to tyrosine-specific protein kinases." *Proceedings of the National Academy of Sciences of the United States of America* (1984) 704-707, 81(3).

Pruss et al., "Variants of 3T3 cells lacking mitogenic response to epidermal growth factor." *Proceedings of the National Academy of Sciences of the United States of America* (1977) 3918-3921, 74(9).

Pütz et al., "Functional fine-mapping and molecular modeling of a conserved loop epitope of the measles virus hemagglutinin protein." *Eur. J. Biochem.* (2003) 1515-1527, 270(7).

Raben et al., "C225 anti-EGFR antibody potentiates radiation (RT) and chemotherapy (CT) cytotoxicity in human non-small cell lung cancer (NSCLC) cells in vitro and in vivo." *Proceedings of the American Society of Clinical Oncology* (2001) 257a (Abstract 1026), 20.

(56) References Cited

OTHER PUBLICATIONS

Raben et al., "Treatment of human intracranial gliomas with chimeric monoclonal antibody against the epidermal growth factor receptor increases survival of nude mice when treated concurrently with irradiation." *Proceedings of the American Association for Cancer Research* (1999) 184 (Abstract 1224), 40.
Raben et al., "ZD1839, a selective epidermal growth factor receptor tyrosine kinase inhibitor, alone and in combination with radiation and chemotherapy as a new therapeutic strategy in non-small cell lung cancer." *Semin. Oncol.* (2002) 37-46, 29(1; Suppl. 4).
Radinsky et al., "Level and function of epidermal growth factor receptor predict the metastatic potential of human colon carcinoma cells." *Clin. Cancer Res.* (1995) 19-31, 1(1).
Raizer, "HER1/EGFR tyrosine kinase inhibitors for the treatment of glioblastoma multiforme." *Journal of neuro-oncology* (2005) 77-86, 74(1).
Rakowicz-Szulczynska et al., "Epidermal growth factor (EGF) and monoclonal antibody to cell surface EGF receptor bind to the same chromatin receptor." *Archives of Biochemistry and Biophysics* (1989) 456-464, 268(2).
Ramnarain et al., "Differential gene expression analysis reveals generation of an autocrine loop by a mutant epidermal growth factor receptor in glioma cells." *Cancer Res.* (2006) 867-874, 66(2).
Ramos et al., "Treatment of high-grade glioma patients with the humanized anti-epidermal growth factor receptor (EGFR) antibody h-R3: report from a phase I/II trial." *Cancer biology & therapy* (2006) 375-379, 5(4).
Ramos-Suzarte et al., "99mTc-labeled antihuman epidermal growth factor receptor antibody in patients with tumors of epithelial origin: Part III. Clinical trials safety and diagnostic efficacy." *J. Nucl. Med.* (1999) 768-775, 40(5).
Ramsland et al., "Structural convergence of antibody binding of carbohydrate determinants in Lewis Y tumor antigens." *J. Mol. Biol.* (2004) 809-818, 340(4).
Ranson, "ZD1839 (Iressa): for more than just non-small cell lung cancer." *Oncologist* (2002) 16-24, 7(Suppl. 4).
Rao et al., "Radiosensitization of human breast cancer cells by a novel ErbB family receptor tyrosine kinase inhibitor." *Int. J. Radiat. Oncol. Biol. Phys.* (2000) 1519-1528, 48(5).
Raymond et al., "General method for plasmid construction using homologous recombination." *BioTechniques* (1999) 134-8, 140-1, 26(1).
Rayzman et al., "Monoclonal antibodies for cancer therapy." *Cancer Forum* (2002) 104-108, 26(2).
Reardon et al., "Recent advances in the treatment of malignant astrocytoma." *Journal of Clinical Oncology* (2006) 1253-1265, 24(8).
Reed, "Dysregulation of apoptosis in cancer." *J. Clin. Oncol.* (1999) 2941-2953, 17(9).
Reese et al., "Effects of the 4D5 antibody on HER2/neu heterodimerization with other class I receptors in human breast cancer cells." *Proceedings of the Annual Meeting of the American Association for Cancer Research* (1996) 51 (Abstract 353), 37.
Van Regenmortel et al., "Comparative immunological methods." *Methods in Enzymology* (1993) 130-140, 224.
Reilly et al., "A comparison of EGF and MAb 528 labeled with 111In for imaging human breast cancer." *J. Nucl. Med.* (2000) 903-911, 41(5).
Reiss et al., "Activation of the autocrine transforming growth factor alpha pathway in human squamous carcinoma cells." *Cancer Res.* (1991) 6254-6262, 51(23; Part 1).
Reist et al., "Astatine-211 labeling of internalizing anti-EGFRvIII monoclonal antibody using N-succinimidyl 5-[211At]astato-3-pyridinecarboxylate." *Nucl. Med. Biol.* (1999) 405-411, 26(4).
Reist et al., "In vitro and in vivo behavior of radiolabeled chimeric anti-EGFRvIII monoclonal antibody: comparison with its murine parent." *Nucl. Med. Biol.* (1997) 639-647, 24(7).
Reist et al., "Radioiodination of internalizing monoclonal antibodies using N-succinimidyl 5-iodo-3-pyridinecarboxylate." *Cancer Res.* (1996) 4970-4977, 56(21).
Reiter et al., "Comparative genomic sequence analysis and isolation of human and mouse alternative EGFR transcripts encoding truncated receptor isoforms." *Genomics* (2001) 1-20, 71(1).
Rettig et al., "Immunogenetics of human cell surface differentiation." *Annual review of immunology* (1989) 481-511, 7.
Reynolds et al., "Human transforming growth factors induce tyrosine phosphorylation of EGF receptors." *Nature* (1981) 259-262, 292(5820).
Ribas et al., "Systemic delivery of siRNA via targeted nanoparticles in patients with cancer: Results from a first-in-class phase I clinical trial" *J. Clin. Oncol.* (2010) Abstract 3022, 38(15S).
Riemer et al., "Mimotope vaccines: epitope mimics induce anti-cancer antibodies." *Immunology letters* (2007) 1-5, 113(1).
Riemer et al., "Vaccination with cetuximab mimotopes and biological properties of induced anti-epidermal growth factor receptor antibodies." *J. Natl. Cancer Inst.* (2005) 1663-1670, 97(22).
Riemer et al., "Matching of trastuzumab (Herceptin) epitope mimics onto the surface of Her-2/neu—a new method of epitope definition." *Mol. Immunol.* (2005) 1121-1124, 42(9).
Riese et al., "Specificity within the EGF family/ErbB receptor family signaling network." *BioEssays : news and reviews in molecular, cellular and developmental biology* (1998) 41-48, 20(1).
Rieske et al., "A comparative study of epidermal growth factor receptor (EGFR) and MDM2 gene amplification and protein immunoreactivity in human glioblastomas." *Polish Journal of Pathology : Official Journal of the Polish Society of Pathologists* (1998) 145-149, 49(3).
Rinehart et al., "A phase 1 clinical and pharmacokinetic study of oral CI-1033, a pan-erbB tyrosine kinase inhibitor in patients with advanced solid tumors." *Proceedings of the American Society of Clinical Oncology* (2002) 11a (Abstract 41), 21.
Ringerike et al., "High-affinity binding of epidermal growth factor (EGF) to EGF receptor is disrupted by overexpression of mutant dynamin (K44A)." *JBC* (1998) 16639-16642, 273(27).
Ritter et al., "Serological analysis of human anti-human antibody responses in colon cancer patients treated with repeated doses of humanized monoclonal antibody A33." *Cancer Res.* (2001) 6851-6859, 61(18).
Riva et al., "Role of nuclear medicine in the treatment of malignant gliomas: the locoregional radioimmunotherapy approach." *European Journal of Nuclear Medicine* (2000) 601-609, 27(5).
Rivera et al., "Current situation of Panitumumab, Matuzumab, Nimotuzumab and Zalutumumab." *Acta oncologica* (Stockholm, Sweden) (2008) 9-19, 47(1).
Ro et al., "Amplified and overexpressed epidermal growth factor receptor gene in uncultured primary human breast carcinoma." *Cancer Res.* (1988) 161-164, 48(1).
Robert et al., "Phase I study of anti-epidermal growth factor receptor antibody cetuximab in combination with radiation therapy in patients with advanced head and neck cancer." *J. Clin. Oncol.* (2001) 3234-3243, 19(13).
Rocha-Lima et al., "EGFR targeting of solid tumors." *Cancer control : journal of the Moffitt Cancer Center* (2007) 295-304, 14(3).
Rodeck et al., "Monoclonal antibody 425 inhibits growth stimulation of carcinoma cells by exogenous EGF and tumor-derived EGF/TGF-alpha." *J. Cell Biochem.* (1990) 69-79, 44(2).
Rodeck et al., "Interactions between growth factor receptors and corresponding monoclonal antibodies in human tumors." *J. Cell Biochem.* (1987) 315-320, 35(4).
Rodeck et al., "Tumor growth modulation by a monoclonal antibody to the epidermal growth factor receptor: immunologically mediated and effector cell-independent effects." *Cancer Res.* (1987) 3692-3696, 47(14).
Roepstorff et al., "Sequestration of epidermal growth factor receptors in noncaveolar lipid rafts inhibits ligand binding." *JBC* (2002) 18954-18960, 277(21).
Roguska et al., "A comparison of two murine monoclonal antibodies humanized by CDR-grafting and variable domain resurfacing." *Protein Engineering* (1996) 895-904, 9(10).
Roguska et al., "Humanization of murine monoclonal antibodies through variable domain resurfacing." *Proceedings of the National Academy of Sciences of the United States of America* (1994) 969-973, 91(3).

(56) References Cited

OTHER PUBLICATIONS

Rosell et al., "Randomized phase II study of cetuximab in combination with cisplatin (C) and vinorelbine (V) vs. CV alone in the first-line treatment of patients (pts) with epidermal growth factor receptor (EGFR)-expressing advanced non-small-cell lung cancer (NSCLC)" *Journal of Clinical Oncology*, 2004 ASCO Annual Meeting Proceedings (Post-Meeting Edition) (2004) Abstract 7012, 22(14S; Jul. 15 Supplement).

Rosell et al., "Randomized phase II study of cetuximab in combination with cisplatin (C) and vinorelbine (V) vs. CV alone in the first-line treatment of patients (pts) with epidermal growth factor receptor (EGFR)-expressing advanced non-small-cell lung cancer (NSCLC)." *Proceedings of the American Society of Clinical Oncology* (2004) 620s (Abstract 7012), 23.

Rosenberg et al., "Erbitux (IMC-225) plus weekly irinotecan (CPT-11), fluorouricil (5FU) and leucovorin (LV) in colorectal cancer (CRC) that expresses the epidermal growth factor receptor (EGFR)." *Proceedings of the American Society of Clinical Oncology* (2002) 135a (Abstract 536), 21.

Ross et al. "Anticancer antibodies." *American Journal of Clinical Pathology* (2003) 472-485, 119(4).

Rothacker, "Ligand binding induces a conformational change in the untethered epidermal growth factor receptor" *Ludwig Institute for Cancer Research* (2010).

Rougier et al., "Cetuximab + FOLFIRI as first-line treatment for metastatic colorectal CA." *Proceedings of the Annual Meeting of the American Society of Clinical Oncology* (2004) 248s (Abstract 3513), 22.

Rowinsky et al., "Safety, pharmacokinetics, and activity of ABX-EGF, a fully human anti-epidermal growth factor receptor monoclonal antibody in patients with metastatic renal cell cancer." *J. Clin. Oncol.* (2004) 3003-3015, 22(15).

Rubin et al., "Monoclonal Antibody (MoAb) IMC-C225, an Anti-Epidermal Growth Factor Receptor (EGFr), for Patients (Pts) with EGFr-Positive Tumors Refractory to or in Relapse from Previous Therapeutic Regimens" *Proc. Am. Soc. Clin. Oncol.* (2000) Abstract 1860, 19.

Rubin et al., "Monoclonal antibody (MoAb) IMC-C225, an anti-epidermal growth factor receptor (EGFR), for patients with EGFR-positive tumors refractory to or in relapse from previous therapeutic regimens." *Proceedings of the American Society of Clinical Oncology* (2000) 474a (Abstract 1860), 193.

Rubin Grandis et al., "Inhibition of epidermal growth factor receptor gene expression and function decreases proliferation of head and neck squamous carcinoma but not normal mucosal epithelial cells." *Oncogene* (1997) 409-416, 15(4).

Rubin Grandis et al., "Quantitative immunohistochemical analysis of transforming growth factor-alpha and epidermal growth factor receptor in patients with squamous cell carcinoma of the head and neck." *Cancer* (1996) 1284-1292, 78(6).

Rubio et al., "Cetuximab in combination with oxaliplatin/5-fluorouracil (5-FU)/folinic acid (FA) (FOLFOX-4) in the first-line treatment of patients with epidermal growth factor receptor (EGFR)-expressing metastatic colorectal cancer: an international phase II study." *Journal of Clinical Oncology*, 2005 ASCO Annual Meeting Proceedings (2005) Abstract 3535, 23(16S; Part I of II: Jun. 1 Supplement).

Rusch et al., "Overexpression of the epidermal growth factor receptor and its ligand transforming growth factor alpha is frequent in resectable non-small cell lung cancer but does not predict tumor progression." *Clin. Cancer Res.* (1997) 515-522, 3(4).

Rusnak et al., "The effects of the novel EGFR/ErbB-2 tyrosine kinase inhibitor, GW2016, on the growth of human normal and transformed cell lines." *Proceedings of the American Association for Cancer Research* (2001) 803 (Abstract 4309), 42.

Rusnak et al., "The effects of the novel, reversible epidermal growth factor receptor/ErbB-2 tyrosine kinase inhibitor, GW2016, on the growth of human normal and tumor-derived cell lines in vitro and in vivo." *Molecular cancer therapeutics* (2001) 85-94, 1(2).

Safa et al., "Adjuvant immunotherapy for melanoma and colorectal cancers." *Semin. Oncol.* (2001) 68-92, 28(1).

Saikali et al., "Expression of nine tumour antigens in a series of human glioblastoma multiforme: interest of EGFRvIII, IL-13Ralpha2, gp100 and TRP-2 for immunotherapy." *Journal of Neuro-Oncology* (2007) 139-148, 81(2).

Sainsbury et al., "Epidermal-growth-factor receptor status as predictor of early recurrence of and death from breast cancer." *Lancet* (1987) 1398-1402, 1(8547).

Sainsbury et al., "Presence of epidermal growth factor receptor as an indicator of poor prognosis in patients with breast cancer." *Journal of Clinical Pathology* (1985) 1225-1228, 38(11).

Sako et al., "Single-molecule imaging of EGFR signalling on the surface of living cells." *Nature Cell Biology* (2000) 168-172, 2(3).

Salazar et al., "Dose-dependent inhibition of the EGFR and signalling pathways with the anti-EGFR monoclonal antibody (MAb) EMD 72000 administered every three weeks (q3w). A phase I pharmacokinetic/pharmacodynamic (PK/PD) study to define the optimal biological dose (OBD)." *Proceedings of the American Society of Clinical Oncology* (2004) 127s (Abstract 2002), 22.

Saleh et al., "Combined modality therapy of A431 human epidermoid cancer using anti-EGFr antibody C225 and radiation." *Cancer Biotherapy & Radiopharmaceutics* (1999) 451-463, 14(6).

Salomon et al., "Epidermal growth factor-related peptides and their receptors in human malignancies." *Crit. Rev. Oncol. Hematol.* (1995) 183-232, 19(3).

Saltz et al., "Interim Report of Randomized Phase II Trial of Cetuximab/Bevacizumab/Irinotecan (CBI) versus Cetuximab/Bevacizumab (CB) in Irinotecan-Refractory Colorectal Cancer" *Proceedings of the American Society of Clinical Oncology* (2006) Abstract 169b.

Saltz et al., "The presence and intensity of the cetuximab-induced acne-like rash predicts increased survival in studies across multiple malignancies" *Proc. Am. Soc. Clin. Oncol.* (2003) Abstract 817, 22.

Saltz et al., "Single agent IMC-C225 (Erbitux[TM]) has activity in CPT-11 refractory colorectal cancer that expresses the epidermal growth factor receptor (EGFR)." *Proceedings of the American Society of Clinical Oncology* (2002) 127a (Abstract 504), 21.

Saltz et al., "Cetuximab (IMC-225) plus irinotecan (CPT-11) is active in CPT-11-refractory colorectal cancer (CRC) that expresses epidermal growth factor receptor (EGFR)." *Proceedings of the American Society of Clinical Oncology* (2001) 3a (Abstract 7), 20.

Saltz et al., "Phase II trial of cetuximab in patients with refractory colorectal cancer that expresses the epidermal growth factor receptor." *J. Clin. Oncol.* (2004) 1201-1208, 22(7).

Sampson et al., "An EGFRvIII specific peptide vaccine generates antitumor immunity through a humoral pathway." *Neuro-oncology* (1999) S103 (Abstract 135).

Sampson et al., "Unarmed, tumor-specific monoclonal antibody effectively treats brain tumors." *Proceedings of the National Academy of Sciences of the United States of America* (2000) 7503-7508, 97(13).

Sampson et al., "Tumor-specific immunotherapy targeting the EGFRvIII mutation in patients with malignant glioma." *Seminars in immunology* (2008) 267-275, 20(5).

Sanderson et al., "In vivo drug-linker stability of an anti-CD30 dipeptide-linked auristatin immunoconjugate." *Clin. Cancer Res.* (2005) 843-852, 11(2; Part 1).

Sandler, "Nondermatologic adverse events associated with anti-EGFR therapy." *Oncology* (Williston Park, N.Y.) (2006) 35-40, 20(5 Suppl 2).

De Santes et al., "Radiolabeled antibody targeting of the HER-2/neu oncoprotein." *Cancer Res.* (1992) 1916-1923, 52(7).

Santon et al., "Effects of epidermal growth factor receptor concentration on tumorigenicity of A431 cells in nude mice." *Cancer Res.* (1986) 4701-4705, 46(9).

Sartor, "Biological modifiers as potential radiosensitizers: targeting the epidermal growth factor receptor family." *Semin. Oncol.* (2000) 15-20; 27(6; Suppl. 11).

Sartor, "Mechanisms of disease: Radiosensitization by epidermal growth factor receptor inhibitors." *Nature Clinical Practice. Oncology* (2004) 80-87, 1(2).

(56) References Cited

OTHER PUBLICATIONS

Sarup et al., "Characterization of an anti-p185HER2 monoclonal antibody that stimulates receptor function and inhibits tumor cell growth." *Growth Regulation* (1991) 72-82, 1(2).
Sato et al., "Derivation and assay of biological effects of monoclonal antibodies to epidermal growth factor receptors." *Methods in Enzymology* (1987) 63-81, 146.
Sato et al., "Biological effects in vitro of monoclonal antibodies to human epidermal growth factor receptors." *Molecular biology & medicine* (1983) 511-529, 1(5).
Sauter et al., "Patterns of epidermal growth factor receptor amplification in malignant gliomas." *The American Journal of Pathology* (1996) 1047-1053, 148(4).
Scher et al., "Changing pattern of expression of the epidermal growth factor receptor and transforming growth factor alpha in the progression of prostatic neoplasms." *Clin. Cancer Res.* (1995) 545-550, 1(5).
Schlegel et al., "Amplification of the epidermal-growth-factor-receptor gene correlates with different growth behaviour in human glioblastoma." *Int. J. Cancer* (1994) 72-77, 56(1).
Schlessinger, "Cell signaling by receptor tyrosine kinases." *Cell* (2000) 211-225, 103(2).
Schlessinger, "Common and distinct elements in cellular signaling via EGF and FGF receptors." *Science* (2004) 1506-1507, 306(5701).
Schlessinger, "Ligand-induced, receptor-mediated dimerization and activation of EGF receptor." *Cell* (2002) 669-672, 110(6).
Schmidt et al., "Suppression of metastasis formation by a recombinant single chain antibody-toxin targeted to full-length and oncogenic variant EGF receptors." *Oncogene* (1999) 1711-1721, 18(9).
Schmidt et al., "Expression of an oncogenic mutant EGF receptor markedly increases the sensitivity of cells to an EGF-receptor-specific antibody-toxin." *Int. J. Cancer* (1998) 878-884, 75(6).
Schmidt et al., "Epidermal growth factor receptor signaling intensity determines intracellular protein interactions, ubiquitination, and internalization." *Proceedings of the National Academy of Sciences of the United States of America* (2003) 6505-6510, 100(11).
Schmidt-Ullrich et al., "Radiation-induced proliferation of the human A431 squamous carcinoma cells is dependent on EGFR tyrosine phosphorylation." *Oncogene* (1997) 1191-1197, 15(10).
Schmiedel et al., "Matuzumab binding to EGFR prevents the conformational rearrangement required for dimerization." *Cancer Cell* (2008) 365-373, 13(4).
Schmitz et al., "Interaction of antibodies with ErbB receptor extracellular regions" *Experimental Cell Research* (2009) 659-670, 315(4).
Schnürch et al., "Growth inhibition of xenotransplanted human carcinomas by a monoclonal antibody directed against the epidermal growth factor receptor." *Eur. J. Cancer* (1994) 491-496, 30A(4).
Schwechheimer et al., "EGFR gene amplification-rearrangement in human glioblastomas." *Int. J. Cancer* (1995) 145-148, 62(2).
Scott, "Structural Biology and Molecular Imaging in Cancer Therapeutics" *Bosch Institute Annual Scientific Meeting* (Sydney, Australia) (2010).
Scott, "Pathway Specific Therapeutics: from Cancer Biology to Targeted Therapy" *Garvan Signalling Symposium* (Melbourne, Australia) (2010).
Scott, "Targeting a Novel EGFR Epitope on Cancer Cells" *Ludwig Institute for Cancer Research* (2010) Abstract 014.
Scott, "Antibody Therapeutics" *Ludwig Institute Colon Cancer Initiative Symposium* (Baltimore, MD, United States) (2010).
Scott, "Development of a humanised antibody against a novel epitope of EGFR" *2010 Australasian Vaccines & Immunotherapy Development [AVID] Meeting* (Melbourne, Australia) (2010).
Scott, "Development of a novel anti-EGFR humanised antibody—the complex path from Academia to Industry" *Lowy Symposium* (Sydney, Australia) (2010).
Scott, "Novel Antibodies that bind to a conformational epitope of EGFR" *IBC 20th Annual Antibody Engineering Conference* (San Diego, CA, United States) (2009).
Scott, "Targeting a Novel EGFR Epitope on Cancer Cells" *LICR Translational Oncology Conference* (Melbourne, Australia) (2009).
Scott, "Cell Surface Targets for Therapy" *LICR Brain Cancer Initiative Meeting* (Rockville, MD, United States) (2009).
Scott, "Targeting a Novel EGFR Epitope on Cancer Cells" *Keystone Symposia: Antibodies as Drugs: Targeted Cancer Therapies* (Whistler British Columbia, Canada) (2009).
Scott, "Therapy of EGFR Expressing Cancers with a Novel Tumor Specific Antibody" *AHMRC Congress* (Brisbane, Qld, Australia) (2008).
Scott, "Understanding the Biology of Targeted Therapies in Cancer" *University of Melbourne/Royal Melbourne Hospital/Western Hospital Consortium Seminar* (Melbourne, Australia (2008).
Scott, "The biology of EGFR in normal and diseased tissues" *Australian Lung Cancer Conference* (Surfers Paradise, Old, Australia) (2008).
Scott, "Recombinant Antibody Therapy of Cancer—the LICR Antibody Program" *A\*Star Agency for Science, Technology and Research, ICMB* (Singapore) (2008).
Scott, "Epidermal Growth Factor Receptor Targeting for Cancer Therapy" *3rd Barossa Meeting—Signalling Systems* (Barossa Valley, South Australia) (2007).
Scott, "Cell Surface and Intracellular targets for antibody directed cancer therapeutics" *City of Hope Cancer Center* (Los Angeles, CA, United States) (2007).
Scott, "Of Mice and Man—The Role of Growth Factor Receptors in Cancer" *Austin Hospital Division of Medicine Grand Round* (Melbourne, Australia) (2007).
Scott, "Targeting the Epidermal Growth Factor Receptor for Antibody Therapy of Solid Tumours" *Third International AntibOZ Conference* (Heron Island, Queensland, Australia) (2007).
Scott, "Targeting a Tumour Specific Epitope of the Epidermal Growth Factor Receptor" *2007 Keystone Symposium: Antibodies as Drugs: From Basic Biology to the Clinic* (Alberta, Canada) (2007).
Scott, "Targeting the Epidermal Growth Factor Receptor for Antibody Therapy of Solid Tumours" *17th Annual IBC Antibody Engineering Conference* (San Diego, CA, United States) (2006).
Scott, "EGFR Targeted Therapeutics" *ComBio 2006* (Brisbane, Australia) (2006).
Scott, "Implications of Antibody:Receptor Binding Structure and Signalling on Tumour Growth" *Discovery Science & Biotechnology Conference* (Melbourne, Australia) (2006).
Scott, "Targeting the Epidermal Growth Factor Receptor for Antibody Therapy of Solid Tumours" *EGFR Cascade Meeting* (San Diego, CA, United States) (2006).
Scott, "Implications of Antibody:Receptor Binding Structure and Signalling on Tumour Growth" *Monash University—Department of Biochemistry & Molecular Biology* (Melbourne, Australia) (2005).
Scott, "Receptor Based Targets for Antibody Therapy of Solid Tumours" *The Second China International Symposium on Antibody Engineering: Current Status and Future Perspective of Antibody Therapeutics* (Beijing, China) (2005).
Scott, "Novel Antibody that Inhibits EGFR Activation" *Fifth International Congress on Monoclonal Antibodies in Cancer* (Quebec City, Canada) (2005).
Scott, "Growth Factors and their implications in head and neck cancer" *Garnett Passe Scientific Meeting: Frontiers in Otorhinolaryngology 2004* (Noosa, Queensland, Australia) (2004).
Scott, "Recombinant Antibodies for Immune and Cell Signalling Based Therapeutics" *AntibOZ 2 Conference* (Heron Island, Queensland, Australia) (2004).
Scott, "Targeted Cancer Therapeutics—the Role of Signalling and Immune Effector Mechanisms" *Royal North Shore Hospital Scientific Forum* (Sydney, Nsw, Australia) (2003).
Scott, "Targeted Therapeutics—the Role of Signalling and Immune Effector Mechanism" *Centre for Immunology and Cancer Research, University of Queensland* (Brisbane, Queensland, Australia) (2003).
Scott, "Targeted Therapeutics—the Role of Signalling and Immune Effector Mechanisms" *Peter MacCallum Cancer Immunology Program Seminar* (Melbourne, Australia) (2003).
Scott, "Comparison of Phase I Trials of Anti-Epidermal Growth Factor Receptor (EGFR) Monoclonal Antibodies (Mabs) 528 and 225 Labelled With 1-131 and In-111" *J. Nucl. Med.* (1993) 213P, 34(5).

(56) References Cited

OTHER PUBLICATIONS

Scott, "Molecular Targets for Cancer Therapeutics" *Baker Institute Seminar* (Melbourne, Australia) (2002).
Scott, "Molecular Targets for Cancer Therapeutics" *Cambridge University Seminar* (United Kingdom) (2002).
Scott, "Molecular Targets for Cancer Therapeutics" *Monash University Seminar* (Melbourne, Australia) (2002).
Scott et al., "Specific targeting, biodistribution, and lack of immunogenicity of chimeric anti-GD3 monoclonal antibody KM871 in patients with metastatic melanoma: results of a phase I trial." *J. Clin. Oncol.* (2001) 3976-3987, 19(19).
Scott et al., "Construction, production, and characterization of humanized anti-Lewis Y monoclonal antibody 3S193 for targeted immunotherapy of solid tumors." *Cancer Res.* (2000) 3254-3261, 60(12).
Scott et al., "Antibody-based immunological therapies." *Curr. Opin Immunol.* (1997) 717-722, 9(5).
Scott et al., "Clinical promise of tumour immunology." *Lancet* (1997) SII19-22, 349(Suppl. 2).
Scott et al., "Tumor imaging and therapy." *Radioloqic clinics of North America* (1993) 859-879, 31(4).
Scott et al., "A Phase I single dose escalation trial of ch806 in patients with advanced tumors expressing the 806 antigen." *Journal of Clinical Oncology*, 2006 ASCO Annual Meeting Proceedings Part I. (2006) 13028, 24(18S (Jun. 20 Supplement)).
Scott et al., "A phase I biodistribution and pharmacokinetic trial of humanized monoclonal antibody Hu3s193 in patients with advanced epithelial cancers that express the Lewis-Y antigen." *Clin. Cancer Res.* (2007) 3286-3292, 13(11).
Scott et al., "A phase I clinical trial with monoclonal antibody ch806 targeting transitional state and mutant epidermal growth factor receptors." *Proceedings of the National Academy of Sciences of the United States of America* (2007) 4071-4076, 104(10).
Scott et al., "A phase I trial of humanized monoclonal antibody A33 in patients with colorectal carcinoma: biodistribution, pharmacokinetics, and quantitative tumor uptake." *Clin. Cancer Res.* (2005) 4810-4817, 11(13).
Scott et al., "Immunological effects of chimeric anti-GD3 monoclonal antibody KM871 in patients with metastatic melanoma." *Cancer immunity : a journal of the Academy of Cancer Immunology* (2005) 3, 5.
Scott et al., "A Phase I dose-escalation study of sibrotuzumab in patients with advanced or metastatic fibroblast activation protein-positive cancer." *Clin. Cancer Res.* (2003) 1639-1647, 9(5).
Sellers et al., "Apoptosis and cancer drug targeting." *J. Clin. Invest.* (1999) 1655-1661, 104(12).
Senter, "Potent antibody drug conjugates for cancer therapy" *Current Opinion in Chemical Biology* (2009) 235-244, 13(3).
Senzer et al., "Phase 2 Evaluation of OSI-774, a Potent Oral Antagonist of the EGFR-TK in Patients with Advanced Squamous Cell Carcinoma of the Head and Neck." *Proceedings of the American Society of Clinical Oncology* (2001) 2a (Abstract 6), 20.
Sepp-Lorenzino et al., "Farnesyl:protein transferase inhibitors (FTIs) block tyrosine kinase signal transduction and act in concert with an anti-EGR receptor antibody to inhibit cancer cell growth." *Proceedings of the Annual Meeting of the American Association for Cancer Research* (1996) 421-422 (Abstract 2877), 37.
Seymour, "Novel anti-cancer agents in development: exciting prospects and new challenges." *Cancer Treat Rev.* (1999) 301-312, 25(5).
Sharafinski et al., "Epidermal growth factor receptor targeted therapy of squamous cell carcinoma of the head and neck." *Head & Neck* (2010) 1412-1421, 32(10).
She et al., "The BAD protein integrates survival signaling by EGFR/MAPK and PI3K/Akt kinase pathways in PTEN-deficient tumor cells." *Cancer Cell* (2005) 287-297, 8(4).
Shepherd et al., "Unraveling the mystery of prognostic and predictive factors in epidermal growth factor receptor therapy." *Journal of Clinical Oncology* (2006) 1219-20; author reply 1220-1, 24(7).
Sherrill et al., "Activation of epidermal growth factor receptor by epidermal growth factor." *Biochemistry* (1996) 5705-5718, 35(18).
Shibata et al., "Enhancing effects of epidermal growth factor on human squamous cell carcinoma motility and matrix degradation but not growth." *Tumour Biology : the Journal of the International Society for Oncodevelopmental Biology and Medicine* (1996) 168-175, 17(3).
Shigematsu et al., "Clinical and biological features associated with epidermal growth factor receptor gene mutations in lung cancers." *J. Natl. Cancer Inst.* (2005) 339-346, 97(5).
Shimizu et al., "Detection of epidermal growth factor receptor gene amplification in human squamous cell carcinomas using fluorescence in situ hybridization." *Japanese Journal of Cancer Research : Gann* (1994) 567-571, 85(6).
Shimizu et al., "Genetics of cell surface receptors for bioactive polypeptides: binding of epidermal growth factor is associated with the presence of human chromosome 7 in human-mouse cell hybrids." *Proceedings of the National Academy of Sciences of the United States of America* (1980) 3600-3604, 77(6).
Shin et al., "Epidermal growth factor receptor-targeted therapy with C225 and cisplatin in patients with head and neck cancer." *Clin. Cancer Res.* (2001) 1204-1213, 7(5).
Shin et al., "Dysregulation of epidermal growth factor receptor expression in premalignant lesions during head and neck tumorigenesis." *Cancer Res.* (1994) 3153-3159, 54(12).
Shinkawa et al., "The absence of fucose but not the presence of galactose or bisecting N-acetylglucosamine of human IgG1 complex-type oligosaccharides shows the critical role of enhancing antibody-dependent cellular cytotoxicity." *JBC* (2003) 3466-3473, 278(5).
Shinojima et al., "Prognostic value of epidermal growth factor receptor in patients with glioblastoma multiforme." *Cancer Res.* (2003) 6962-6970, 63(20).
Shintani, "Gefitinib ('Iressa', ZD1839), an epidermal growth factor receptor tyrosine kinase inhibitor, up-regulates p27KIP1 and induces G1 arrest in oral squamous cell carcinoma cell lines" *Oral oncology* (2004) 43-51, 40(1).
Shintani et al., "Intragenic mutation analysis of the human epidermal growth factor receptor (EGFR) gene in malignant human oral keratinocytes." *Cancer Res.* (1999) 4142-4147, 59(16).
Shusta et al., "Directed evolution of a stable scaffold for T-cell receptor engineering." *Nat. Biotechnol.* (2000) 754-759, 18(7).
Shusta et al., "Yeast polypeptide fusion surface display levels predict thermal stability and soluble secretion efficiency." *J. Mol. Biol.* (1999) 949-956, 292(5).
Sibilia et al., "The EGF receptor provides an essential survival signal for SOS-dependent skin tumor development." *Cell* (2000) 211-220, 102(2).
Siegel-Lakhai et al., "Current knowledge and future directions of the selective epidermal growth factor receptor inhibitors erlotinib (Tarceva) and gefitinib (Iressa)." *Oncologist* (2005) 579-589, 10(8).
Silver et al., "Erbb is linked to the alpha-globin locus on mouse chromosome 11." *Mol. Cell Biol.* (1985) 1784-1786, 5(7).
Sirotnak et al., "Potentiation of cytotoxic agents against human tumors in mice by ZD1839 (Iressa), an inhibitor of EGFR tyrosine kinase, does not require high levels of expression of EGFR." *Proceedings of the Annual Meeting of the American Association for Cancer Research* (2000) 482 (Abstract 3076), 41.
Sirotnak et al., "Efficacy of cytotoxic agents against human tumor xenografts is markedly enhanced by coadministration of ZD1839 (Iressa), an inhibitor of EGFR tyrosine kinase." *Clin. Cancer Res.* (2000) 4885-4892, 6(12).
Sivasubramanian et al., "Structural model of the mAb 806-EGFR complex using computational docking followed by computational and experimental mutagenesis." *Structure* (2006) 401-414, 14(3).
Sizeland et al., "Anti-sense transforming growth factor alpha oligonucleotides inhibit autocrine stimulated proliferation of a colon carcinoma cell line." *Mol. Biol. Cell* (1992) 1235-1243, 3(11).
Sizeland et al., "The proliferative and morphologic responses of a colon carcinoma cell line (LIM 1215) require the production of two autocrine factors." *Mol. Cell Biol.* (1991) 4005-4014, 11(8).
Skov et al., "Interaction of platinum drugs with clinically relevant x-ray doses in mammalian cells: a comparison of cisplatin, carboplatin, iproplatin, and tetraplatin." *Int. J. Radiat. Oncol. Biol. Phys.* (1991) 221-225, 20(2).

(56) References Cited

OTHER PUBLICATIONS

Slamon, "Use of Chemotherapy Plus a Monoclonal Antibody Against HER2 for Metastatic Breast Cancer That Overexpresses HER2" *The New England Journal of Medicine* (2001) 783-792, 344(11).
Slamon et al., "Addition of Herceptin (Humanized anti-HER2 antibody) to first line chemotherapy for HER2 overexpressing metastatic breast cancer (HER2+/MBC) markedly increases anticancer activity: a randomized, multinational controlled phase III trial." *Proceedings of the Annual Meeting of the American Society of Clinical Oncology* (1998) 98a (Abstract 377), 17.
Slamon et al., "Studies of the HER-2/neu proto-oncogene in human breast and ovarian cancer." *Science* (1989) 707-712, 244(4905).
Slichenmyer et al., "Anticancer therapy targeting the erbB family of receptor tyrosine kinases." *Semin. Oncol.* (2001) 67-79, 28(5; Suppl. 16).
Slieker et al., "Synthesis of epidermal growth factor receptor in human A431 cells. Glycosylation-dependent acquisition of ligand binding activity occurs post-translationally in the endoplasmic reticulum." *JBC* (1986) 15233-15241, 261(32).
Slieker et al., "Post-translational processing of the epidermal growth factor receptor. Glycosylation-dependent acquisition of ligand-binding capacity." *JBC* (1985) 687-690, 260(2).
Sliwkowski et al., "Nonclinical studies addressing the mechanism of action of trastuzumab (Herceptin)." *Semin. Oncol.* (1999) 60-70, 26(4 Suppl 12).
Smith et al., "PTEN mutation, EGFR amplification, and outcome in patients with anaplastic astrocytoma and glioblastoma multiforme." *J. Natl. Cancer Inst.* (2001) 1246-1256, 93(16).
Sobol et al., "Epidermal growth factor receptor expression in human lung carcinomas defined by a monoclonal antibody." *J. Natl. Cancer Inst.* (1987) 403-407, 79(3).
Soderquist et al., "Glycosylation of the epidermal growth factor receptor in A-431 cells. The contribution of carbohydrate to receptor function." *Journal of Biological Chemistry* (1984) 12586-12594, 259(20).
Solbach et al., "Antitumor effect of MAb EMD 55900 depends on EGF-R expression and histopathology." *Neoplasia* (2002) 237-242, 4(3).
Solomon et al., EGFR blockade with ZD1839 ('Iressa') potentiates the antitumor effects of single and multiple fractions of ionizing radiation in human A431 squamous cell carcinoma. *Int. J. Radiat. Oncol. Biol. Phys.* (2003) 713-723, 55(3).
Solomon et al., "Rash from EGFR inhibitors: opportunities and challenges for palliation." *Current oncology reports* (2008) 304-308, 10(4).
Sonabend et al., "Targeting epidermal growth factor receptor variant III: a novel strategy for the therapy of malignant glioma." *Expert Review of Anticancer Therapy* (2007) S45-50, 7(12; Supplement).
Sørensen et al., "Injury-induced innate immune response in human skin mediated by transactivation of the epidermal growth factor receptor." *J. Clin. Invest.* (2006) 1878-1885, 116(7).
Sorscher, "EGFR mutations and sensitivity to gefitinib." *N. Engl. J. Med.* (2004) 1260-1261, 351(12).
Soulieres, "Multicenter Phase II Study of Erlotinib, an Oral Epidermal Growth Factor Receptor Tyrosine Kinase Inhibitor, in Patients With Recurrent or Metastatic Squamous Cell Cancer of the Head and Neck" *Journal of Clinical Oncology* (2003) 77-85, 22(1).
Spurr et al., "Mapping of cellular oncogenes; erb B on chromosome 7" *Cytogenet. Cell Genet.* (1984) 590, 37.
Spurr et al., "Chromosomal localisation of the human homologues to the oncogenes erbA and B." *EMBO J.* (1984) 159-163, 3(1).
Sridhar et al., "Inhibitors of epidermal-growth-factor receptors: a review of clinical research with a focus on non-small-cell lung cancer." *The Lancet Oncology* (2003) 397-406, 4(7).
Stabin et al., "OLINDA/EXM: the second-generation personal computer software for internal dose assessment in nuclear medicine." *J. Nucl. Med.* (2005) 1023-1027, 46(6).
Stamos et al., "Structure of the epidermal growth factor receptor kinase domain alone and in complex with a 4-anilinoquinazoline inhibitor." *JBC* (2002) 46265-46272, 277(48).
Stancovski et al., "Mechanistic aspects of the opposing effects of monoclonal antibodies to the ERBB2 receptor on tumor growth." *Proceedings of the National Academy of Sciences of the United States of America* (1991) 8691-8695, 88(19).
Steffens et al., "Targeting of renal cell carcinoma with iodine-131-labeled chimeric monoclonal antibody G250." *J. Clin. Oncol.* (1997) 1529-1537, 15(4).
Stockert et al., "Annual Research Report 1997" *Ludwig Institute for Cancer Research* (1997) 212-213.
Stockert et al., "Annual Research Report 1995" *Ludwig Institute for Cancer Research* (1995) 226-227.
Stockhausen et al., "Maintenance of EGFR and EGFRvIII expressions in an in vivo and in vitro model of human glioblastoma multiforme." *Exp. Cell Res.* (2011) 1513-1526, 317(11).
Stragliotto et al., "Multiple infusions of anti-epidermal growth factor receptor (EGFR) monoclonal antibody (EMD 55,900) in patients with recurrent malignant gliomas." *Eur. J. Cancer* (1996) 636-640, 32A(4).
Studnicka et al., "Human-engineered monoclonal antibodies retain full specific binding activity by preserving non-CDR complementarity-modulating residues." *Protein Engineering* (1994) 805-814, 7(6).
Sturgis et al., "Effects of antiepidermal growth factor receptor antibody 528 on the proliferation and differentiation of head and neck cancer." *Otolaryngology—head and neck surgery : official journal of American Academy of Otolaryngology—Head and Neck Surgery* (1994) 633-643, 111(5).
Sugawa et al., "Function of aberrant EGFR in malignant gliomas." *Brain Tumor Pathology* (1998) 53-57, 15(1).
Sugawa et al., "Identical splicing of aberrant epidermal growth factor receptor transcripts from amplified rearranged genes in human glioblastomas." *Proceedings of the National Academy of Sciences of the United States of America* (1990) 8602-8606, 87(21).
Sugimura et al., "[Immunohistochemical study on the expression of epidermal growth factor receptor (EGF-R) in invasive cervical cancer of the uterus]." *Nippon Sanka Fuiinka Gakkai zasshi* (1992) 689-694, 44(6).
Sunada et al., "Monoclonal antibody against epidermal growth factor receptor is internalized without stimulating receptor phosphorylation." *Proceedings of the National Academy of Sciences of the United States of America* (1986) 3825-3829, 83(11).
Sutherland et al., "Lysosomal trafficking and cysteine protease metabolism confer target-specific cytotoxicity by peptide-linked anti-CD30-auristatin conjugates." *Journal of Biological Chemistry* (2006) 10540-10547, 281(15).
Suwa et al., "Epidermal growth factor receptor-dependent cytotoxic effect of anti-EGFR antibody-ribonuclease conjugate on human cancer cells." *Anticancer Research* (1999) 4161-4165, 19(5B).
Swaisland et al., "Pharmacokinetics and tolerability of the orally active selective epidermal growth factor receptor tyrosine kinase inhibitor ZD1839 in healthy volunteers." *Clinical pharmacokinetics* (2001) 297-306, 40(4).
Tabernero et al., "An international phase II study of cetuximab in combination with oxaliplatin/5-fluorouracil (5-FU)/folinic acid (FA) (FOLFOX-4) in the first-line treatment of patients with metastatic colorectal cancer (CRC) expressing epidermal growth factor receptor (EGFR)." *Proceedings of the American Society of Clinical Oncology* (2004) 248s (Abstract 3512), 23.
Tabernero et al., "A phase I PK and serial tumor and skin pharmacodynamic (PD) study of weekly (q1w), every 2-week (q2w) or every 3-week (q3w) 1-hour (h) infusion EMD72000, a humanized monoclonal anti-epidermal growth factor receptor (EGFR) antibody, in patients (pt) with advanced tumors." *Proceedings of the American Society of Clinical Oncology* (2003) 192 (Abstract 770), 22.
Taetle et al., "Effects of anti-epidermal growth factor (EGF) receptor antibodies and an anti-EGF receptor recombinant-ricin a chain immunoconjugate on growth of human cell" *Chemical Abstracts* (1988) 184218a, 109(21).
Taetle et al., "Effects of anti-epidermal growth factor (EGF) receptor antibodies and an anti-EGF receptor recombinant-ricin A chain immunoconjugate on growth of human cells." *J. Natl. Cancer Inst.* (1988) 1053-1059, 80(13).
Tahtis et al., "Biodistribution properties of (111)indium-labeled C-functionalized trans-cyclohexyl diethylenetriaminepentaacetic

(56) References Cited

OTHER PUBLICATIONS acid humanized 3S193 diabody and F(ab')(2) constructs in a breast carcinoma xenograft model." *Clin. Cancer Res.* (2001) 1061-1072, 7(4).
Tai et al., "Co-overexpression of fibroblast growth factor 3 and epidermal growth factor receptor is correlated with the development of nonsmall cell lung carcinoma." *Cancer* (2006) 146-155, 106(1).
Takahashi et al., "Radioimmunodetection of human glioma xenografts by monoclonal antibody to epidermal growth factor receptor." *Cancer Res.* (1987) 3847-3850, 47(14).
Takasu et al., "Antibody-based therapy for brain tumor." *Nippon rinsho. Japanese journal of clinical medicine* (2005) 563-568, 63(Suppl. 9).
Takasu et al., "Radioimmunoscintigraphy of intracranial glioma xenograft with a technetium-99m-labeled mouse monoclonal antibody specifically recognizing type III mutant epidermal growth factor receptor." *Journal of neuro-oncology* (2003) 247-256, 63(3).
Tan et al., "Pharmacokinetics of cetuximab after administration of escalating single dosing and weekly fixed dosing in patients with solid tumors." *Clin. Cancer Res.* (2006) 6517-6522, 12(21).
Tang et al., "Epidermal growth factor receptor vIII enhances tumorigenicity in human breast cancer." *Cancer Res.* (2000) 3081-3087, 60(11).
Tang et al., "The autocrine loop of TGF-alpha/EGFR and brain tumors." *Journal of neuro-oncology* (1997) 303-314, 35(3).
Tang et al., "Phase II study of ispinesib in recurrent or metastatic squamous cell carcinoma of the head and neck." *Investigational new drugs* (2008) 257-264, 26(3).
Tannock, "Treatment of cancer with radiation and drugs." *J. Clin. Oncol.* (1996) 3156-3174, 14(12).
Tanswell et al., "Population pharmacokinetics of antifibroblast activation protein monoclonal antibody F19 in cancer patients." *British journal of clinical pharmacology* (2001) 177-180, 51(2).
Tateishi et al., "Prognostic influence of the co-expression of epidermal growth factor receptor and c-erbB-2 protein in human lung adenocarcinoma." *Surgical oncology* (1994) 109-113, 3(2).
Temam et al., "Epidermal growth factor receptor copy number alterations correlate with poor clinical outcome in patients with head and neck squamous cancer." *Journal of Clinical Oncology* (2007) 2164-2170, 25(16).
Temming et al., "Evaluation of RGD-targeted albumin carriers for specific delivery of auristatin E to tumor blood vessels." *Bioconjugate chemistry* (2006) 1385-1394, 17(6).
Teramoto et al., "Inhibitory effect of anti-epidermal growth factor receptor antibody on a human gastric cancer." *Cancer* (1996) 1639-1645, 77(8 Suppl).
Tewes et al., "Results of a phase I trial of the humanized anti epidermal growth factor receptor (EGFR) monoclonal antibody EMD 72000 in patients with EGFR expressing solid tumors." *Proceedings of the American Society of Clinical Oncology* (2002) 95a (Abstract 378), 21.
Thaung et al., "Novel ENU-induced eye mutations in the mouse: models for human eye disease." *Human molecular genetics* (2002) 755-767, 11(7).
Thomas et al., "Pharmacokinetic and pharmacodynamic properties of EGFR inhibitors under clinical investigation." *Cancer Treat Rev.* (2004) 255-268, 30(3).
Thompson et al., "The EGF receptor: structure, regulation and potential role in malignancy." *Cancer surveys* (1985) 767-788, 4(4).
Tice et al., "Mechanism of biological synergy between cellular Src and epidermal growth factor receptor." *Proceedings of the National Academy of Sciences of the United States of America* (1999) 1415-1420, 96(4).
Tietze et al., "Novel analogues of CC-1065 and the duocarmycins for the use in targeted tumour therapies." *Anti-cancer agents in medicinal chemistry* (2009) 304-325, 9(3).
Tochon-Danguy et al., "Imaging and quantitation of the hypoxic cell fraction of viable tumor in an animal model of intracerebral high grade glioma using [18F]fluoromisonidazole (FMISO)." *Nucl. Med. Biol.* (2002) 191-197, 29(2).

Todaro et al., "Transformation by murine and feline sarcoma viruses specifically blocks binding of epidermal growth factor to cells." *Nature* (1976) 26-31, 264(5581).
Todd et al., "Epidermal growth factor receptor (EGFR) biology and human oral cancer." *Histology and histopathology* (1999) 491-500, 14(2).
Toi et al., "Epidermal growth factor receptor expression as a prognostic indicator in breast cancer." *Eur. J. Cancer* (1991) 977-980, 27(8).
Tokuda et al., "In vitro and in vivo anti-tumour effects of a humanised monoclonal antibody against c-erbB-2 product." *British Journal of Cancer* (1996) 1362-1365, 73(11).
Tokumo et al., "The relationship between epidermal growth factor receptor mutations and clinicopathologic features in non-small cell lung cancers." *Clin. Cancer Res.* (2005) 1167-1173, 11(3).
Torres et al., "Phase I/II clinical trial of the humanized anti-EGF-r monoclonal antibody h-R3 labelled with 99mTc in patients with tumour of epithelial origin." *Nuclear medicine communications* (2005) 1049-1057, 26(12).
Toth et al., "Analysis of EGFR gene amplification, protein overexpression and tyrosine kinase domain mutation in recurrent glioblastoma." *Pathology oncology research : POR* (2009) 225-229, 15(2).
Toyooka et al., "EGFR mutation and response of lung cancer to gefitinib." *N. Engl. J. Med.* (2005) 2136, 352(20).
Trail et al., "Monoclonal antibody drug conjugates in the treatment of cancer." *Curr. Opin. Immunol.* (1999) 584-588, 11(5).
Tran et al., "CAML is required for efficient EGF receptor recycling." *Developmental cell* (2003) 245-256, 5(2).
Traxler et al., "AEE788: a dual family epidermal growth factor receptor/ErbB2 and vascular endothelial growth factor receptor tyrosine kinase inhibitor with antitumor and antiangiogenic activity." *Cancer Res.* (2004) 4931-4941, 64(14).
Trigo et al., "Cetuximab monotherapy is active in patients (pts) with platinum-refractory recurrent/metastatic squamous cell carcinoma of the head and neck (SCCHN) (Results of a phase II study)." *Proceedings of the American Society of Clinical Oncology* (2004) 488s (Abstract 5502), 22.
Trummell et al., "The biological effects of anti-epidermal growth factor receptor and ionizing radiation in human head and neck tumor cell lines." *Proceedings of the American Association for Cancer Research* (1999) 144 (Abstract 958), 40.
Tsao et al., "Erlotinib in lung cancer—molecular and clinical predictors of outcome." *N. Engl. J. Med.* (2005) 133-144, 353(2).
Tsuchihashi et al., "Responsiveness to cetuximab without mutations in EGFR." *N. Engl. J. Med.* (2005) 208-209, 353(2).
Tsugu et al., "Localization of aberrant messenger RNA of epidermal growth factor receptor (EGFR) in malignant glioma." *Anticancer research* (1997) 2225-2232, 17(3C).
Türkeri et al., "Impact of the expression of epidermal growth factor, transforming growth factor alpha, and epidermal growth factor receptor on the prognosis of superficial bladder cancer." *Urology* (1998) 645-649, 51(4).
Turner et al., "EGF receptor signaling enhances in vivo invasiveness of DU-145 human prostate carcinoma cells." *Clinical & experimental metastasis* (1996) 409-418, 14(4).
Tzahar et al., "Bivalence of EGF-like ligands drives the ErbB signaling network." *EMBO J.* (1997) 4938-4950, 16(16).
Uegaki et al., "Clinicopathological significance of epidermal growth factor and its receptor in human pancreatic cancer." *Anticancer research* (1997) 3841-3847, 17(5B).
Uemura et al., "Internal image anti-idiotype antibodies related to renal-cell carcinoma-associated antigen G250." *Int. J. Cancer* (1994) 609-614, 56(4).
Ullrich et al., "Signal transduction by receptors with tyrosine kinase activity." *Cell* (1990) 203-212, 61(2).
Ullrich et al., "Human epidermal growth factor receptor cDNA sequence and aberrant expression of the amplified gene in A431 epidermoid carcinoma cells." *Nature* (1984) 418-425, 309(5967).
Ushiro et al., "Identification of phosphotyrosine as a product of epidermal growth factor-activated protein kinase in A-431 cell membranes." *JBC* (1980) 8363-8365, 255(18).

(56) References Cited

OTHER PUBLICATIONS

Vagin et al., "MOLREP: an Automated Program for Molecular Replacement" *J. Appl. Cryst.* (1997) 1022-1025, 30.
Vagin et al., "Spherically averaged phased translation function and its application to the search for molecules and fragments in electron-density maps." *Acta Crystallogr. D. Biol. Crystallogr.* (2001) 1451-1456, 57(Pt 10).
Vaidyanathan et al., "Improved xenograft targeting of tumor-specific anti-epidermal growth factor receptor variant III antibody labeled using N-succinimidyl 4-guanidinomethyl-3-iodobenzoate." *Nucl. Med. Biol.* (2002) 1-11, 29(1).
Vajdos et al., "Comprehensive functional maps of the antigen-binding site of an anti-ErbB2 antibody obtained with shotgun scanning mutagenesis." *J. Mol. Biol.* (2002) 415-428, 320(2).
Vanhoefer et al., "Phase I study of the humanized antiepidermal growth factor receptor monoclonal antibody EMD72000 in patients with advanced solid tumors that express the epidermal growth factor receptor." *J. Clin. Oncol.* (2004) 175-184, 22(1).
Veale et al., "The relationship of quantitative epidermal growth factor receptor expression in non-small cell lung cancer to long term survival." *British Journal of Cancer* (1993) 162-165, 68(1).
Veale et al., "Epidermal growth factor receptors in non-small cell lung cancer." *British Journal of Cancer* (1987) 513-516, 55(5).
Velu et al., "Epidermal-growth-factor-dependent transformation by a human EGF receptor proto-oncogene." *Science* (1987) 1408-1410, 238(4832).
Venter et al., "Overexpression of the c-erbB-2 oncoprotein in human breast carcinomas: immunohistological assessment correlates with gene amplification." *Lancet* (1987) 69-72, 2(8550).
Verbeek et al., "Overexpression of EGFR and c-erbB2 causes enhanced cell migration in human breast cancer cells and NIH3T3 fibroblasts." *FEBS letters* (1998) 145-150, 425(1).
Vermorken et al., "Cetuximab (Erbitux®) in recurrent/metastatic (R&M) squamous cell carcinoma of the head and neck (SCCHN) refractory to first-line platinum-based therapies" *Journal of Clinical Oncology*, 2005 ASCO Annual Meeting Proceedings (2005) Abstract 5505, 23(16S; Part I of II: Jun. 1, Supplement).
Vermorken et al., "Platinum-based chemotherapy plus cetuximab in head and neck cancer." *N. Engl. J. Med.* (2008) 1116-1127, 359(11).
Verveer et al., "Quantitative imaging of lateral ErbB1 receptor signal propagation in the plasma membrane." *Science* (2000) 1567-1570, 290(5496).
Viana-Pereira et al., "Analysis of EGFR overexpression, EGFR gene amplification and the EGFRvIII mutation in Portuguese high-grade gliomas." *Anticancer research* (2008) 913-920, 28(2A).
Van De Vijver et al., "Ligand-induced activation of A431 cell epidermal growth factor receptors occurs primarily by an autocrine pathway that acts upon receptors on the surface rather than intracellularly." *Journal of Biological Chemistry* (1991) 7503-7508, 266(12).
Viloria-Petit et al., "Acquired resistance to the antitumor effect of epidermal growth factor receptor-blocking antibodies in vivo: a role for altered tumor angiogenesis." *Cancer Res.* (2001) 5090-5101, 61(13).
Vincent et al., "Anticancer efficacy of the irreversible EGFr tyrosine kinase inhibitor PD 0169414 against human tumor xenografts." *Cancer chemotherapy and pharmacology* (2000) 231-238, 45(3).
Vitali et al., "Monoclonal Antibody 806 Inhibits the Growth of Subcutaneous and Intracranial Tumor Xenografts Expressing either the de2-7 or Amplified Epidermal Growth Factor Receptor (EGFR) but not Wild-Type EGFR." *Proceedings of the 14th Annual Lorne Cancer Conference*, Lorne, Victoria, Australia (2002) Abstract 221.
Voelzke et al., "Targeting the epidermal growth factor receptor in high-grade astrocytomas." *Current treatment options in oncology* (2008) 23-31, 9(1).
Vogel et al., "First-Line Herceptin® Monotherapy in Metastatic Breast Cancer" *Oncology* (2001) 37-42, 61(Suppl. 2).
Vogel et al., "Efficacy and safety of trastuzumab as a single agent in first-line treatment of HER2-overexpressing metastatic breast cancer." *J. Clin. Oncol.* (2002) 719-726, 20(3).
Vogt et al., "Relationships linking amplification level to gene over-expression in gliomas." *PLoS One* (2010) e14249, 5(12).
Voldborg et al., "Epidermal growth factor receptor (EGFR) and EGFR mutations, function and possible role in clinical trials." *Ann Oncol.* (1997) 1197-1206, 8(12).
Volm et al., "Prognostic value of ERBB-1, VEGF, cyclin A, FOS, JUN and MYC in patients with squamous cell lung carcinomas." *British Journal of Cancer* (1998) 663-669, 77(4).
Wade et al., "An automated peptide and protein thiazolidine coupling chemistry for biosensor immobilization giving a unique N-terminal orientation." *Analytical biochemistry* (2006) 315-317, 348(2).
Wakeling et al., "Specific inhibition of epidermal growth factor receptor tyrosine kinase by 4-anilinoquinazolines." *Breast cancer research and treatment* (1996) 67-73, 38(1).
Wakeling, "Epidermal growth factor receptor tyrosine kinase inhibitors." *Current opinion in pharmacology* (2002) 382-387, 2(4).
Wakeling et al., "Human EGFR, a candidate gene for the Silver-Russell syndrome, is biallelically expressed in a wide range of fetal tissues." *European journal of human genetics : EJHG* (1998) 158-164, 6(2).
Waksal, "Role of an anti-epidermal growth factor receptor in treating cancer." *Cancer Metastasis Rev.* (1999) 427-436, 18(4).
Waldmann, "Monoclonal antibodies in diagnosis and therapy." *Science* (1991) 1657-1662, 252(5013).
Walewski et al., "Rituximab (Mabthera, Rituxan) in patients with recurrent indolent lymphoma: evaluation of safety and efficacy in a multicenter study." *Medical oncology* (Northwood, London, England) (2001) 141-148, 18(2).
Walker et al., "Activation of the Ras/mitogen-activated protein kinase pathway by kinase-defective epidermal growth factor receptors results in cell survival but not proliferation." *Mol. Cell Biol.* (1998) 7192-7204, 18(12).
Walker et al., "Biochemical characterization of mutant EGF receptors expressed in the hemopoietic cell line BaF/3." *Growth Factors* (1998) 53-67, 16(1).
Walker et al., "Reconstitution of the high affinity epidermal growth factor receptor on cell-free membranes after transmodulation by platelet-derived growth factor." *Journal of Biological Chemistry* (1991) 2746-2752, 266(5).
Walker et al., "CR1/CR2 interactions modulate the functions of the cell surface epidermal growth factor receptor." *JBC* (2004) 22387-22398, 279(21).
Walker et al., "Expression of epidermal growth factor receptor mRNA and protein in primary breast carcinomas." *Breast cancer research and treatment* (1999) 167-176, 53(2).
Walton et al., "Analysis of deletions of the carboxyl terminus of the epidermal growth factor receptor reveals self-phosphorylation at tyrosine 992 and enhanced in vivo tyrosine phosphorylation of cell substrates." *Journal of Biological Chemistry* (1990) 1750-1754, 265(3).
Wang et al., "Immunohistochemical localization of c-erbB-2 protein and epidermal growth factor receptor in normal surface epithelium, surface inclusion cysts, and common epithelial tumours of the ovary." *Virchows Archiv. A, Pathological anatomy and histopathology* (1992) 393-400, 421(5).
Wang et al., "Epidermal growth factor receptor vIII enhances tumorigenicity and resistance to 5-fluorouracil in human hepatocellular carcinoma." *Cancer Letters* (2009) 30-38, 279(1).
Wang et al., "Epidermal growth factor receptor is a cellular receptor for human cytomegalovirus." *Nature* (2003) 456-461, 424(6947).
Wang et al., "Endocytosis deficiency of epidermal growth factor (EGF) receptor-ErbB2 heterodimers in response to EGF stimulation." *Mol. Biol. Cell* (1999) 1621-1636, 10(5).
Wargalla et al., "Rate of internalization of an immunotoxin correlates with cytotoxic activity against human tumor cells." *Proceedings of the National Academy of Sciences of the United States of America* (1989) 5146-5150, 86(13).
Waterfield et al., "A monoclonal antibody to the human epidermal growth factor receptor." *J. Cell Biochem.* (1982) 149-161, 20(2).
Waterman et al., "Molecular mechanisms underlying endocytosis and sorting of ErbB receptor tyrosine kinases." *FEBS letters* (2001) 142-152, 490(3).

(56) References Cited

OTHER PUBLICATIONS

Waterman et al., "Alternative intracellular routing of ErbB receptors may determine signaling potency." *JBC* (1998) 13819-13827, 273(22).
Waugh et al., "Epidermal growth factor receptor activation is localized within low-buoyant density, non-caveolar membrane domains." *Biochem. J.* (1999) 591-597, 337(Part 3).
Webster et al., "Engineering antibody affinity and specificity." *International journal of cancer* (1988) 13-16, 3.
Wedegaertner et al., "Effect of carboxyl terminal truncation on the tyrosine kinase activity of the epidermal growth factor receptor." *Archives of biochemistry and biophysics* (1992) 273-280, 292(1).
Wedegaertner et al., "Activation of the purified protein tyrosine kinase domain of the epidermal growth factor receptor." *Journal of Biological Chemistry* (1989) 11346-11353, 264(19).
Weiner, "An overview of monoclonal antibody therapy of cancer." *Semin. Oncol.* (1999) 41-50, 26(4 Suppl 12).
Weiss et al., "Rapid mapping of protein functional epitopes by combinatorial alanine scanning." *Proceedings of the National Academy of Sciences of the United States of America* (2000) 8950-8954, 97(16).
Wells, "EGF receptor." *The international journal of biochemistry & cell biology* (1999) 637-643, 31(6).
Wells et al., "Ligand-induced transformation by a noninternalizing epidermal growth factor receptor." *Science* (1990) 962-964, 247(4945).
Welt et al., "Phase I study of humanized A33 (huA33) antibody in patients with advanced colorectal cancer." *Proceedings of the Annual Meeting of the American Society of Clinical Oncology* (1997) 436a (Abstract 1563), 16.
Welt et al., "Phase I/II study of iodine 125-labeled monoclonal antibody A33 in patients with advanced colon cancer." *J. Clin. Oncol.* (1996) 1787-1797, 14(6).
Welt et al., "Phase I/II study of iodine 131-labeled monoclonal antibody A33 in patients with advanced colon cancer." *J. Clin. Oncol.* (1994) 1561-1571, 12(8).
Welt et al., "Antibody targeting in metastatic colon cancer: a phase I study of monoclonal antibody F19 against a cell-surface protein of reactive tumor stromal fibroblasts." *J. Clin. Oncol.* (1994) 1193-1203, 12(6).
Welt et al., "Quantitative analysis of antibody localization in human metastatic colon cancer: a phase I study of monoclonal antibody A33." *J. Clin. Oncol.* (1990) 1894-1906, 8(11).
Welt et al., "Phase I study of anticolon cancer humanized antibody A33." *Clin. Cancer Res.* (2003) 1338-1346, 9(4).
Welt et al., "Preliminary report of a phase I study of combination chemotherapy and humanized A33 antibody immunotherapy in patients with advanced colorectal cancer." *Clin. Cancer Res.* (2003) 1347-1353, 9(4).
Wen et al., "Potentiation of antitumor activity of PG-TXL with anti-EGFR monoclonal antibody C225 in MDA-MB-468 human breast cancer xenograft." *Proceedings of the American Association for Cancer Research* (2000) 323 (Abstract 2052), 51.
Weppler et al., "Expression of EGFR variant vIII promotes both radiation resistance and hypoxia tolerance." *Radiotherapy and oncology* (2007) 333-339, 83(3).
Wersäll et al., "Intratumoral infusion of the monoclonal antibody, mAb 425, against the epidermal-growth-factor receptor in patients with advanced malignant glioma." *Cancer Immunol. Immunother.* (1997) 157-164, 44(3).
Westwood et al., "Adoptive transfer of T cells modified with a humanized chimeric receptor gene inhibits growth of Lewis-Y-expressing tumors in mice." *Proceedings of the National Academy of Sciences of the United States of America* (2005) 19051-19056, 102(52).
Wheeler et al., "Mechanisms of acquired resistance to cetuximab: role of HER (ErbB) family members." *Oncogene* (2008) 3944-3956, 27(28).
Wheeler et al., "Epidermal growth factor receptor variant III mediates head and neck cancer cell invasion via STAT3 activation." *Oncogene* (2010) 5135-5145, 29(37).

Whitson et al., "Functional effects of glycosylation at Asn-579 of the epidermal growth factor receptor." *Biochemistry* (2005) 14920-14931, 44(45).
Wikstrand et al., "Antibodies and molecular immunology: immunohistochemistry and antigens of diagnostic significance" *In: Russell and Rubinstein's Pathology of Tumors of the Nervous System* (Chapter 8) (Editors: Biqner, et al.; Publishers: Arnold and Oxford University Press, Inc., New York, NY). (1998) 251-304.
Wikstrand et al., "Monoclonal antibody therapy of human gliomas: current status and future approaches." *Cancer Metastasis Rev.* (1999) 451-464, 18(4).
Wikstrand et al., "The class III variant of the epidermal growth factor receptor (EGFRvIII): characterization and utilization as an immunotherapeutic target." *Journal of neurovirology* (1998) 148-158, 4(2).
Wikstrand et al., "Cell surface localization and density of the tumor-associated variant of the epidermal growth factor receptor, EGFRvIII." *Cancer Res.* (1997) 4130-4140, 57(18).
Wikstrand et al., "Investigation of a synthetic peptide as immunogen for a variant epidermal growth factor receptor associated with gliomas." *Journal of neuroimmunology* (1993) 165-173, 46(1-2).
Wikstrand et al., "Comparative localization of glioma-reactive monoclonal antibodies in vivo in an athymic mouse human glioma xenograft model." *Journal of neuroimmunology* (1987) 37-56, 15(1).
Wikstrand et al., "Production and characterization of two human glioma xenograft-localizing monoclonal antibodies." *Cancer Res.* (1986) 5933-5940, 46(11).
Wiley et al., "The role of tyrosine kinase activity in endocytosis, compartmentation, and down-regulation of the epidermal growth factor receptor." *Journal of Biological Chemistry* (1991) 11083-11094, 266(17).
Wiley, "Trafficking of the ErbB receptors and its influence on signaling." *Exp. Cell Res.* (2003) 78-88, 284(1).
Willett et al., "Direct evidence that the VEGF-specific antibody bevacizumab has antivascular effects in human rectal cancer" *Nature Med.* (2004) 145-147, 10(2).
Williams et al., "Combination of ZD1839 ('Iressa'), an EGFR tyrosine kinase inhibitor, and radiotherapy increases antitumour efficacy in a human colon cancer xenograft model." *Proceedings of the American Association for Cancer Research* (2001) 715 (Abstract 3840), 42.
Williams et al., "ZD1839 ('Iressa'), a specific oral epidermal growth factor receptor-tyrosine kinase inhibitor, potentiates radiotherapy in a human colorectal cancer xenograft model." *British Journal of Cancer* (2002) 1157-1161, 86(7).
Winer et al., "New Combinations with Herceptin® in Metastatic Breast Cancer." *Oncology* (2001) 50-57, 61(Suppl. 2).
Winkler et al., "Epidermal growth factor and transforming growth factor alpha bind differently to the epidermal growth factor receptor." *Biochemistry* (1989) 6373-6378, 28(15).
Winter et al., "Man-made antibodies." *Nature* (1991) 293-299, 349(6307).
Wollman et al., "Effect of epidermal growth factor on the growth and radiation sensitivity of human breast cancer cells in vitro." *Int. J. Radiat. Oncol. Biol. Phys.* (1994) 91-98, 30(1).
Woltjer et al., "Direct identification of residues of the epidermal growth factor receptor in close proximity to the amino terminus of bound epidermal growth factor." *Proceedings of the National Academy of Sciences of the United States of America* (1992) 7801-7805, 89(16).
Wong et al., "Structural alterations of the epidermal growth factor receptor gene in human gliomas." *Proceedings of the National Academy of Sciences of the United States of America* (1992) 2965-2969, 89(7).
Wong et al., "Increased expression of the epidermal growth factor receptor gene in malignant gliomas is invariably associated with gene amplification." *Proceedings of the National Academy of Sciences of the United States of America* (1987) 6899-6903, 84(19).
Wood et al., "A unique structure for epidermal growth factor receptor bound to GW572016 (Lapatinib): relationships among protein conformation, inhibitor off-rate, and receptor activity in tumor cells." *Cancer Res.* (2004) 6652-6659, 64(18).

(56) References Cited

OTHER PUBLICATIONS

Woodburn et al., "ZD1839 ('Iressa') a Selective Epidermal Growth Factor Receptor Tyrosine Kinase Inhibitor (EGFR-TKI): Inhibition of CFOS MRNA, an Intermediate Marker of EGFR Activation Corre—Lates With Tumor Growth Inhibition." *Proceedings of the Annual Meeting of the American Association for Cancer Research* (2000) 402 (Abstract 2552), 41.
Woodburn et al., "ZD1839, an epidermal growth factor tyrosine kinase inhibitor selected for clinical development." *Proceedings of the Annual Meeting of the American Association for Cancer Research* (1997) 633 (Abstract 4251), 38.
Woodburn, "The epidermal growth factor receptor and its inhibition in cancer therapy." *Pharmacology & therapeutics* (1999) 241-250, 82(2-3).
Wu et al., "Human epidermal growth factor (EGF) receptor sequence recognized by EGF competitive monoclonal antibodies. Evidence for the localization of the EGF-binding site." *Journal of Biological Chemistry* (1989) 17469-17475, 264(29).
Wu et al., "Targeted delivery of methotrexate to epidermal growth factor receptor-positive brain tumors by means of cetuximab (IMC-C225) dendrimer bioconjugates." *Molecular cancer therapeutics* (2006) 52-59, 5(1).
Wu et al., "Humanization of a murine monoclonal antibody by simultaneous optimization of framework and CDR residues." *J. Mol. Biol.* (1999) 151-162, 294(1).
Wu et al., "Apoptosis induced by an anti-epidermal growth factor receptor monoclonal antibody in a human colorectal carcinoma cell line and its delay by insulin." *J. Clin. Invest.* (1995) 1897-1905, 95(4).
Xie et al., "In vitro invasiveness of DU-145 human prostate carcinoma cells is modulated by EGF receptor-mediated signals." *Clinical & experimental metastasis* (1995) 407-419, 13(6).
Xiong et al., "Cetuximab, a monoclonal antibody targeting the epidermal growth factor receptor, in combination with gemcitabine for advanced pancreatic cancer: a multicenter phase II Trial." *J. Clin. Oncol.* (2004) 2610-2616, 22(13).
Xu et al., "Antibody-induced growth inhibition is mediated through immunochemically and functionally distinct epitopes on the extracellular domain of the c-erbB-2 (HER-2/neu) gene product p185." *Int. J. Cancer* (1993) 401-408, 53(3).
Xu et al., "Characterization of epidermal growth factor receptor gene expression in malignant and normal human cell lines." *Proceedings of the National Academy of Sciences of the United States of America* (1984) 7308-7312, 81(23).
Xu et al., "Human epidermal growth factor receptor cDNA is homologous to a variety of RNAs overproduced in A431 carcinoma cells." *Nature* (1984) 806-810, 309(5971).
Yamanaka et al., "Coexpression of epidermal growth factor receptor and ligands in human pancreatic cancer is associated with enhanced tumor aggressiveness." *Anticancer research* (1993) 565-569, 13(3).
Yamazaki et al., "Inhibition of tumor growth by ribozyme-mediated suppression of aberrant epidermal growth factor receptor gene expression." *J. Natl. Cancer Inst.* (1998) 581-587, 90(8).
Yamazaki et al., "A deletion mutation within the ligand binding domain is responsible for activation of epidermal growth factor receptor gene in human brain tumors." *Japanese journal of cancer research : Gann* (1990) 773-779, 81(8).
Yamazaki et al., "Amplification of the structurally and functionally altered epidermal growth factor receptor gene (c-erbB) in human brain tumors." *Mol. Cell Biol.* (1988) 1816-1820, 8(4).
Yang et al., "Therapeutic potential of ABX-EGF, a fully human anti-EGF receptor monoclonal antibody, for cancer treatment." *Proceedings of the American Society of Clinical Oncology* (2000) 48a (Abstract 183), 19.
Yang et al., "Modification of Gemcitabine-Induced Radiosesitization by the Nitroxide Tempol." *Proceedings of the American Society of Clinical Oncology* (1999) 457a (Abstract 1765), 18.
Yang et al., "Genistein, a tyrosine kinase inhibitor, reduces EGF-induced EGF receptor internalization and degradation in human hepatoma HepG2 cells." *Biochem. Biophys. Res. Commun.* (1996) 309-317, 224(2).
Yang et al., "Identification and characterization of Ch806 mimotopes." *Cancer Immunology, Immunotherapy* (2010) 1481-1487, 59(10).
Yang et al., "Molecular targeting and treatment of EGFRvIII-positive gliomas using boronated monoclonal antibody L8A4." *Clin. Cancer Res.* (2006) 3792-3802, 12(12).
Yang et al., "Development of a syngeneic rat brain tumor model expressing EGFRvIII and its use for molecular targeting studies with monoclonal antibody L8A4." *Clin. Cancer Res.* (2005) 341-350, 11(1).
Yang et al., "Development of ABX-EGF, a fully human anti-EGF receptor monoclonal antibody, for cancer therapy." *Crit. Rev. Oncol. Hematol.* (2001) 17-23, 38(1).
Yang et al., "Eradication of established tumors by a fully human monoclonal antibody to the epidermal growth factor receptor without concomitant chemotherapy." *Cancer Res.* (1999) 1236-1243, 59(6).
Yao et al., "Enhanced expression of c-myc and epidermal growth factor receptor (C-erbB-1) genes in primary human renal cancer." *Cancer Res.* (1988) 6753-6757, 48(23).
Yarden et al., "Untangling the ErbB signalling network." *Nat. Rev. Mol. Cell Biol.* (2001) 127-137, 2(2).
Yarden et al., "Epidermal growth factor induces rapid, reversible aggregation of the purified epidermal growth factor receptor." *Biochemistry* (1987) 1443-1451, 26(5).
Yarden et al., "Self-phosphorylation of epidermal growth factor receptor: evidence for a model of intermolecular allosteric activation." *Biochemistry* (1987) 1434-1442, 26(5).
Ye et al., "Augmentation of a humanized anti-HER2 mAb 4D5 induced growth inhibition by a human-mouse chimeric anti-EGF receptor mAb C225." *Oncogene* (1999) 731-738, 18(3).
Yeatman, "A renaissance for SRC." *Nature Rev. Cancer* (2004) 470-480, 4(6).
Yen et al., "Differential regulation of tumor angiogenesis by distinct ErbB homo- and heterodimers." *Mol. Biol. Cell* (2002) 4029-4044, 13(11).
Yip et al., "Identification of epitope regions recognized by tumor inhibitory and stimulatory anti-ErbB-2 monoclonal antibodies: implications for vaccine design." *Journal of immunology* (Baltimore, Md : 1950) (2001) 5271-5278, 166(8).
Yip et al., "Structural analysis of the ErbB-2 receptor using monoclonal antibodies: Implications for receptor signalling." *Int. J. Cancer* (2003) 303-309, 104(3).
Ymer et al., "Glioma Specific Extracellular Missense Mutations in the First Cysteine Rich Region of Epidermal Growth Factor Receptor (EGFR) Initiate Ligand Independent Activation" *Cancers* (2011) 2032-2049, 3.
Ymer et al., "Constitutive synthesis of interleukin-3 by leukaemia cell line WEHI-3B is due to retroviral insertion near the gene." *Nature* (1985) 255-258, 317(6034).
Yoshida et al., "Studies of the expression of epidermal growth factor receptor in human renal cell carcinoma: a comparison of immunohistochemical method versus ligand binding assay." *Oncology* (1997) 220-225, 54(3).
Yoshida et al., "EGF and TGF-alpha, the ligands of hyperproduced EGFR in human esophageal carcinoma cells, act as autocrine growth factors." *Int. J. Cancer* (1990) 131-135, 45(1).
Yoshimoto et al., "Development of a real-time RT-PCR assay for detecting EGFRvIII in glioblastoma samples." *Clin. Cancer Res.* (2008) 488-493, 14(2).
Yoshitake et al., "Conjugation of Glucose Oxidase from *Aspergillus niger* and Rabbit Antibodies Using N-Hydroxysuccinimide Ester of N-(4-Carboxycyclohexylmethyl)-Maleimide" *Eur. J. Biochem.* (1979) 395-399, 101(2).
Yu et al., "Co-expression of EGFRvIII with ErbB-2 enhances tumorigenesis: EGFRvIII mediated constitutively activated and sustained signaling pathways, whereas EGF-induced a transient effect on EGFR-mediated signaling pathways." *Cancer biology & therapy* (2008) 1818-1828, 7(11).
Yu et al., "The biosynthetic gene cluster of the maytansinoid antitumor agent ansamitocin from Actinosynnema pretiosum." *Proceedings of the National Academy of Sciences of the United States of America* (2002) 7968-7973, 99(12).

(56) References Cited

OTHER PUBLICATIONS

Yu et al., "Ligand-independent dimer formation of epidermal growth factor receptor (EGFR) is a step separable from ligand-induced EGFR signaling." *Mol. Biol. Cell* (2002) 2547-2557, 13(7).
Zalutsky, "Growth factor receptors as molecular targets for cancer diagnosis and therapy." *The quarterly journal of nuclear medicine : official publication of the Italian Association of Nuclear Medicine (AIMN) [and] the International Association of Radiopharmacology (IAR)* (1997) 71-77, 41(2).
Zarcone et al., "Epidermal growth factor receptor expression: is it the same in normal and malignant endometria?" *Clinical and experimental obstetrics & gynecology* (1995) 298-300, 22(4).
Zhang et al., "Therapeutic monoclonal antibodies for the ErbB family of receptor tyrosine kinases." *Cancer biology & therapy* (2003) S122-6, 2(4; Suppl. 1).
Zhang et al., "Novel approaches to treatment of advanced colorectal cancer with anti-EGFR monoclonal antibodies." *Annals of medicine* (2006) 545-551, 38(8).
Zhang et al., "An allosteric mechanism for activation of the kinase domain of epidermal growth factor receptor." *Cell* (2006) 1137-1149, 125(6).
Zhen et al., "Characterization of glycosylation sites of the epidermal growth factor receptor." *Biochemistry* (2003) 5478-5492, 42(18).
Zhu et al., "Epidermal growth factor receptor: association of extracellular domain negatively regulates intracellular kinase activation in the absence of ligand." *Growth Factors* (2003) 15-30, 21(1).
Zhu et al., "EGFR tyrosine kinase inhibitor AG1478 inhibits cell proliferation and arrests cell cycle in nasopharyngeal carcinoma cells." *Cancer Letters* (2001) 27-32, 169(1).
Zinner et al., "A phase I clinical and biomarker study of the novel pan-erbB tyrosine kinase inhibitor, CI-1033, in patients with solid tumors." *Clinical Cancer Research* (2001) 3767s (Abstract 566), 7.
Mukohara et al. "Differential effects of getfitinib and cetuximab on EGFR mutant non-small cell lung cancers", Proc. Amerc. Assoc. Cancer Res., vol. 46, 2005.
Arteaga, C. L., "ErbB-targeted therapeutic approaches in human cancer . . . " *Exp. Cell Res.* (2003) 122-130, 284.
Avital et al., *Cancer* (2000) 1692-1698, 89(8).
Behr et al., *Cancer* (2002) 1373-1381, 94(4 Suppl.).
Bird et al., *Science* (1988) 423-426, 242.
Fisher et al., *Genes Dev.* (2001) 3249-3262, 15(24).
WO, PCT/US08/01024 Written Opinion, Aug. 1, 2008.
WO, PCT/US08/01024 International Search Report, Aug. 1, 2008.
Foulon et al., *Cancer Res.* (2000) 4453-4460, 60(16).
Gold et al., *Crit. Rev. Oncol. Hematol.* (2001) 147-154, 39(1-2).
Goldenberg, D.M., *Crit. Rev. Oncol. Hematol.* (2001) 195-201, 39(1-2).
Groner, B., C. Hartmann and W. Weis, *Therapeutic antibodies* (2004) 539-547, 4.
Haber et al., "Molecular targeted therapy of lung cancer: EGFR mutations and response to EGFR inhibitors . . . " *Cold Spring Harb. Symp. Quant. Biol.* (2005) 419-426, 70.
Halatsch, M.E., U. Schmidt, J. Behnke-Mursch, A. Unterberg and C.R. Wirtz, "Epidermal growth factor receptor inhibition for the treatment of glioblastoma multiforme and other malignant brain tumours . . . " *Cancer Treat. Rev.* (2006) 74-89, 32.
Herbst, R. S., "Targeted therapy in non-small-cell lung cancer." *Oncology* (2002) 19-24, 16.
Hills, D., G. Rowlinson-Busza and W. J. Gullick, "Specific targeting of a mutant, activated EGF receptor found in glioblastoma using a monoclonal antibody." *Int. J. Cancer* (1995) 537-543, 63.
Holliger et al., *PNAS* (1993) 6444-6448, 90.
Huston et al., *PNAS* (1988) 5879-5883, 85.
Hynes, N.E. and H. A. Lane, "ERBB receptors and cancer: the complexity of targeted inhibitors." *Nat. Rev. Cancer* (2005) 341-354, 5.
Italiano, A., "Targeting the epidermal growth factor receptor in colorectal cancer: advances and controversies." *Oncology* (2006) 161-167, 70.
Janne, P. A., J. A. Engelman and B. E. Johnson, "Epidermal growth factor receptor mutations in non-small-cell lung cancer: implications for treatment and tumor biology." *J. Clin. Oncol.* (2005) 3227-3234, 23.
Ji et al., "2006. Epidermal growth factor receptor variant III mutations in lung tumorigenesis and sensitivity to tyrosine kinase inhibitors . . . " *PNAS* (2006) 7817-7822, 103.
Ji et al., "The impact of human EGFR kinase domain mutations on lung tumorigenesis and in vivo sensitivity to EGFR-targeted therapies . . . " *Cancer Cell* (2006) 485-495, 9.
Ji et al., *Cell Cycle* (2006) 2072-2076, 5(18).
Johns, T. G., E. Stockert, G. Ritter, A. A. Jungbluth, H. J. Huang, W. K. Cavenee, F. E. Smyth, C. M. Hall, N. Watson, E. C. Nice, W. J. Gullick, L. J. Old, A. W. Burgess and A. M. Scott, "Novel monoclonal antibody specific for the DE2-7 Epidermal Growth Factor Receptor (EGFR) that also recognizes the EGFR expressed in cells containing amplification of the EGFR gene . . . " *Int. J. Cancer* (2002) 398-408, 98.
Johns, T.G., T.E. Adams, J.R. Cochran, N.E. Hall, P.A. Hoyne, M.J. Olsen, Y.S. Kim, J. Rothacker, E.C. Nice, F. Walker, G. Ritter, A.A. Jungbluth, L.J. Old, C.W. Ward, A.W. Burgess, K.D. Wittrup and A.M. Scott, "Identification of the Epitope for the EGFR-Specific Monoclonal Antibody 806 Reveals that it Preferentially Recognizes an Untethered Form of the Receptor." *J. Biol. Chem.* (2004) 30375-30384, 279(29).
Jungbluth, A. A., E. Stockert, H. J. Huang, V. P. Collins, K. Coplan, K. Iversen, D. Kolb, T. J. Johns, A. M. Scott, W. J. Gullick, G. Ritter, L. Cohen, M. J. Scanlan, W. K. Cavenee and L. J. Old, "A Monoclonal Antibody Recognizing Human Cancers with Amplification/Over-Expression of the Human Epidermal Growth Factor Receptor." *Proc. Natl. Acad. Sci. USA* (2003) 639-644, 100.
Kim et al., *Int. J. Cancer* (2002) 542-547, 97(4).
Kobayashi et al., "An alternative inhibitor overcomes resistance caused by a mutation of the epidermal growth factor receptor . . . " *Cancer Res.* (2005) 7096-7101, 65.
Kobayashi et al., "EGFR mutation and resistance of non-small-cell lung cancer to gefitinib." *N. Engl. J. Med.* (2005) 786-792, 352(8).
Kubo et al., "Three-dimensional magnetic resonance microscopy of pulmonary solitary tumors in transgenic mice." *Magn. Reson. Med.* (2006) 698-703, 56.
Kwak et al., *PNAS* (2005) 7665-7670, 102(21).
Li, Schmitz, Jeffrey, Wiltzius, Kussie and Ferguson, *Cancer Cell* (2005) 301-311, 7.
Luwor, R. B., T. G. Johns, C. Murone, H. J. Huang, W. K. Cavenee, G. Ritter, L. J. Old, A. W. Burgess and A. M. Scott, "Monoclonal Antibody 806 Inhibits the Growth of Tumor Xenografts Expressing Either the DE2-7 or Amplified Epidermal Growth Factor Receptor (EGFR) but not Wild-Type EGFR." *Cancer Res.* (2001) 5355-5361, 61.
Lynch et al., "Activating mutations in the epidermal growth factor receptor underlying responsiveness of non-small-cell lung cancer to gefitinib . . . " *N. Engl. J. Med.* (2004) 2129-2139, 350.
McIntosh et al., *Cancer Biother. Radiopharm.* (1997) 287-294, 12(4).
Mendelsohn, J. and J. Baselga, "The EGF receptor family as targets for cancer therapy." *Oncogene* (2000) 6550-6565, 19.
Mishima, K., T. G. Johns, R. B. Luwor, A. M. Scott, E. Stockert, A. A. Jungbluth, X. D. Ji, P. Suvarna, J. R. Voland, L. J. Old, H. J. Huang and W. K. Cavenee, "Growth Suppression of Intracranial Xenografted Glioblastomas Overexpressing Mutant Epidermal Growth Factor Receptors by Systemic Administration of Monoclonal Antibody (mAb) 806, a Novel Monoclonal Antibody Directed to the Receptor." *Cancer Res.* (2001) 5349-5354, 61.
Modjtahedi et al., *Cell Biophys.* (1993) 129-146, 22(1-3).
Okamoto, Yoshikawa, Obata, Shibuya, Aoki, Yoshida and Takahashi, "Monoclonal antibody against the fusion junction of a deletion-mutant epidermal growth factor receptor." *Br. J. Cancer* (1996) 1366-1372, 73.
Paez et al., "EGFR Mutations in Lung Cancer: Correlation with Clinical Response to Gefitinib Therapy . . . " *Science* (2004) 1497-1500, 304.
Panousis, C., V.M. Rayzman, T.G. Johns, C. Renner, Z. Liu, G. Cartwright, F.T. Lee, D. Wang, H. Gan, D. Cao, A. Kypridis, F.E. Smyth, M.W. Brechbiel, A.W. Burgess, L.J. Old and A.M. Scott,

(56) References Cited

OTHER PUBLICATIONS

"Engineering and characterisation of chimeric monoclonal antibody 806 (ch806) for targeted immunotherapy of tumours expressing de2-7 EGFR or amplified EGFR." *British Journal of Cancer* (2005) 1069-1077, 92(6).

Pao et al., *PNAS* (2004) 13306-13311, 101(36).

Park, K. and K. Goto, "A review of the benefit-risk profile of gefitinib in Asian patients with advanced non-small-cell lung cancer." *Curr. Med. Res. Opin.* (2006) 561-573, 22.

Pedersen, M. W. and H. S. Poulsen, "Mutations in the epidermal growth factor receptor: structure and biological function in human tumors." *Ugeskr. Laeger.* (2006) 2354-2361, 168.

Perl, A.K., J.W. Tichelaar and J.A. Whitsett, *Transgenic Res.* (2002) 21-29, 1(1).

Politi et al., "Lung adenocarcinomas induced in mice by mutant EGF receptors found in human lung cancers respond to a tyrosine kinase inhibitor or to down-regulation of the receptors." *Genes Dev.* (2006) 1496-1510, 20.

Power and Hudson, *J. Immunol. Methods* (2000) 193-204, 242.

Reist, Archer, Kurpad, Wikstrand, Vaidyanathan, Willingham, Moscatello, Wong, Bigner and Zalutsky, "Tumor-specific anti-epidermal growth factor receptor variant in monoclonal antibodies: use of the tyramine-cellobiose radio iodination method enhances cellular retention and uptake in tumor xenografts." *Cancer Res.*, (1995) 4375-4382, 55.

Reist, Archer, Wikstrand, Bigner and Zalutsky, "Improved targeting of an anti-epidermal growth factor receptor variant III monoclonal antibody in tumor xenografts after labeling using N-succinimidyl 5-iodo-3-pyridinecarboxylate." *Cancer Res.* (1997) 1510-1515, 57.

Sakurada, A., F.A. Shepherd and M.S. Tsao, "Epidermal growth factor receptor tyrosine kinase inhibitors in lung cancer: impact of primary or secondary mutations . . . " *Clin. Lung Cancer* (2006) S138-144, 7(Suppl. 4).

Schneebaum et al., *World J. Surg.* (2001) 1495-1498, 25(12).

Shigematsu, H. and A.F. Gazdar, "Somatic mutations of epidermal growth factor receptor signaling pathway in lung cancers." *Int. J. Cancer* (2006) 257-262, 118.

Snyder, L.C., L. Astsaturov and L.M. Weiner, "Overview of monoclonal antibodies and small molecules targeting the epidermal growth factor receptor pathway in colorectal cancer." *Clin. Colorectal Cancer* (2005) S71-80, 5(Suppl. 2).

Sok, Coppelli, Thomas, Lango, Xi, Hunt, Freilino, Graner, Wikstrand, Bigner, Gooding, Furnari and Grandis, *Clin. Cancer Res.* (2006) 5064-5073, 12.

Stein et al., *Cancer* (2002) 51-61, 94(1).

Ward et al., *Nature* (1989) 544-546, 341.

Wikstrand, C. J., L. P. Hale, S. K. Batra, M. L. Hill, P. A. Humphrey, S. N. Kurpad, R. E. McLendon, D. Moscatello, C. N. Pegram and C. J. Reist, "Monoclonal antibodies against EGFRvin are tumor specific and react with breast and lung carcinomas and malignant gliomas." *Cancer Res.* (1995) 3140-3148, 55.

Perez-Torres et al., "Epidermal growth factor receptor (EGFR) antibody down-regulates mutant receptors and inhibits tumors expressing EGFR mutations", *The Journal of Biological Chemistry*, 281(52):40183-40192, Dec. 2006.

\* cited by examiner

SEQUENCE LISTING

<160> NUMBER OF SEQ ID NOS: 3

<210> SEQ ID NO 1
<211> LENGTH: 116
<212> TYPE: PRT
<213> ORGANISM: Mus musculus

<400> SEQUENCE: 1

Asp Val Gln Leu Gln Glu Ser Gly Pro Ser Leu Val Lys Pro Ser Gln

```
                1               5                      10                       15
            Ser Leu Ser Leu Thr Cys Thr Val Thr Gly Tyr Ser Ile Thr Ser Asp
                            20                      25                      30

Phe Ala Trp Asn Trp Ile Arg Gln Phe Pro Gly Asn Lys Leu Glu Trp
                            35                      40                      45

Met Gly Tyr Ile Ser Tyr Ser Gly Asn Thr Arg Tyr Asn Pro Ser Leu
                            50                      55                      60

Lys Ser Arg Ile Ser Ile Thr Arg Asp Thr Ser Lys Asn Gln Phe Phe
             65                     70                      75                      80

Leu Gln Leu Asn Ser Val Thr Ile Glu Asp Thr Ala Thr Tyr Tyr Cys
                            85                      90                      95

Val Thr Ala Gly Arg Gly Phe Pro Tyr Trp Gly Gln Gly Thr Leu Val
                            100                     105                     110

Thr Val Ser Ala
                            115

<210> SEQ ID NO 2
<211> LENGTH: 108
<212> TYPE: PRT
<213> ORGANISM: Mus musculus

<400> SEQUENCE: 2

Asp Ile Leu Met Thr Gln Ser Pro Ser Ser Met Ser Val Ser Leu Gly
 1               5                      10                       15

Asp Thr Val Ser Ile Thr Cys His Ser Ser Gln Asp Ile Asn Ser Asn
                20                      25                      30

Ile Gly Trp Leu Gln Gln Arg Pro Gly Lys Ser Phe Lys Gly Leu Ile
                35                      40                      45

Tyr His Gly Thr Asn Leu Asp Asp Glu Val Pro Ser Arg Phe Ser Gly
                50                      55                      60

Ser Gly Ser Gly Ala Asp Tyr Ser Leu Thr Ile Ser Ser Leu Glu Ser
 65                     70                      75                      80

Glu Asp Phe Ala Asp Tyr Tyr Cys Val Gln Tyr Ala Gln Phe Pro Trp
                85                      90                      95

Thr Phe Gly Gly Gly Thr Lys Leu Glu Ile Lys Arg
                100                     105

<210> SEQ ID NO 3
<211> LENGTH: 13
<212> TYPE: PRT
<213> ORGANISM: Artificial Sequence
<220> FEATURE:
<223> OTHER INFORMATION: synthetic

<400> SEQUENCE: 3

Leu Glu Glu Lys Lys Gly Asn Tyr Val Val Thr Asp His
 1               5                      10
```

USE OF ANTI-EGFR ANTIBODIES IN TREATMENT OF EGFR MUTANT MEDIATED DISEASE

RELATED APPLICATIONS

This application is a 371 national phase application of International Application No. PCT/US2008/001024, filed on Jan. 24, 2008, which claims priority to U.S. Provisional Application No. 60/897,383, filed on Jan. 25,2007.

FIELD OF THE INVENTION

The present invention relates to the treatment of EGFR-mediated disease, particularly cancer, which is resistant to tyrosine kinase inhibitor therapies. Methods for treatment of cancer and reduction of tumor growth in individuals with secondary EGFR mutations, particularly tyrosine kinase domain mutations, resistant to standard therapy are provided.

BACKGROUND OF THE INVENTION

Targeted cancer therapy is designed to disrupt the function of specific molecules needed for carcinogenesis and tumor growth and thus either kills or prevents the growth of cancer cells (Ji H et al (2006) Cell Cycle 5(18):2072-2076 Epub 2006 Sep. 15). In contrast to conventional cytotoxic chemotherapy, such targeted cancer therapies may be more effective and less harmful to normal cells. A main effort in the targeted cancer therapy field has been the development of agents that target the epidermal growth factor receptor (EGFR). EGFR is a member of the ErbB family of closely related receptors including EGFR (ErbB-1), Her2/neu (ErbB-2), Her3 (ErbB-3) and Her4 (ErbB-4). Activation of EGFR leads to receptor tyrosine kinase activation and a series of downstream signaling events that mediate cellular proliferation, motility, adhesion, invasion, and resistance to chemotherapy as well as inhibition of apoptosis (2-4), processes that are crucial to the continual proliferation and survival of cancer cells.

To date, two major types of anti-EGFR agents have entered the clinical setting: anti-EGFR antibodies and small molecule EGFR tyrosine kinase inhibitors(TKIs) (5, 6). Anti-EGFR antibodies such as cetuximab were designed to bind to the extra-cellular domain of the EGFR and block activation of EGFR downstream signaling (7). Cetuximab (also known as antibody 225, U.S. Pat. No. 4,943,533) was raised against A431 cells, which express high levels of wild type EGFR. In contrast, small molecule TKIs such as gefitinib (compound ZD1839, Iressa) or erlotinib (compound OSI-774, Tarceva) compete with ATP for binding to the intracellular catalytic domain of the EGFR tyrosine kinase and, thus, prevent EGFR autophosphorylation and downstream signaling(4).

Both of these anti-EGFR drug groups have shown some clinical efficacy in a subset of patients with a variety of different types of cancers. Treatment with gefitinib or erlotinib in patients with lung cancer having EGFR kinase domain mutations often generate dramatic clinical responses (5, 8). However, the effectiveness of gefitinib or erlotinib in lung adenocarcinoma with wild type EGFR or in other histological subtype, such as squamous cell carcinoma is limited (9, 10). Furthermore, it has been shown in pre-clinical and clinical trials that gefitinib or erlotinib are largely ineffective in inhibiting the function of the EGFRvIII mutant (11), a distinct activating EGFR mutation in which there is an in-frame deletion of exon II to VII (also denoted EGFR de2-7). EGFRvIII is commonly found in glioblastomas and recently found to be present in a subset of human lung squamous cell carcinomas (12) and a large fraction of head and neck cancers (13).

Cetuximab is shown to be effective in a small subset of non-small cell lung cancer (NSCLC) patients, and patients with head and neck cancers, as well as colorectal cancer patients. However, the response to cetuximab does not seem to correlate with expression levels of EGFR. Thus, it is unclear why these patients respond while other cancer patients whose tumors have high EGFR expression are refractory to cetuximab treatment (14).

As expression of the EGFR vIII mutant receptor is restricted to tumor cells, it represents a highly specific target for antibody therapy. Accordingly, both polyclonal and monoclonal antibodies specific to the unique peptide of de2-7 EGFR have been generated. A series of mouse mAbs, isolated following immunization with the unique de2-7 peptide, all showed selectivity and specificity for the truncated receptor and targeted de2-7 EGFR positive xenografts grown in nude mice (Wikstrand C J et al (1995) Cancer Res 55:3140-3148; Okamoto, S et al (1996) Br J Cancer 73:1366-1372; Hills D et al (1995) Int J Cancer 63:537-543; Reist C J et al (1997) Cancer Res 57:1510-1515; Reist C J et al (1995) Cancer Res 55:4375-4382; U.S. Pat. No. 5,401,828). Examples of anti-EGFR viii antibodies include ABX-EGF (panitumumab), DH8.3, L8A.4, and Y10.

MAb806 is a novel murine antibody, originally raised to recognize the unique truncation mutant, EGFRvIII using whole cells expressing EGFR vIII mutant as immunogen (15-17). Importantly, the epitope recognized by mAb806 is not accessible in inactive wild-type (wt) EGFR, but is exposed in a transitional form of wt EGFR in cells with overexpression of EGFR, and expression of EGFRvIII (18). The epitope studies are supported by immunohistochemical studies demonstrating that the 806 antibody binds to epitopes present in gliomas, as well as a broad range of epithelial cancers, but not to normal human tissues (16, 19). These and other preclinical data suggest that mAb806 might have a different spectrum of clinical activity and side effect profile distinct from cetuximab and other anti-EGFR antibodies. In xenograft models, mAb806 has exhibited a potent anti-tumor activity with no targeting of normal tissues. Thus, the unique targeting capabilities of mAb806 represent a new paradigm for cancer-specific molecularly targeted therapy.

When overexpressed or activated by mutations, tyrosine kinases including EGFR contribute to the development of cancer and these mutated tyrosine kinase (TK) enzymes often provide a target or sensitivity for selective and specific cancer therapy. Somatic mutations in the tyrosine kinase domains of the EGFR gene are associated with sensitivity of lung cancers to certain tyrosine kinase inhibitors (TKIs) including gefitinib and erlotinib. In frame EGFR deletions in exon 19 (del L747-S752) and frequent point mutations in codon 858 (exon 21) (L858R) have been identified in non-small cell lung cancers and adenocarcinomas and associated with sensitivity to the TKIs gefitinib and erlotinib (Lynch T J et al (2004) N Engl J Med 350:2129-2139; Paez J G et al (2004) Science 304:1497-1500; Pao W et at (2004) PNAS 101(36):13306-13311). Recent studies have shown that 10-30% of NSCLC patients have EGFR kinase domain mutations while 5% of lung squamous cell carcinoma (SCC) patients have the extracellular domain EGFRvIII mutation (12, 20). Methods to determine the responsiveness of cancer to EGFR targeting treatments, based on assessment of mutations in EGFR, particularly in the kinase domain, and predicted inhibitor sensitivity in patients are described in Bell et al (WO 2005/094357 and US20060147959).

Acquired resistance to chemotherapy or targeted cancer therapy, mediated by secondary resistance or compensatory mutations is an ongoing challenge. Tumors that are sensitive to TKIs, including either gefitinib or erlotinib, eventually progress despite continued treatment with the TKIs. A secondary mutation at position 790 of EGFR (T790M) has been identified in tumor biopsy of relapsed and resistant patients (Kobayashi S et al (2005) N Engl J Med 352(8):786-792). This mutation is predicted to lead to steric hindrance of inhibitor binding in the ATP-kinase-binding pocket.

In view of the existence and prevalence of acquired resistance to TKIs in EGFR mediated disease and the significant cancer relapse rate, there is a clinical need for more broadly effective treatment protocols, employing EGFR targeted agents which are effective against, target, or avoid acquired resistance in EGFR mutants and EGFR mediated disease.

The citation of references herein shall not be construed as an admission that such is prior art to the present invention.

SUMMARY OF THE INVENTION

Activating epidermal growth factor receptor (EGFR) mutations have now been identified in a number of EGFR-mediated cancers, including lung cancer. EGFR mutations have been identified in human non-small cell lung cancer (NSCLC), with 5% of human lung squamous cell carcinomas having EGFRvIII mutations and 10~30% of lung adenocarcinomas having EGFR kinase domain mutations. The EGFR targeting monoclonal antibody, mAb806, recognizes a conformational epitope of wild type (wt) EGFR as well as the truncated EGFRvIII mutant. In an effort to further characterize the application of mAb806 to EGFR-mediated cancer therapy, mAb806 was used to treat genetically engineered mice with lung tumors that were driven by either EGFRvIII or EGFR kinase domain mutations. The present invention confirms that anti-EGFR vIII antibody, particularly mAb806, is remarkably effective in blocking EGFRvIII signaling and inducing tumor cell apoptosis, resulting in dramatic tumor regression in EGFRvIII driven murine lung cancers. A distinct EGFR-targeting antibody, raised to cells expressing high levels of wild type EGFR, cetuximab, failed to show activity in these genetically defined lung tumors. In addition, treatment of murine lung tumors driven by a recognized and clinically relevant EGFR kinase domain mutation (L858R) with mAb806 induced a significant tumor regression. This kinase domain mutation has been shown to be sensitive to TKI therapy, particularly gefitinib or erlotinib.

Acquired resistance to TKIs, including either gefitinib or erlotinib, is an ongoing challenge and tumors that are sensitive to TKIs eventually progress despite continued therapy. This acquired resistance can be mediated by secondary resistance or compensatory mutations, particularly including a secondary mutation at position 790 of EGFR (T790M). The investigators now show that anti-EGFR antibody, particularly mAb806, is effective against the T790M mutation, resulting in dramatic tumor regression in EGFR T790M/L858R driven murine lung cancers. Taken together, these data demonstrate that anti-EGFR antibody, particularly mAb806, provides an effective alternative or adjunct in the treatment of patients with EGFR kinase domain mutations, including cancer patients, particularly lung cancer patients.

The invention provides a method of treating tyrosine kinase inhibitor resistant EGFR-mediated disease in a mammal, wherein said resistant EGFR-mediated disease is a result of a secondary mutation in EGFR to generate a mutant EGFR and wherein said mutation is distinct from the EGFR vIII mutation, comprising administering to said mammal an effective amount of an anti-EGFR antibody capable of binding to and inhibiting the mutant EGFR. In a particular aspect the secondary EGFR mutation is an EGFR tyrosine kinase domain mutation. In a further aspect the tyrosine kinase domain mutation is T790M.

In a particular embodiment of the method the anti-EGFR antibody is mAb806 antibody or an active fragment thereof. MAb806 includes murine antibody, recombinant antibody or a humanized antibody.

Additional anti-EGFR antibodies, including those targeting the EGFRvIII mutant may be utilized in the therapeutic methods of the invention. Exemplary and known anti-EGFR antibodies may be selected from ABX-EGF (panitumumab), DH8.3, L8A4, and or active fragments thereof.

EGFR-mediated disease for treatment in the methods includes cancer. EGFR-mediated cancers include glioblastoma, head and neck cancer, pancreatic cancer, lung cancer, cancer of the nervous system, gastrointestinal cancer, prostate cancer, ovarian cancer, breast cancer, kidney cancer, retina cancer, skin cancer, liver cancer, genital-urinary cancer, and bladder cancer. In a particular aspect, the EGFR-mediated cancer is lung adenocarcinoma, lung squamous cell carcinoma or non-small cell lung cancer.

The invention provides a method for reducing EGFR-mediated tumor growth in a cancer patient, wherein said cancer patient has been previously treated with one or more tyrosine kinase inhibitor and has developed recurrent disease and tumor growth, comprising administering to said patient an effective amount of an anti-EGFR antibody such that the recurrent disease and tumor growth is inhibited and reduced.

In a particular embodiment of the method for reducing tumor growth the anti-EGFR antibody is mAb806 antibody or an active fragment thereof. MAb806 includes murine antibody, recombinant antibody or a humanized antibody.

Additional anti-EGFR antibodies, including those targeting the EGFRvIII mutant may be utilized. Exemplary and known anti-EGFR antibodies may be selected from ABX-EGF (panitumumab), DH8.3, L8A4, and or active fragments thereof.

In a particular clinical aspect, recurrent disease and tumor growth in the cancer patient is the result of a secondary EGFR mutation which is an EGFR tyrosine kinase domain mutation. A particular secondary EGFR mutation is the tyrosine kinase domain mutation T790M.

The invention further provides a method of treating EGFR-mediated cancer in a mammal comprising administering to said mammal a tyrosine kinase inhibitor and anti-EGFR antibody, wherein said anti-EGFR antibody is administered after treatment with the tyrosine kinase inhibitor as a second line of therapy to inhibit potential secondary mutant EGFRs resistant to tyrosine kinase inhibitors.

The EGFR-mediated cancer may be selected from glioblastoma, head and neck cancer, pancreatic cancer, lung cancer, cancer of the nervous system, gastrointestinal cancer, prostate cancer, ovarian cancer, breast cancer, kidney cancer, retina cancer, skin cancer, liver cancer, genital-urinary cancer, and bladder cancer. In particular the cancer is lung adenocarcinoma, lung squamous cell carcinoma or non-small cell lung cancer.

In one aspect of this method, the tyrosine kinase inhibitor is a reversible tyrosine kinase inhibitor. The reversible tyrosine kinase inhibitor may be an aniliniquinazoline and is selected from gefitinib, erlotinib, AG1478, ST1571 and SU-6668.

In a further aspect of this method, the tyrosine kinase inhibitor is an irreversible tyrosine kinase inhibitor. Exemplary irreversible tyrosine kinase inhibitor are known in the art and include, but are not limited to EKB-569, EKI-569, HKI-272, HKI-357 and BIBW 2992.

Other objects and advantages will become apparent to those skilled in the art from a review of the following description which proceeds with reference to the following illustrative drawings.

DETAILED DESCRIPTION

Figure 1:
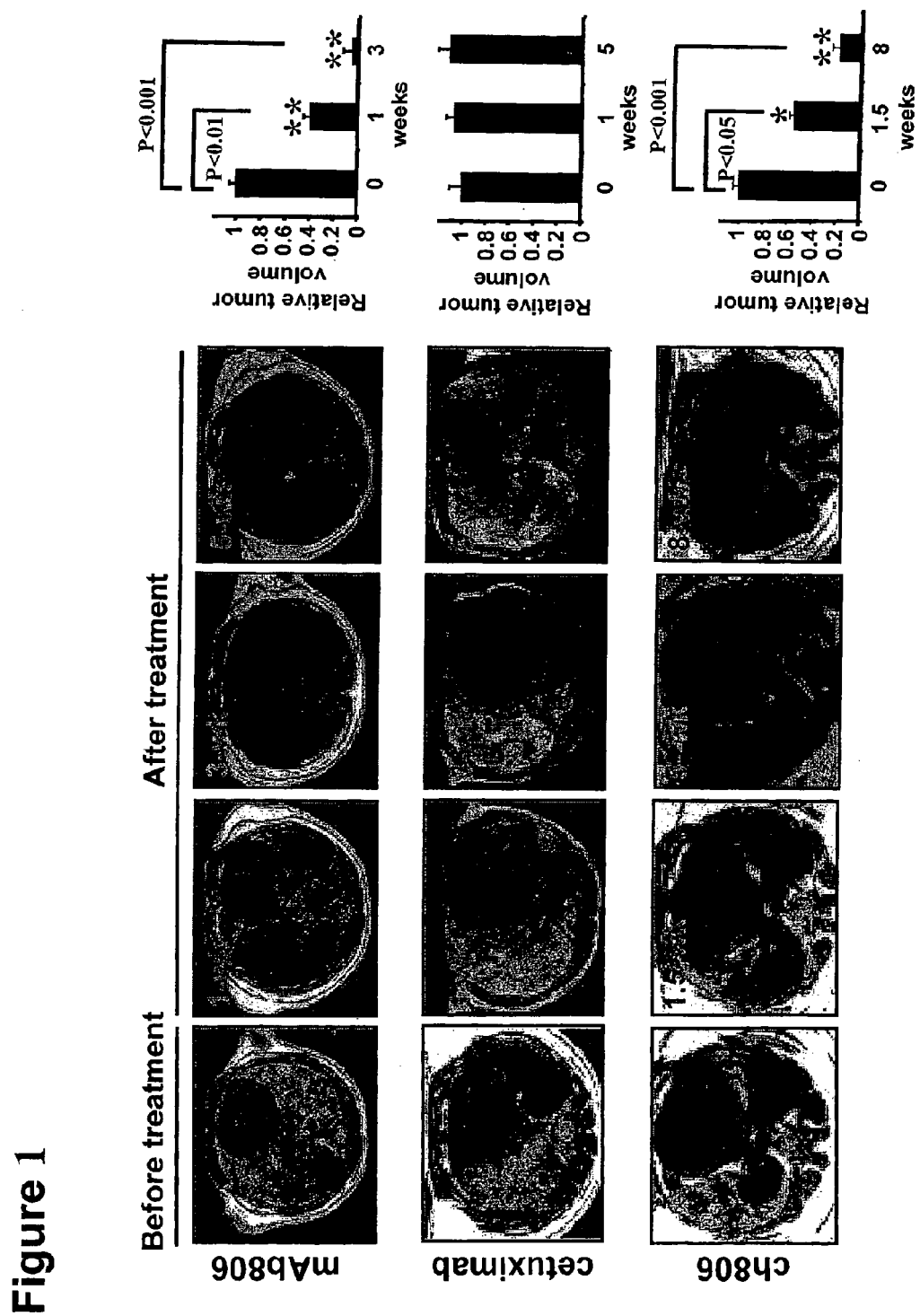
FIG. 1 depicts murine lung tumors driven by EGFRvIII expression are sensitive to mAb806 and ch806 antibody treatment but resistant to cetuximab treatment. Tet-op-EGFRvIII/CCSP-rtTA, Ink4A/Arf−/− mice were treated with either mAb806 or ch806 at 0.5 mg per dose or cetuximab at 1 mg per dose through daily I.P. injection. Antibodies were given every two days at the same dose after the first week of treatment. Serial MRI were performed at indicated time points, corresponding sections of representative mice in each treatment group are shown. Bar diagram expressed as mean±standard deviation (SD) illustrating the tumor regression measured by MRI, and statistical, analyses were performed using Student's exact t test. All mice were kept on a doxycycline diet throughout the experiment. H: indicates the area of the heart.

In accordance with the present invention there may be employed conventional molecular biology, microbiology, and recombinant DNA techniques within the skill of the art. Such techniques are explained fully in the literature. See, e.g., Sambrook et al, "Molecular Cloning: A Laboratory Manual" (1989); "Current Protocols in Molecular Biology" Volumes I-III [Ausubel, R. M., ed. (1994)]; "Cell Biology: A Laboratory Handbook" Volumes I-III [J. E. Celis, ed. (1994))]; "Current Protocols in Immunology" Volumes I-III [Coligan, J. E., ed. (1994)]; "Oligonucleotide Synthesis" (M. J. Gait ed. 1984); "Nucleic Acid Hybridization" [B. D. Hames & S. J. Higgins eds. (1985)]; "Transcription And Translation" [B. D. Hames & S. J. Higgins, eds. (1984)]; "Animal Cell Culture" [R. I. Freshney, ed. (1986)]; "Immobilized Cells And Enzymes" [IRL Press, (1986)]; B. Perbal, "A Practical Guide To Molecular Cloning" (1984).

Therefore, if appearing herein, the following terms shall have the definitions set out below.

The term "antibody" describes an immunoglobulin whether natural or partly or wholly synthetically produced. Antibody includes any immunoglobulin, including antibodies and fragments thereof, that binds a specific epitope. The term encompasses polyclonal, monoclonal, recombinant, humanized, and chimeric antibodies. The term also covers any polypeptide or protein having a binding domain which is, or is homologous to, an antibody binding domain. CDR grafted antibodies are also contemplated by this term.

As antibodies can be modified in a number of ways, the term "antibody" should be construed as covering any specific binding member or substance having a binding domain with the required specificity. Thus, this term covers antibody fragments, derivatives, functional equivalents and homologues of antibodies, including any polypeptide comprising an immunoglobulin binding domain, whether natural or wholly or partially synthetic. Chimeric molecules comprising an immunoglobulin binding domain, or equivalent, fused to another polypeptide are therefore included. Cloning and expression of chimeric antibodies are described in EP-A-0120694 and EP-A-0125023 and U.S. Pat. Nos. 4,816,397 and 4,816,567.

It has been shown that fragments of a whole antibody can perform the function of binding antigens. Examples of binding fragments are (i) the Fab fragment consisting of VL, VH, CL and CH1 domains; (ii) the Fd fragment consisting of the VH and CH1 domains; (iii) the Fv fragment consisting of the VL and VH domains of a single antibody; (iv) the dAb fragment (Ward, E. S. et al., Nature 341, 544-546 (1989)) which consists of a VH domain; (v) isolated CDR regions; (vi) F(ab')2 fragments, a bivalent fragment comprising two linked Fab fragments (vii) single chain Fv molecules (scFv), wherein a VH domain and a VL domain are linked by a peptide linker which allows the two domains to associate to form an antigen binding site (Bird et al, Science, 242, 423-426, 1988; Huston et al, PNAS USA, 85, 5879-5883, 1988); (viii) multivalent antibody fragments (scFv dimers, trimers and/or tetramers (Power and Hudson, J. Immunol. Methods 242: 193-204 9 (2000))(ix) bispecific single chain Fv dimers. (PCT/US92/09965) and (x) "diabodies", multivalent or multispecific fragments constructed by gene fusion (WO94/13804; P. Holliger et al Proc. Natl. Acad. Sci. USA 90 6444-6448, (1993)).

An "antibody combining site" is that structural portion of an antibody molecule comprised of light chain or heavy and light chain variable and hypervariable regions that specifically binds antigen.

The phrase "antibody molecule" in its various grammatical forms as used herein contemplates both an intact immunoglobulin molecule and an immunologically active portion of an immunoglobulin molecule.

Exemplary antibody molecules are intact immunoglobulin molecules, substantially intact immunoglobulin molecules and those portions of an immunoglobulin molecule that contains the paratope, including those portions known in the art as Fab, Fab', F(ab')$_2$ and F(v), which portions are preferred for use in the therapeutic methods described herein.

Antibodies may also be bispecific, wherein one binding domain of the antibody is a specific binding member of the invention, and the other binding domain has a different specificity, e.g. to recruit an effector function or the like. Bispecific antibodies of the present invention include wherein one binding domain of the antibody is a specific binding member of the present invention, including a fragment thereof, and the other binding domain is a distinct antibody or fragment thereof, including that of a distinct anti-EGFR antibody, for instance antibody 528 (U.S. Pat. No. 4,943,533), the chimeric and humanized 225 antibody (U.S. Pat. No. 4,943,533 and WO/9640210), an anti-del-7 antibody such as DH8.3 (Hills, D. et al (1995) Int. J. Cancer 63(4):537-543), antibody L8A4 and Y10 (Reist, C J et al (1995) Cancer Res. 55(19):4375-4382; Foulon C F et al. (2000) Cancer Res. 60(16):4453-4460), ICR62 (Modjtahedi H et al (1993) Cell Biophys. January-June; 22(1-3):129-46; Modjtahedi et al (2002) P.A.A.C.R. 55(14):3140-3148, or the antibody of Wikstrand et al (Wikstrand C. et al (1995) Cancer Res. 55(14):3140-3148). The other binding domain may be an antibody that recognizes or targets a particular cell type, as in a neural or glial cell-specific antibody. In the bispecific antibodies of the present invention the one binding domain of the antibody of the invention may be combined with other binding domains or molecules which recognize particular cell receptors and/or modulate cells in a particular fashion, as for instance an immune modulator (e.g., interleukin(s)), a growth modulator or cytokine (e.g. tumor necrosis factor (TNF), and particularly, the TNF bispecific modality demonstrated in U.S. Ser. No. 60/355,838 filed Feb. 13, 2002 incorporated herein in its entirety) or a toxin (e.g., ricin) or anti-mitotic or apoptotic agent or factor.

Fab and F(ab')$_2$ portions of antibody molecules may be prepared by the proteolytic reaction of papain and pepsin, respectively, on substantially intact antibody molecules by methods that are well-known. See for example, U.S. Pat. No. 4,342,566 to Theofilopolous et al. Fab' antibody molecule portions are also well-known and are produced from F(ab')$_2$ portions followed by reduction of the disulfide bonds linking the two heavy chain portions as with mercaptoethanol, and followed by alkylation of the resulting protein mercaptan with a reagent such as iodoacetamide. An antibody containing intact antibody molecules is preferred herein.

The phrase "monoclonal antibody" in its various grammatical forms refers to an antibody having only one species of antibody combining site capable of immunoreacting with a particular antigen. A monoclonal antibody thus typically displays a single binding affinity for any antigen with which it immunoreacts. A monoclonal antibody may also contain an antibody molecule having a plurality of antibody combining sites, each immunospecific for a different antigen; e.g., a bispecific (chimeric) monoclonal antibody.

The term "antigen binding domain" describes the part of an antibody which comprises the area which specifically binds to and is complementary to part or all of an antigen. Where an antigen is large, an antibody may bind to a particular part of the antigen only, which part is termed an epitope. An antigen binding domain may be provided by one or more antibody variable domains. Preferably, an antigen binding domain comprises an antibody light chain variable region (VL) and an antibody heavy chain variable region (VH).

The terms "mAb806", "806 antibody", "monoclonal antibody 806", "ch806", "humanized 806" and any variants not specifically listed, may be used herein interchangeably, and as used throughout the present application and claims refer to Accordingly, antibodies, including recombinant, chimeric, genetically modified, or alternative antibodies, displaying substantially equivalent or altered activity are likewise contemplated. These modifications may be deliberate, for example, such as modifications obtained through site-directed mutagenesis, or may be accidental, such as those obtained through mutations in hosts that are producers of the antibody or its fragments. Also, the terms "mAb806", "806 antibody", "monoclonal antibody 806", "ch806", "humanized 806" are intended to include within their scope proteins and immunoglobulins specifically recited herein and known to the skilled artisan, publicly disclosed, as well as all substantially homologous analogs and allelic variations. The mAb806 antibody, including its generation, particular activities, amino acid and nucleic acid sequence, antigen binding domains, variable region sequences, are disclosed and known to the skilled artisan, including as provided in WO 02/092771; Luwor R B et al (2001) Cancer Res 61:5355-5361; Mishima K et al (2001) Cancer Res 61:5349-5354; Johns T G et al (2002) Int J Cancer 98:398-408; Jungbluth A A et al (2003) Proc Natl Acad Sci 100(2):639-644, each of which is incorporated by reference herein in its entirety.

The amino acid residues described herein are preferred to be in the "L" isomeric form. However, residues in the "D" isomeric form can be substituted for any L-amino acid residue, as long as the desired functional property of immunoglobulin-binding is retained by the polypeptide. NH$_2$ refers to the free amino group present at the amino terminus of a polypeptide. COOH refers to the free carboxy group present at the carboxy terminus of a polypeptide. In keeping with standard polypeptide nomenclature, *J. Biol. Chem.*, 243:3552-59 (1969), abbreviations for amino acid residues are shown in the following Table of Correspondence:

TABLE OF CORRESPONDENCE

| SYMBOL | | |
|---|---|---|
| 1-Letter | 3-Letter | AMINO ACID |
| Y | Tyr | tyrosine |
| G | Gly | glycine |
| F | Phe | phenylalanine |
| M | Met | methionine |
| A | Ala | alanine |
| S | Ser | serine |
| I | Ile | isoleucine |
| L | Leu | leucine |
| T | Thr | threonine |
| V | Val | valine |
| P | Pro | proline |
| K | Lys | lysine |
| H | His | histidine |
| Q | Gln | glutamine |
| E | Glu | glutamic acid |
| W | Trp | tryptophan |
| R | Arg | arginine |
| D | Asp | aspartic acid |
| N | Asn | asparagine |
| C | Cys | cysteine |

It should be noted that all amino-acid residue sequences are represented herein by formulae whose left and right orientation is in the conventional direction of amino-terminus to carboxy-terminus. Furthermore, it should be noted that a dash at the beginning or end of an amino acid residue sequence indicates a peptide bond to a further sequence of one or more amino-acid residues. The above Table is presented to correlate the three-letter and one-letter notations which may appear alternately herein.

It should be appreciated that also within the scope of compositions for use in the methods of the present invention are DNA sequences encoding and/or expressing effective anti-EGFR antibodies, particularly including mAb806 and ch806, which code for anti-EGFR antibodies, antigen binding domains thereof, or active fragments thereof having the same amino acid sequence as the mAb806 antibody as publicly disclosed and known to the skilled artisan, but which are degenerate to the known mAb806 sequence(s). By "degenerate to" is meant that a different three-letter codon is used to specify a particular amino acid. It is well known in the art that the following codons can be used interchangeably to code for each specific amino acid:

| | |
|---|---|
| Phenylalanine (Phe or F) | UUU or UUC |
| Leucine (Leu or L) | UUA or UUG or CUU or CUC or CUA or CUG |
| Isoleucine (Ile or I) | AUU or AUC or AUA |
| Methionine (Met or M) | AUG |
| Valine (Val or V) | GUU or GUC of GUA or GUG |
| Serine (Ser or S) | UCU or UCC or UCA or UCG or AGU or AGC |
| Proline (Pro or P) | CCU or CCC or CCA or CCG |
| Threonine (Thr or T) | ACU or ACC or ACA or ACG |
| Alanine (Ala or A) | GCU or GCG or GCA or GCG |
| Tyrosine (Tyr or Y) | UAU or UAC |
| Histidine (His or H) | CAU or CAC |
| Glutamine (Gln or Q) | CAA or CAG |
| Asparagine (Asn or N) | AAU or AAC |
| Lysine (Lys or K) | AAA or AAG |
| Aspartic Acid (Asp or D) | GAU or GAC |
| Glutamic Acid (Glu or E) | GAA or GAG |
| Cysteine (Cys or C) | UGU or UGC |
| Arginine (Arg or R) | CGU or CGC or CGA or CGG or AGA or AGG |
| Glycine (Gly or G) | GGU or GGC or GGA or GGG |
| Tryptophan (Trp or W) | UGG |
| Termination codon | UAA (ochre) or UAG (amber) or UGA (opal) |

It should be understood that the codons specified above are for RNA sequences. The corresponding codons for DNA have a T substituted for U.

Mutations can be made in anti-EGFR antibody sequence, including in mAb806 antibody sequence, such that a particular codon is changed to a codon which codes for a different amino acid. Such a mutation is generally made by making the fewest nucleotide changes possible. A substitution mutation of this sort can be made to change an amino acid in the resulting protein in a non-conservative manner (i.e., by changing the codon from an amino acid belonging to a grouping of amino acids having a particular size or characteristic to an amino acid belonging to another grouping) or in a conservative manner (i.e., by changing the codon from an amino acid belonging to a grouping of amino acids having a particular size or characteristic to an amino acid belonging to the same grouping). Such a conservative change generally leads to less change in the structure and function of the resulting protein. A non-conservative change is more likely to alter the structure, activity or function of the resulting protein. The present invention should be considered to include sequences containing conservative changes which do not significantly alter the activity or binding characteristics of the resulting immunoglobulin and antibody.

Similarly, it is anticipated that certain EGFR mutations, which may effect or alter, even significantly, the activity of EGFR, for instance the EGFR kinase domain mutations described and utilized herein, may not affect the recognition, binding or inhibition of EGFR by anti-EGFR antibodies, particularly including anti-EGFR vIII mutant antibodies, particularly including the mAb806 antibody. Thus, it is anticipated that mAb806 may be similarly effective against other, as yet unrecognized or as yet unknown, EGFR mutations, particularly secondary mutations which arise during anti-cancer therapy. These mutations may arise as a result of TM inhibition therapy or as a result of other therapies against EGFR-mediated disease which may target kinase or other activities of EGFR.

Amino acids may be grouped as similar or different, conserved or non-conserved. The grouping of amino acids may be based on their R groups (for instance nonpolar, uncharged polar, charged polar, those with phenyl groups), based on their molecular weight or the size of their R groups, and based on molecular weight. Particularly preferred substitutions are: Lys for Arg and vice versa such that a positive charge may be maintained; Glu for Asp and vice versa such that a negative charge may be maintained; Ser for Thr such that a free —OH can be maintained; and Gln for Asn such that a free NH$_2$ can be maintained.

Amino acid substitutions may also be introduced to substitute an amino acid with a particularly preferable property. For example, a Cys may be introduced a potential site for disulfide bridges with another Cys. A H is may be introduced as a particularly "catalytic" site (i.e., His can act as an acid or base and is the most common amino acid in biochemical catalysis). Pro may be introduced because of its particularly planar structure, which induces β-turns in the protein's structure.

Two amino acid sequences are "substantially homologous" when at least about 70% of the amino acid residues (preferably at least about 80%, and most preferably at least about 90 or 95%) are identical, or represent conservative substitutions.

The phrase "pharmaceutically acceptable" refers to molecular entities and compositions that are physiologically tolerable and do not typically produce an allergic or similar untoward reaction, such as gastric upset, dizziness and the like, when administered to a human.

The phrase "therapeutically effective amount" is used herein to mean an amount sufficient to prevent, and preferably reduce by at least about 20 percent, more preferably by at least 30 percent, still more preferably by at least 50 percent, more preferably by at least 70 percent, more preferably by at least 90 percent, a clinically significant change in the S phase activity of a target cellular mass, or a significant change in the size or dimensions of a target cellular mass or tumor, or other feature of pathology as may attend its presence and activity.

The antibody or active fragment can be formulated into the therapeutic composition as neutralized pharmaceutically acceptable salt forms. Pharmaceutically acceptable salts include the acid addition salts (formed with the free amino groups of the polypeptide or antibody molecule) and which are formed with inorganic acids such as, for example, hydrochloric or phosphoric acids, or such organic acids as acetic, oxalic, tartaric, mandelic, and the like. Salts formed from the free carboxyl groups can also be derived from inorganic bases such as, for example, sodium, potassium, ammonium, calcium, or ferric hydroxides, and such organic bases as isopropylamine, trimethylamine, 2-ethylamino ethanol, histidine, procaine, and the like.

The therapeutic antibody or active fragment-containing compositions are conventionally administered intravenously, as by injection of a unit dose, for example. The term "unit dose" when used in reference to a therapeutic composition of the present invention refers to physically discrete units suitable as unitary dosage for humans, each unit containing a predetermined quantity of active material calculated to produce the desired therapeutic effect in association with the required diluent; i.e., carrier, or vehicle.

The compositions are administered in a manner compatible with the dosage formulation, and in a therapeutically effective amount. The quantity to be administered depends on the subject to be treated, capacity of the subject's immune system to utilize the active ingredient, and degree of inhibition desired or extent of tumor mass being targeted. Precise amounts of active ingredient required to be administered depend on the judgment of the practitioner and are peculiar to each individual. However, suitable dosages may range from about 0.1 to 20, preferably about 0.5 to about 10, and more preferably one to several, milligrams of active ingredient per kilogram body weight of individual per day and depend on the route of administration. Suitable regimes for initial administration and booster shots are also variable, but are typified by an initial administration followed by repeated doses at one or more hour intervals by a subsequent injection or other administration. Alternatively, continuous intravenous infusion sufficient to maintain concentrations of ten nanomolar to ten micromolar in the blood are contemplated.

As used herein, "pg" means picogram, "ng" means nanogram, "ug" or "µg" mean microgram, "mg" means milligram, "ul" or "µl" mean microliter, "ml" means milliliter, "l" means liter.

In an effort to further characterize the application of mAb806 to EGFR-mediated cancer therapy, the present invention describes the use of mAb806 to treat genetically engineered mice with lung tumors that were driven by either EGFRvIII or EGFR kinase domain mutations. Each of these mutations are clinically relevant and significant for EGFR-mediated disease, particularly cancers, including lung cancer, pancreatic cancer, colorectal cancer, head and neck cancer, and glioblastoma. The present invention confirms that anti-EGFR vIII antibody, particularly mAb806, is remarkably effective in blocking EGFRvIII signaling and inducing tumor cell apoptosis, resulting in dramatic tumor regression in EGFRvIII driven murine lung cancers. A distinct EGFR-targeting antibody, raised to cells expressing high levels of wild type EGFR, cetuximab, failed to show activity in these genetically defined lung tumors. In addition, treatment of murine lung tumors driven by a recognized and clinically relevant EGFR kinase domain mutation (L858R) with mAb806 induced a significant tumor regression. This kinase domain mutation has been shown to be sensitive to TKI therapy, particularly gefitinib or erlotinib. Acquired resistance to TKIs including either gefitinib or erlotinib, is an ongoing challenge and tumors that are sensitive to TKIs eventually progress despite continued. This acquired resistance can be mediated by secondary resistance or compensatory mutations, particularly a secondary mutation at position 790 of EGFR (T790M). The investigators now show that anti-EGFR antibody, particularly mAb806 is effective against the T790M mutation, resulting in dramatic tumor regression in EGFR T790M/L858R driven murine lung cancers. Taken together, these data demonstrate that anti-EGFR antibody, particularly mAb806, provides an effective alternative or adjunct in the treatment of patients with EGFR kinase domain mutations, including cancer patients, particularly lung cancer patients.

Thus, both therapeutic and diagnostic applications and methods are provided and raised by the demonstration of the anti tumor activity of anti-EGFR antibody, particularly of mAb806. As suggested earlier and elaborated further on herein, the present invention contemplates pharmaceutical intervention in the cascade of reactions and signaling in which EGFR is implicated, to modulate the tumorigenic capacity associated with EGFR mutations, including kinase domain mutations, both primary and secondary resistant mutations.

The data provided herein demonstrate mAb806 activity against EGFR kinase domain mutations, including L858R and TKI resistant T790M. It is anticipated that further kinase domain mutations or EGFR secondary mutations may exist or will arise with continued and advancing directed anti-EGFR therapy. The irreversible inhibitor HKI272, which binds to EGFR at cysteine 797 (corresponding to cysteine 530 in EGFR vIII deletion mutants), is advancing in preclinical protocols. Resistant secondary mutations with substitutions at the cysteine are likely if not anticipated. These additional EGFR secondary mutants would be candidates for anti-EGFR antibody therapy.

The invention thus provides a method of treating tyrosine kinase inhibitor resistant EGFR-mediated disease in a mammal, wherein said resistant EGFR-mediated disease is a result of a secondary mutation in EGFR to generate a mutant EGFR and wherein said mutation is distinct from the EGFR vIII mutation, comprising administering to said mammal an effective amount of an anti-EGFR antibody capable of binding to and inhibiting the mutant EGFR. In a particular aspect the secondary EGFR mutation is an EGFR tyrosine kinase domain mutation. In a further aspect the tyrosine kinase domain mutation is T790M. In a particular embodiment of the method the anti-EGFR antibody is mAb806 antibody or an active fragment thereof. MAb806 includes murine antibody, recombinant antibody or a humanized antibody. Additional anti-EGFR antibodies, including those targeting the EGFRvIII mutant may be utilized in the therapeutic methods of the invention. Exemplary and known anti-EGFR antibodies may be selected from ABX-EGF (panitumumab), DH8.3, L8A4, and or active fragments thereof.

EGFR-mediated disease for treatment is particularly cancer and may be selected from glioblastoma, head and neck cancer, pancreatic cancer, lung cancer, cancer of the nervous system, gastrointestinal cancer, prostate cancer, ovarian cancer, breast cancer, kidney cancer, retina cancer, skin cancer, liver cancer, genital-urinary cancer, and bladder cancer. In a particular aspect, the EGFR-mediated cancer is lung adenocarcinoma, lung squamous cell carcinoma or non-small cell lung cancer.

The invention includes a method for reducing EGFR-mediated tumor growth in a cancer patient, wherein said cancer patient has been previously treated with one or more tyrosine kinase inhibitor and has developed recurrent disease and tumor growth, comprising administering to said patient an effective amount of an anti-EGFR antibody such that the recurrent disease and tumor growth is inhibited and reduced. In a particular embodiment of the method for reducing tumor growth the anti-EGFR antibody is mAb806 antibody or an active fragment thereof. MAb806 includes murine antibody, recombinant antibody or a humanized antibody. Additional anti-EGFR antibodies, including those targeting the EGFRvIII mutant may be utilized. Exemplary and known anti-EGFR antibodies may be selected from ABX-EGF (panitumumab), DH8.3, L8A4, and or active fragments thereof.

In a particular clinical aspect, recurrent disease and tumor growth in the cancer patient is the result of a secondary EGFR mutation which is an EGFR tyrosine kinase domain mutation. A particular secondary EGFR mutation is the tyrosine kinase domain mutation T790M.

The invention further provides a method of treating EGFR-mediated cancer in a mammal comprising administering to said mammal a tyrosine kinase inhibitor and anti-EGFR antibody. In one aspect, the tyrosine kinase inhibitor and anti-EGFR antibody are administered simultaneously. In one aspect, the tyrosine kinase inhibitor and anti-EGFR antibody are administered simultaneously or serially and repeatedly, before or after traditional chemotherapy.

The invention further provides a method of treating EGFR-mediated cancer in a mammal comprising administering to said mammal a tyrosine kinase inhibitor and anti-EGFR antibody, wherein said anti-EGFR antibody is administered after treatment with the tyrosine kinase inhibitor as a second line of therapy to inhibit potential secondary mutant EGFRs resistant to tyrosine kinase inhibitors.

The tyrosine kinase inhibitor may be a reversible tyrosine kinase inhibitor or an irreversible tyrosine kinase inhibitor. The reversible tyrosine kinase inhibitor may be an aniliniquinazoline and selected from gefitinib, erlotinib, AG1478, ST1571 and SU-6668. Exemplary irreversible tyrosine kinase inhibitor are known in the art and include, but are not limited to EKB-569, EKI-569, HKI-272, HKI-357 and BIBW 2992 (Kwak E L et al (2005) Proc Natl Acad Sci USA 102(21):7665-70).

EGFR-mediated cancers may be selected from glioblastoma, head and neck cancer, pancreatic cancer, lung cancer, cancer of the nervous system, gastrointestinal cancer, prostate cancer, ovarian cancer, breast cancer, kidney cancer, retina cancer, skin cancer, liver cancer, genital-urinary cancer, and bladder cancer. In particular the cancer is lung adenocarcinoma, lung squamous cell carcinoma or non-small cell lung cancer.

The anti-EGFR antibody, particularly mAb806 may be administered in the methods alone or in combination with other anti-EGFR antibodies. Thus, Mab806 may be administered serially or in combination with cetuximab. MAb806 may also be administered serially or in combination with other anti-EGFR vIII antibodies, including ABX-EGF (panitumumab), DH8.3, L8A4, and or active fragments thereof.

The anti-EGFR antibody(ies) may be prepared in pharmaceutical compositions, with a suitable carrier and at a strength effective for administration by various means to a patient. A variety of administrative techniques may be utilized, among them parenteral techniques such as subcutaneous, intravenous and intraperitoneal injections, catheterizations and the like. Quantities of the antibody or their active fragments may vary and in particular should be based upon the recommendations and prescription of a qualified physician or veterinarian, including upon consideration of the results and data provided herein.

The anti-EGFR antibodies of use in the invention, including mAb806, may provide useful diagnostic applications, including imaging applications or diagnostic biopsy applications, for diagnosing and/or monitoring cancer patients, including after or upon conclusion of TKI therapy.

The labels commonly employed for these studies are radioactive elements, enzymes, chemicals which fluoresce when exposed to ultraviolet light, and others. A number of fluorescent materials are known and can be utilized as labels. These include, for example, fluorescein, rhodamine, auramine, Texas Red, AMCA blue and Lucifer Yellow.

Antibodies of the invention may be labeled with a detectable or functional label. Detectable labels include, but are not limited to, radiolabels such as the isotopes $^{3}$H, $^{14}$C, $^{32}$P, $^{35}$S, $^{36}$Cl, $^{51}$Cr, $^{57}$Co, $^{58}$Co, $^{59}$Fe, $^{90}$Y, $^{121}$I, $^{124}$I, $^{125}$I, $^{131}$I, $^{111}$In, $^{211}$At, $^{198}$Au, $^{67}$Cu, $^{225}$Ac, $^{213}$Bi, $^{99}$Tc and $^{186}$Re, which may be attached to antibodies of the invention using conventional chemistry known in the art of antibody imaging. Labels also include fluorescent labels and labels used conventionally in the art for MRI-CT imagine. They also include enzyme labels such as horseradish peroxidase. Labels further include chemical moieties such as biotin which may be detected via binding to a specific cognate detectable moiety, e.g. labeled avidin.

Functional labels include substances which are designed to be targeted to the site of a tumor to cause destruction of tumor tissue. Such functional labels include cytotoxic drugs such as 5-fluorouracil or ricin and enzymes such as bacterial carboxypeptidase or nitroreductase, which are capable of converting prodrugs into active drugs at the site of a tumor.

The radiolabeled anti-EGFR antibodies and fragments thereof, are useful in in vitro diagnostics techniques and in in vivo radioimaging techniques and in radioimmunotherapy. In the instance of in vivo imaging, the specific binding members of the present invention may be conjugated to an imaging agent rather than a radioisotope(s), including but not limited to a magnetic resonance image enhancing agent, wherein for instance an antibody molecule is loaded with a large number of paramagnetic ions through chelating groups. Examples of chelating groups include EDTA, porphyrins, polyamines crown ethers and polyoximes. Examples of paramagnetic ions include gadolinium, iron, manganese, rhenium, europium, lanthanium, holmium and ferbium. In a further aspect of the invention, radiolabelled specific binding members, particularly antibodies and fragments thereof, particularly radioimmunoconjugates, are useful in radioimmunotherapy, particularly as radiolabelled antibodies for cancer therapy. In a still further aspect, the radiolabelled specific binding members, particularly antibodies and fragments thereof, are useful in radioimmuno-guided surgery techniques, wherein they can identify and indicate the presence and/or location of cancer cells, precancerous cells, tumor cells, and hyperproliferative cells, prior to, during or following surgery to remove such cells.

Immunoconjugates or antibody fusion proteins of the present invention, wherein the specific binding members, particularly antibodies and fragments thereof, of the present invention are conjugated or attached to other molecules or agents further include, but are not limited to binding members conjugated to a chemical ablation agent, toxin, immunomodulator, cytokine, cytotoxic agent, chemotherapeutic agent or drug.

Radioimmunotherapy (RAIT) has entered the clinic and demonstrated efficacy using various antibody immunoconjugates. $^{131}$I labeled humanized anti-carcinoembryonic antigen (anti-CEA) antibody hMN-14 has been evaluated in colorectal cancer (Behr T M et al (2002) Cancer 94(4Suppl):1373-81) and the same antibody with $^{90}$Y label has been assessed in medullary thyroid carcinoma (Stein R et al (2002) Cancer 94(1):51-61). Radioimmunotherapy using monoclonal antibodies has also been assessed and reported for non-Hodgkin's lymphoma and pancreatic cancer (Goldenberg DM (2001) Crit. Rev Oncol Hematol 39(1-2):195-201; Gold D V et al (2001) Crit. Rev Oncol Hematol 39 (1-2) 147-54). Radioimmunotherapy methods with particular antibodies are also described in U.S. Pat. Nos. 6,306,393 and 6,331,175. Radioimmunoguided surgery (RIGS) has also entered the clinic and demonstrated efficacy and usefulness, including using anti-CEA antibodies and antibodies directed against tumor-associated antigens (Kim J C et al (2002) Int J Cancer 97(4):542-7; Schneebaum S et al (2001) World J Surg 25(12):1495-8; Avital S et al (2000) Cancer 89(8):1692-8; McIntosh D G et al (1997) Cancer Biother Radiopharm 12 (4):287-94).

Antibodies of the present invention may be administered to a patient in need of treatment via any suitable route, usually by injection into the bloodstream or CSF, or directly into the site of the tumor. The precise dose will depend upon a number of factors, including whether the antibody is for diagnosis or for treatment, the size and location of the tumor, the precise nature of the antibody (whether whole antibody, fragment, diabody, etc), and the nature of the detectable or functional label attached to the antibody. Where a radionuclide is used for therapy, a suitable maximum single dose is about 45 mCi/m$^2$, to a maximum of about 250 mCi/m$^2$. Preferable dosage is in the range of 15 to 40 mCi, with a further preferred dosage range of 20 to 30 mCi, or 10 to 30 mCi. Such therapy may require bone marrow or stem cell replacement. A typical antibody dose for either tumor imaging or tumor treatment will be in the range of from 0.5 to 40 mg, preferably from 1 to 4 mg of antibody in F(ab')$_2$ form. Naked antibodies are preferable administered in doses of 20 to 1000 mg protein per dose, or 20 to 500 mg protein per dose, or 20 to 100 mg protein per dose. This is a dose for a single treatment of an adult patient, which may be proportionally adjusted for children and infants, and also adjusted for other antibody formats in proportion to molecular weight. Treatments may be repeated at daily, twice-weekly, weekly or monthly intervals, at the discretion of the physician.

The invention may be better understood by reference to the following non-limiting Examples, which are provided as exemplary of the invention. The following examples are presented in order to more fully illustrate the preferred embodiments of the invention and should in no way be construed, however, as limiting the broad scope of the invention.

EXAMPLE 1

Therapeutic Anti-EGFR Antibody 806 Generates Responses in Murine De Novo EGFR Mutant-dependant Lung Carcinomas Activating epidermal growth factor receptor (EGFR) mutations occur in human non-small cell lung cancer (NSCLC), with 5% of human lung squamous cell carcinomas having EGFRvIII mutations and 10~30% of lung adenocarcinomas having EGFR kinase domain mutations. An EGFR targeting monoclonal antibody, mAb806, recognizes a conformational epitope of wild type (wt) EGFR as well as the truncated EGFRvIII mutant. To explore the anticancer spectrum of this antibody for EGFR targeted cancer therapy, mAb806 was used to treat genetically engineered mice with lung tumors that were driven by either EGFRvIII or EGFR kinase domain mutations. Our results demonstrate that mAb806 is remarkably effective in blocking EGFRvIII signaling and inducing tumor cell apoptosis and, thus resulting in dramatic tumor regression in the EGFRvIII driven murine lung cancers. Another EGFR-targeting antibody, cetuximab, failed to show activity in these genetically defined lung tumors. Furthermore, treatment of murine lung tumors driven by EGFR kinase domain mutation with the mAb806 induced a significant tumor regression, albeit to a less degree than that observed in EGFRvIII driven tumors. Taken together, these data support the hypothesis that mAb806 may provide significant activity in the treatment of the population of NSCLC patients with these two classes of EGFR mutations. Hybridoma 806, which produces mAb806, was deposited with the American Type Culture Collection (10801 University Blvd., Manassas, Va. 20110-2209) on Nov. 4, 2001, under the provisions of the Budapest Treaty on the International Recognition of the Deposit of Microorganisms for the Purposes of Patent Procedures, and assigned accession numbers PTA-3858.

Introduction

Targeted cancer therapy is designed to disrupt the function of specific molecules needed for carcinogenesis and tumor growth and thus either kills or prevents the growth of cancer cells (1). In contrast to conventional cytotoxic chemotherapy, such targeted cancer therapies may be more effective and less harmful to normal cells. A main effort in the targeted cancer therapy field has been the development of agents that target the epidermal growth factor receptor (EGFR). EGFR is a member of the ErbB family of closely related receptors including EGFR (ErbB-1), Her2/neu (ErbB-2), Her3 (ErbB-3) and Her4 (ErbB-4). Activation of EGFR leads to receptor tyrosine kinase activation and a series of downstream signaling events that mediate cellular proliferation, motility, adhesion, invasion, and resistance to chemotherapy as well as inhibition of apoptosis (2-4), processes that are crucial to the continual proliferation and survival of cancer cells.

To date, two major types of anti-EGFR agents have entered the clinical setting: anti-EGFR antibodies and small molecule EGFR tyrosine kinase inhibitors (TKIs) (5, 6). Anti-EGFR antibodies such as cetuximab were designed to bind to the extra-cellular domain of the EGFR and block activation of EGFR downstream signaling (7). In contrast, small molecule TKIs such as gefitinib or erlotinib compete with ATP for binding to the intracellular catalytic domain of the EGFR tyrosine kinase and, thus, prevent EGFR autophosphorylation and downstream signaling (4).

Both of these anti-EGFR drug groups have shown some clinical efficacy in a subset of patients with a variety of different types of cancers. Treatment with gefitinib or erlotinib in patients with lung cancer having EGFR kinase domain mutations often generate dramatic clinical responses (5, 8). However, the effectiveness of gefitinib or erlotinib in lung adenocarcinoma with wild type EGFR or in other histological subtype, such as squamous cell carcinoma is limited (9, 10). Furthermore, it has been shown in pre-clinical and clinical trials that gefitinib or erlotinib are largely ineffective in inhibiting the function of the EGFRvIII mutant (11), a distinct activating EGFR mutation in which there is an in-frame deletion of exon II to VII. EGFRvIII is commonly found in glioblastomas and recently found to be present in a subset of human lung squamous cell carcinomas (12) and a large fraction of head and neck cancers (13). Cetuximab is shown to be effective in a small subset of non-small cell lung cancer (NSCLC) patients, and patients with head and neck cancers, as well as colorectal cancer patients. However, the response to cetuximab does not seem to correlate with expression levels of EGFR. Thus, it is unclear why these patients respond while other cancer patients whose tumors have high EGFR expression are refractory to cetuximab treatment (14).

MAb806 is a novel murine antibody, originally raised to recognize the unique truncation mutant, EGFRvIII (15-17). Importantly, the epitope recognized by mAb806 is not accessible in inactive wild-type (wt) EGFR, but is exposed in a transitional form of wt EGFR in cells with overexpression of EGFR, and expression of EGFRvIII (18). The epitope studies are supported by immunohistochemical studies demonstrating that the 806 antibody binds to epitopes present in gliomas, as well as a broad range of epithelial cancers, but not to normal human tissues (16, 19). These and other preclinical data suggest that mAb806 might have a different spectrum of clinical activity and side effect profile distinct from cetuximab and other anti-EGFR antibodies. In xenograft models, mAb806 has exhibited a potent anti-tumor activity with no targeting of normal tissues. Thus, the unique targeting capabilities of mAb806 represent a new paradigm for cancer-specific molecularly targeted therapy.

Recent studies have shown that 10-30% of NSCLC patients have EGFR kinase domain mutations while 5% of lung squamous cell carcinoma (SCC) patients have the extracellular domain EGFRvIII mutation (12, 20). To investigate the clinical potential of mAb806 in cancer-specific targeted therapy in NSCLC patients harboring EGFR mutations, we utilized two established mouse lung cancer models that are dependent on EGFRvIII or EGFR kinase domain mutants. Our data show that mAb806 is very effective in the treatment of murine NSCLC driven by expression of either EGFRvIII or EGFR kinase domain mutation and suggest that this antibody is likely to have clinical activity in patients whose tumors have similar mutation.

Results

Figure 2:
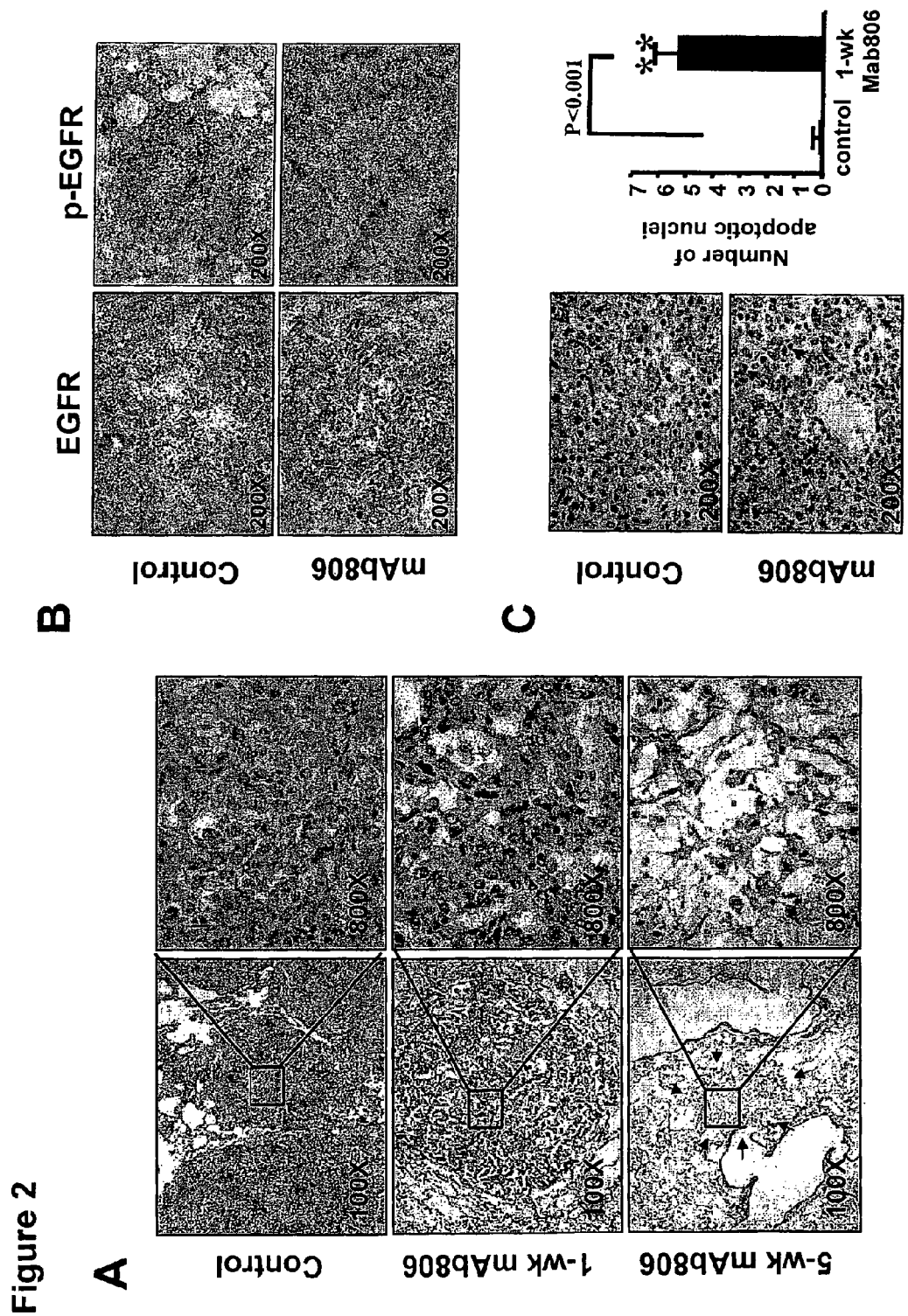
FIGS. 2A and 2B depicts histolopathological features of lung adenocarcinomas in EGFRvIII-driven mice treated with mAb806. (A) Lung adenocarcinoma driven by EGFRvIII expression for more than 8 weeks (upper panel). After 1 week of treatment with mAb806, tumors became smaller and had increased fibrosis (middle panel). Lung specimens were grossly normal when mAb806 treatment ended at 5 weeks (lower panel). Arrows show a fibrotic nodule, consisting of fibroblasts and macrophages. No tumor cells were found in this particular fibrosis area. Left panel: 100×, right panel: 800×. (B) Similar patterns and intensities of immunohistological staining of total EGFR can be observed in control mice and mice treated with mAb806 for 1 week (left upper and lower panel, respectively); intensity of phospho-EGFR staining of tumor cells decreased after 1 week of treatment (right lower panel) when compared with untreated tumors (right upper panel). Representative photos are taken under 200× magnification. (C) TUNEL staining shows increased apoptotic nuclei (red arrows) in EGFRvIII driven lung tumors after 1 week of treatment with mAb806 (left lower panel) when compared with untreated tumors (left upper panel). Representative photos are taken under 200× magnification. Bar diagrams expressed as mean±SD illustrating the apoptotic indices in lung tumors before and after 1 week of mAb806 treatment were determined from at least 200 high-power fields (HPF). Statistical analyses were performed using Student's exact t test (right panel).

Treatment with mAb806, but not Cetuximab, Induces Tumor Regression in Mice Bearing Lung Tumors with EGFRvIII Mutation Previous studies have established the essential role of EGFRvIII mutation in tumor maintenance of murine lung tumors driven by the mutation. Blocking EGFRvIII activation results in dramatic tumor regression associated with apoptosis in the de novo murine lung cancer model(12). Tet-op-EGFRvIII/CCSP-rtTA, Ink4A/Arf−/− mice developed lung adenocarcinomas with bronchiolalvealor carcinoma (BAC) features after 8-10 weeks of doxycycline administration, (FIG. 1, left panel; FIG. 2A, upper panel). After tumor bearing mice were identified by MRI, 0.5 mg per dose of mAb806 was given by intraperitoneally (I.P.) injection daily for the first week and then every two days for the next 4 weeks. Serial MRI was performed at the end of 1, 3 and 5 weeks of treatment to determine changes in tumor volume and/or density. Tumor reduction was notable by MRI after 1 week of mAb806 treatment (average reduction of 60%±5% among 6 mice, FIG. 1, upper panel). Tumor burden continued to decrease after 3 weeks of treatment (average reduction of 95%±8%), and all 6 mice had complete tumor regression after 5 weeks of treatment. In contrast, treatment of mice with cetuximab was unable to induce tumor regression in 4 Tet-op-EGFRvIII/CCSP-rtTA, Ink4A/Arf−/− mice even after 5 weeks of treatment at 1 mg per mouse with the same dosing schedule. We also observed that the mice treated with cetuximab became progressively frailer and that some even succumbed because of significant tumor burden during the treatment period (data not shown).

Pathologic examination of lungs from these mice correlated with the MRI findings: a decrease in tumor cellularity was present in adenocarcinomas after one week of treatment with mAb806 (FIG. 2A, middle panel). After 5 weeks, lungs had focal fibrosis and scaring, with sparse monocytic cell infiltrates; potentially representing areas of continuing remodeling from regressed tumors (FIG. 2A, lower panel). Although alive cancer cells could still be rarely observed in several foci of these fibrotic nodules, most of fibrosis and scarring area did not contain any tumor cells. In contrast, the tumors from mice treated with cetuximab appeared to be unaffected, with no visible histological difference when compared with untreated tumors (data not shown). Thus, treatment with mAb806 antibody led to rapid and dramatic tumor regression in the EGFRvIII driven mouse lung cancer model while cetuximab treatment was largely ineffective.

Figure 3:
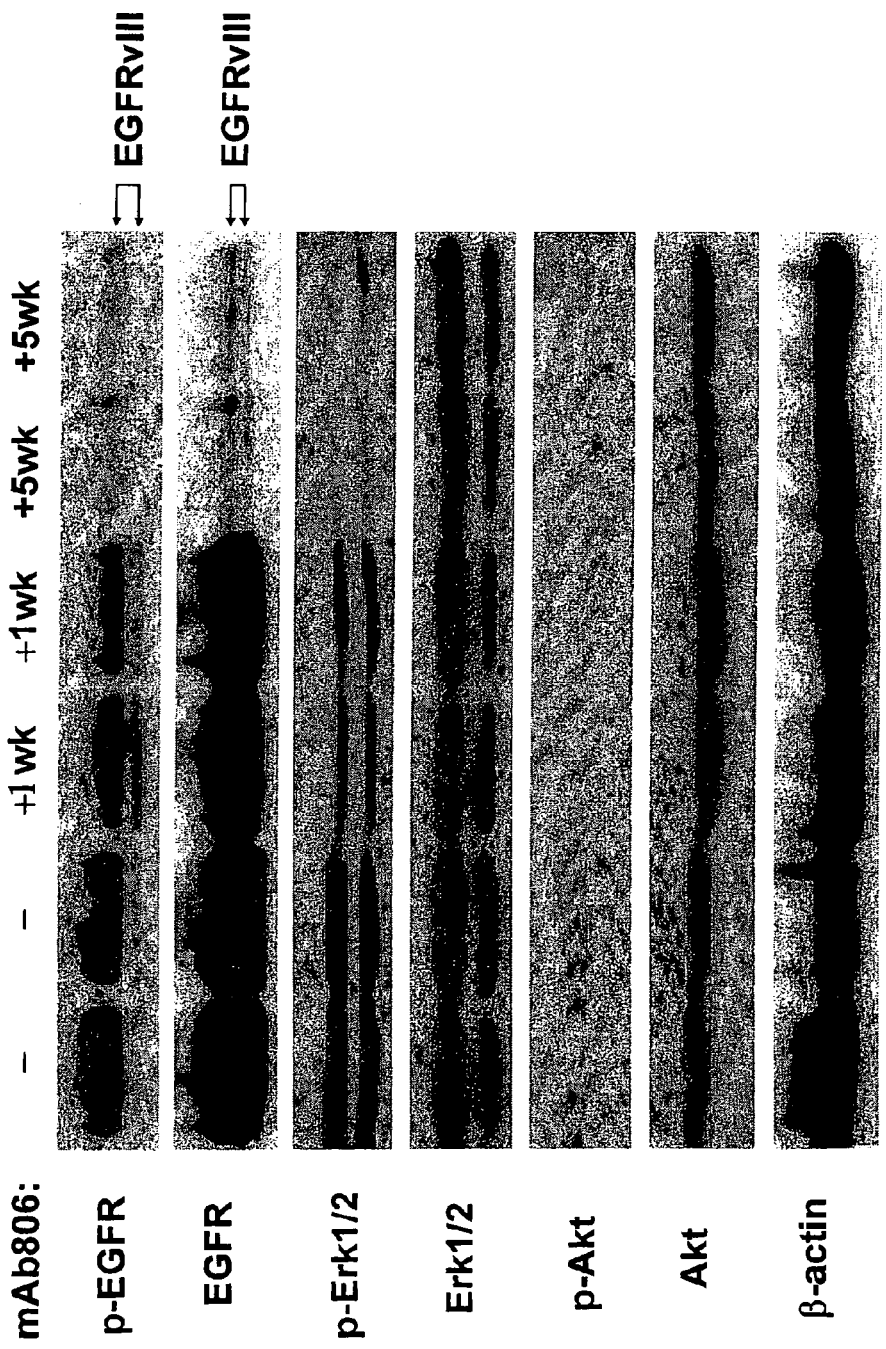
FIG. 3 shows Western blot analysis of whole lung lysate from mAb806 treated Tet-op-EGFRvIII/CCSP-rtTA, Ink4A/Arf−/− mice. Whole lung lysates from tumors taken from mice at different time points of mAb806 treatment were analyzed. Inhibition of EGFR phosphorylation can be observed as soon as after 1 week of treatment, while total EGFR level decreases only after 5 weeks of treatment. Erk1,2 phosphorylation was inhibited by the antibody throughout the mAb806 administration, but AKT phosphorylation remained at a level comparable to untreated controls at both treatment time points. β-actin serves as a loading control.

MAb806 Inhibits EGFRvIII Phosphorylation and Induces Apoptosis of Tumor Cells in Tet-op-EGFRvIII/CCSP-rtTA, Ink4A/Arf−/− Mice To determine whether the mAb806 that was administered intraperitoneally recognized its target in the lung tumors, we performed immunohistochemical staining in lung tumors of mice treated with or without mAb806 using antibodies against total EGFR and phospho-EGFR. As expected, mAb806 treatment had no impact on the total EGFRvIII expression in tumor cells, (FIG. 2B). However, the expression of phospho-EGFRvIII diminished after 1-week of mAb806 treatment (FIG. 2B). We next confirmed these findings by immunoblotting analysis using lung lysates collected at different time points during treatment with mAb806. The level of phospho-EGFRvIII decreased dramatically after 1-week mAb806 treatment while the total EGFRvIII level remained similar to that of untreated controls (FIG. 3), indicating a strong inhibitory effect of mAb806 on EGFRvIII phosphorylation. Interestingly, the total EGFRvIII level did finally decrease after 5 weeks of mAb806 administration. One explanation for this could be the dramatic decrease of the number of viable tumor cells. Consistent with this interpretation, greatly increased TUNEL staining was observed in lung tumors after 1-week of mAb806 treatment compared to untreated tumors (FIG. 2C). Besides the changes on phospho-EGFR level, 1 week of mAb806 treatment also decreased phospho-AKt and phospho-Erk-1,2 expression, these EGFR downstream signaling molecules are functionally associated with anti-apoptosis and proliferation pathways. Surprisingly, we observed a weak but reproducible increase of phopho-AKt level after 5 weeks of mAb806 treatment when compared to 1 week treatment. This phosphorylation of Akt is unlikely initiated by EGFRvIII, as phospho-EGFRvIII is low at this time point. Possibly, Akt could be activated by other signaling events that were involved in lung remodeling process. These data suggest that mAb806 induced tumor regression in EGFRvIII mice by blocking EGFR activation and increasing tumor cell apoptosis.

Ch806 Treatment Leads to a Dramatic Tumor Regression in Murine Lung Tumors with EGFRvIII Mutation Ch806 is a humanized form of mAb806 (22). To determine whether the humanized antibody could be as efficient as the murine mAb806 in treatment of lung adenocarcinoma in vivo, we treated tumor-bearing Tet-op-EGFRvIII/CCSP-rtTA, -Ink4A/Arf-/- mice with one dose of 0.5 mg of ch806 by I.P. injection daily for the first week and then one dose every two days for another 7 weeks. These mice underwent re-imaging at 1.5, 5 and 8 weeks of the treatment and were then sacrificed for histological analysis. We observed a dramatic reduction in tumor volume by MRI scanning starting from 1.5 weeks of the treatment (43%±3%), and near complete tumor regression (83%±7%) was achieved at 8 weeks of treatment in each of the 4 mice being treated with ch806 (FIG. 1, lower panel). The histology of mice treated with ch806 (data not shown) was similar to that of tumors after mAb806 treatment and was consistent with the MRI data.

Ch806 is Effective in Treatment of Murine Lung Tumors with EGFR L858R Mutation

Figure 4:
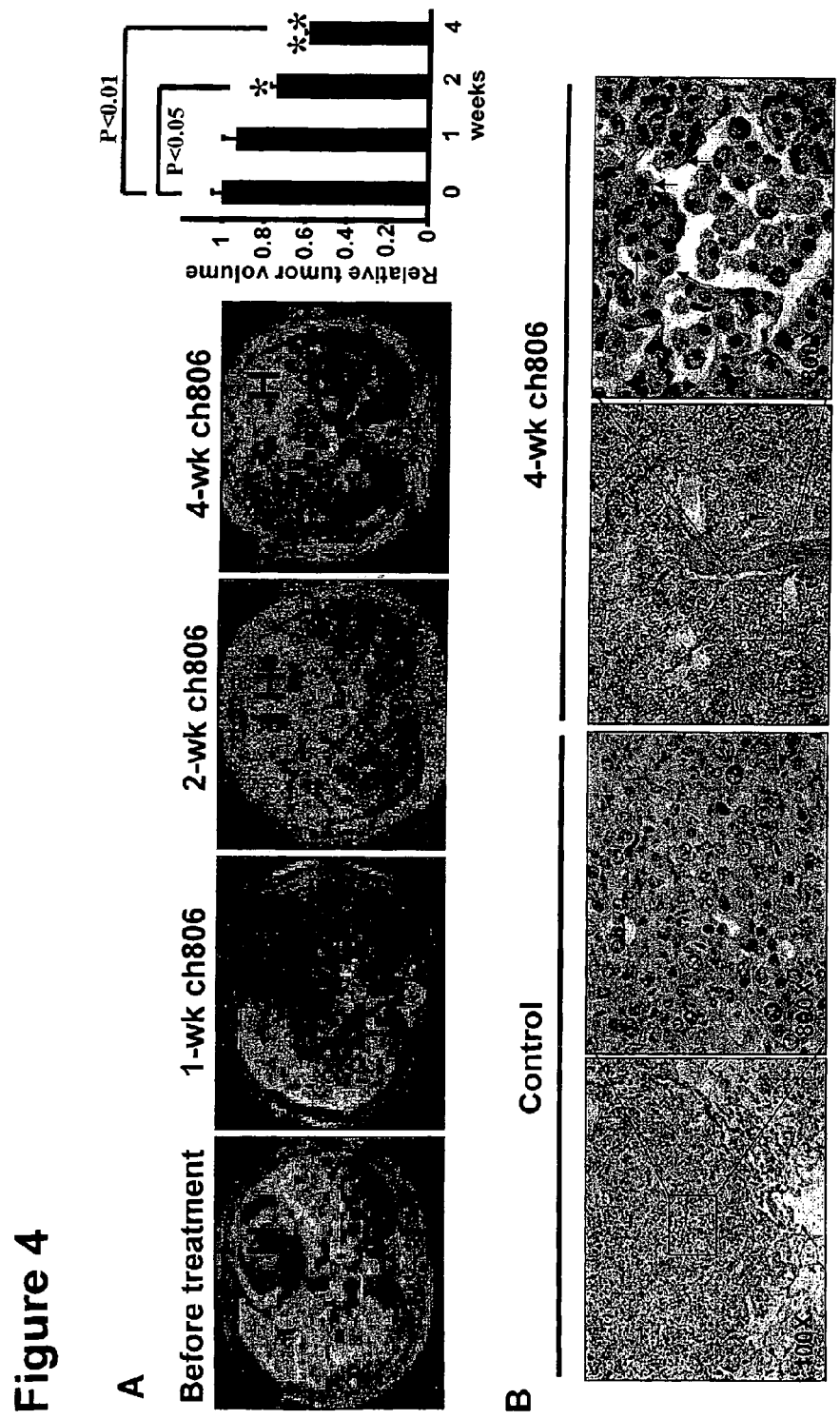
FIGS. 4A and 4B. EGFR kinase domain mutation L858R-driven mouse lung adenocarcinoma responds to ch806 treatment. (A) Tet-op-EGFR L858R-IRES-Luciferase/CCSP-rtTA mice were treated with ch806 at 0.5 mg per dose by daily I.P. injection for 4 weeks. MRI showed decreased tumor volume after 2 and 4 weeks of treatment. Bar diagram expressed as mean±SD illustrating the tumor regression measured by MRI, and statistical analyses were performed using Student's exact t test. H: indicates the area of the heart. (B) Histopathological analysis shows shrinkage of tumors and marked macrophage infiltration in Tet-op-EGFR L858R-IRES-Luciferase/CCSP-rtTA mice (right two panels), when compared with the no treatment controls (left two panels). Arrows show foci of residual tumors. Photos from both 100× and 800× magnifications are shown as indicated by footnotes in the figure.

To address whether ch806 could be effective against EGFR kinase domain mutation driven lung cancer, EGFR L858R-IRES-Luciferase/CCSP-rtTA mice were employed. Ch806 was administered at 0.5 mg/mouse every day for 4 weeks and serial MRI scanning of all treated mice was performed at the end of 1, 2, and 4 weeks of treatment. Tumor regression was observed after 2 weeks of ch806 treatment (21%±2%) and was 41%±2% at 4 weeks of ch806 treatment (FIG. 4A). Microscopically, the lungs of ch806-treated mice showed an increased diffuse cellular infiltrate with macrophages, especially in areas surrounding the remaining viable tumors. Furthermore, macrophages were present in multiple areas of the tumors, suggesting that macrophage-mediated cytotoxicity might be one of the underlying mechanisms of antibody-induced tumor regression (FIG. 4B). It should also be noted that the presence of consolidation within the lung due to increased accumulation of macrophages associated with tumor cells could overestimate tumor volume by MR imaging.

Discussion

EGFR mutations and activation events are common in human malignancies, including NSCLC. Activation of EGFR signaling can occur through receptor over expression as well as by constitutive signaling due to gain-of-function mutant forms of EGFR. Approximately 10-30% of NSCLC patients have EGFR kinase domain mutations in their lung tumors and about 5% of patients with squamous cell lung cancer have the specific EGFRvIII extracellular domain mutation (12, 20). Here we show that mAb806 and its humanized form, ch806, are effective in treating murine lung cancers with both types of EGFR mutations. The dramatic tumor regression observed was associated with blockage of EGFRvIII signaling and, consequently, increased apoptosis. The response to ch806 was not as impressive as that reported for erlotinib and cetuximab, in mice with lung tumors having EGFR kinase domain mutations, although they did have an objective response (41%±2%) radiographically and histologically(21, 23). In contrast, nearly complete tumor regression was achieved in mice with EGFRvIII driven lung tumors after treatment with mAb806, while cetuximab was without effect. This latter result is perhaps not surprising since cetuximab is designed to interfere with the interaction between ligand and the EGFR extracellular domain (24). It has been established that the EGFRvIII mutation leads to conformational changes and exhibits constitutive kinase activity independent of ligand stimulation which contributes to the tumor formation(25). Although cetuximab has been approved by the FDA for cancer patients, there is no clear biomarker to predict the efficacy of treatment with this antibody in individual patients, since response rates and overall survival are not correlated with EGFR protein expression by immunohistochemistry (14).

Although small molecule TKIs are effective in the treatment of many NSCLC patients with EGFR kinase domain mutations, all patients eventually develop resistance associated with a secondary mutation, T790M (10, 26). Consistently, in vitro studies have shown that tumor cells with T790M mutations are resistant to treatment with erlotinib (27, 28). Evidence from the crystal structure of the EGFR kinase domain with a secondary T790M mutation indicates that there should be little effect of T790M mutation on the receptor function. It may be that the T790M mutation interferes with erlotinib for its binding to the ATPase pocket (27). Nonetheless, the extracellular domain of the T790M mutant potentially provides a good target for antibody-based cancer therapy including cetuximab and mAb806. This could mean that NSCLC tumors with secondary T790M point mutations, which are resistant to small TKI treatment, might respond to mAb806 treatment. Efforts to generate mice harboring the compound mutant EGFR alleles containing both the activating kinase domain mutations and the T790M mutation are ongoing in order to test this hypothesis.

Recently released data from a Phase I clinical trial has shown that the ch806 antibody, unlike cetuximab, selectively binds to tumor cells of lung cancers, including squamous cell lung carcinoma, but not to normal tissues (Scott, ASCO 2006). No significant toxicities of the ch806 antibody were observed in this trial. In comparison with other EGFR targeted cancer therapies, including cetuximab and TKI treatments, ch806 appears to have a much greater specificity, by targeting a conformationally dependent epitope of the EGFR on cancer cells while sparing wt EGFR on most, if not all, normal cells. Our results clearly indicate the effectiveness of mAb 806 on blocking EGFR signaling. Thus, the unique targeting capabilities of ch806 represent a new and exciting paradigm for cancer-specific molecularly targeted therapy, which may benefit patients whose cancers are dependent upon uncontrolled EGFR signaling due to overexpression or to gain-of-function mutations including EGFRvIII or EGFR kinase domain mutations.

Methods

Mouse Cohorts.

The generation of Tet-op-EGFRvIII/CCSP-rtTA, Ink4A/Arf-/- mice and Tet-op-EGFR L858R-IRES-Luciferase/CCSP-rtTA mice were described previously (12, 21). All mice were housed in the pathogen-free environment at Harvard School of Public Health and all mouse experiments performed were approved by the Institutional Animal Care and Use Committee (IACUC). Littermates are used as controls in all experiments. To induce EGFRvIII and EGFR L858R expression, mice were fed with a doxycycline diet (Research Diets, Inc.). Doxycycline withdraw experiment in previous studies clearly identified that lung tumors from both alleles are soley dependent on doxycycline.

Targeted Therapies Using Either mAb806 or ch806 or Cetuximab in vivo.

Mice on continuous doxycycline diets for more than 8 weeks underwent MRI to document the lung tumor burden. MAb806 or ch806 (generated by the Ludwig Institute for Cancer Research, Melbourne, Australia) was delivered into mice bearing lung tumors through I.P. injection at daily 0.5 mg per doses. After a 1-week treatment, antibodies were administered every two days at the same dose for the additional indicated weeks. Cetuximab (obtained commercially from BMS pharmaceuticals) was administered to mice by I. P. injection at 1 mg per dose using the same dosing schedule. Mice were imaged with MRI at the indicated time points to determine reduction in tumor volume and then sacrificed for further histological and biochemical studies after the completion of treatment. All the mice were kept on the doxycycline diet throughout the experiments. Littermates were used as controls for all the drug treatment studies.

Pathologic Assessment of Lung Tumors.

Mice were euthanized at the indicated times and their left lungs were dissected and snap frozen for biochemical analysis. Their right lungs were then inflated under pressure (25 cm) with neutral buffered 10% formalin for 10 minutes and fixed overnight. Hematoxylin and eosin (H&E) stains were performed on 5 µm-thick sections from formalin-fixed, paraffin-embedded tumor samples in the Department of Pathology at Brigham and Women's Hospital.

Immunohistochemical analysis was performed on formalin-fixed paraffin sections. Slides were deparaffinized in xylene and rehydrated sequentially in ethanol. For antibodies requiring antigen retrieval, antigen-unmasking solution (Vector Laboratories) was used according to the manufacturer's instructions. Slides were quenched in hydrogen peroxide (0.3%-3%) to block endogenous peroxidase activity and then washed in automation buffer (Fisher Scientific). Slides were blocked in 5% normal serum for 1 hr at room temperature and then incubated overnight at 4° C. with primary antibody diluted in blocking buffer. The avidin biotin peroxidase complex method (Vector) was used, and slides were counterstained with hematoxylin. Slides were dehydrated sequentially in ethanol, cleared with xylene, and mounted with Permount (Fisher). Biotinylated DBA lectin (Vector) was used at 1:100. The antibodies used were total EGFR and phospho-EGFR Y1068 (1:50, Cell Signaling Technology). Apoptosis was measured by counting positive cells using the TUNEL assay (ApopTag kit; Intergen, Inc.).

Western Blot Analysis.

Snap frozen lung tissue samples were homogenized in RIPA buffer (Boston Bioproducts) containing the Complete Protease Inhibitors Cocktail and Phosphatase Inhibitors Cocktail Set I and II (EMD Biosciences). Lung lysates were cleared by centrifugation and boiled in 1× final sodium dodecyl sulfate (SDS) sample buffer (50 mM Tris (pH6.8), 10% glycerol, 0.715M β-mercaptoethanol, 2% SDS and 0.01% bromophenol blue) for 5 minutes. Lysates were then separated by SDS-polyacrylamide-gel electrophoresis (PAGE), transferred to nitrocellulose membranes and detected by immunoblotting with antibodies using SuperSignal West Pico Chemiluminescent Substrate (Pierce Biotechnology). The antibodies used in this study were directed against total EGFR, phospho-EGFR (pY1068), total Akt, phospho-AKT (pS473), total Erk1/2 and phospho-ERK 1/2 (pT202/pY204) (all from Cell Signaling); and β-actin (Santa Cruz Biotechnology, Inc.). Antibodies were used according to the conditions recommended by the manufacturer.

MRI and Tumor Volume Measurement.

Animals were anesthetized with 1.5-2% isoflurane (Iso-Flo®, Abbot Laboratories) mixed in 100% oxygen via a nose cone. In order to eliminate motion issues, both cardiac and respiratory gating was applied to all MRI studies. Since the acquisition of the MR signal is synchronized with the cardiac and respiratory cycles, the MR signal was acquired at each cardiac phase and at end-expiratory phase allowing motion artifacts to be significantly reduced.

MRI protocols optimized for assessing pulmonary parenchyma and vessels in normal mice (29) were adapted for operation at 4.7 Tesla (Biospec 47/40, Bruker BioSpin, Karlsruhe, Germany). The system is equipped with shielded gradient systems with a maximum power gradient of 30 G/cm, and a cardiac-respiratory triggering system (BioTrig, Bruker BioSpin, Karlsruhe, Germany). Then, the animals were placed prone with the electrodes (both fore pads and left rear pad) for cardiac gating and a respiratory sensor on their bodies, head first into the system, with the thorax centered with respect to the center of the radio frequency birdcage coil (inner diameter 3 cm). For the purpose of reproducible positioning of the imaging region, a low-resolution multi-slice image, serving as the end-expiratory phase localizer, was firstly acquired for the entire lung in both transverse and coronal planes using a fast spin echo sequence (RARE: rapid acquisition with relaxation enhancement, TR/effective TE=1000/28 msec, bandwidth=50 kHz, field of view=30 mm, matrix=128×128, slice thickness=1 mm, number of excitation=1). Further, two-dimensional (2D) multi-slice gradient echo imaging was performed in multi-slice transverse and coronal planes encompassing the entire lung with cardiac-respiratory gating. A pulse repetition time (TR) was selected less than the duration of one cardiac cycle (ranging 150 to 200 msec, average 178 msec), where one k-space line was filled for each image per single heartbeat. The minimum echo time (TE: 1.8 msec) was used to reduce the susceptibility effect arising from the interface between air/bone and tissue which would otherwise reduce the MR signal. Other scan parameters were: flip angle=22°, matrix size=256×256, field of view (FOV)=2.56 $cm^2$, slice thickness=1 mm, and number of excitation (NEX)=4, affording a 100 $\mu m^2$ in-plane resolution. Total scan time was approximately 6-7 minutes in each plane, depending on the individual animal's cardiac/respiratory rates. On each MR image, the areas indicating the pulmonary tumor were manually segmented and measured to calculate tumor volumes using ImageJ (ver. 1.33, National Institute of Health).

References

1. Ji, H., Sharpless, N. E., and Wong, K. K. 2006. EGFR Target Therapy: View From Biological Standpoint. *Cell Cycle.* 5(18):2072-2076. Epub 2006 Sep. 15.
2. Hynes, N. E., and Lane, H. A. 2005. ERBB receptors and cancer: the complexity of targeted inhibitors. *Nat. Rev. Cancer.* 5:341-354.
3. Arteaga, C. L. 2003. ErbB-targeted therapeutic approaches in human cancer. *Exp. Cell. Res.* 284:122-130.
4. Mendelsohn, J., and Baselga, J. 2000. The EGF receptor family as targets for cancer therapy. *Oncogene.* 19:6550-6565.
5. Snyder, L. C., Astsaturov, I., and Weiner, L. M. 2005. Overview of monoclonal antibodies and small molecules targeting the epidermal growth factor receptor pathway in colorectal cancer. *Clin. Colorectal Cancer.* 5 Suppl 2:S71-80.
6. Herbst, R. S. 2002. Targeted therapy in non-small-cell lung cancer. *Oncology (Williston Park).* 16:19-24.
7. Groner, B., Hartmann, C., and Wels, W. 2004. Therapeutic antibodies. *Curr. Mol. Med.* 4:539-547
8. Haber, D. A., et al. 2005. Molecular targeted therapy of lung cancer: EGFR mutations and response to EGFR inhibitors. *Cold Spring Harb Symp. Quant. Biol.* 70:419-426.
9. Park, K., and Goto, K. 2006. A review of the benefit-risk profile of gefitinib in Asian patients with advanced non-small-cell lung cancer. *Curr. Med. Res. Opin.* 22:561-573.
10. Sakurada, A., Shepherd, F. A., and Tsao, M. S. 2006. Epidermal growth factor receptor tyrosine kinase inhibitors in lung cancer: impact of primary or secondary mutations. *Clin. Lung Cancer.* 7 Suppl 4:S138-144.
11. Halatsch, M. E., Schmidt, U., Behnke-Mursch, J., Unterberg, A., and Wirtz, C. R. 2006. Epidermal growth factor receptor inhibition for the treatment of glioblastoma multiforme and other malignant brain tumours. *Cancer Treat. Rev.* 32:74-89.
12. Ji, H., et al. 2006. Epidermal growth factor receptor variant III mutations in lung tumorigenesis and sensitivity to tyrosine kinase inhibitors. *Proc. Natl. Acad. Sci. USA.* 103:7817-7822.

13. Sok, J. C., et al. 2006. Mutant epidermal growth factor receptor (EGFRvIII) contributes to head and neck cancer growth and resistance to EGFR targeting. *Clin. Cancer. Res.* 12:5064-5073.
14. Italiano, A. 2006. Targeting the epidermal growth factor receptor in colorectal cancer: advances and controversies. *Oncology.* 70:161-167.
15. Jungbluth, A. A., et al. 2003. A monoclonal antibody recognizing human cancers with amplification/overexpression of the human epidermal growth factor receptor. *Proc. Natl. Acad. Sci. USA.* 100:639-644.
16. Luwor, R. B., et al. 2001. Monoclonal antibody 806 inhibits the growth of tumor xenografts expressing either the de2-7 or amplified epidermal growth. factor receptor (EGFR) but not wild-type EGFR. *Cancer Res.* 61:5355-5361.
17. Mishima, K., et al. 2001. Growth suppression of intracranial xenografted glioblastomas overexpressing mutant epidermal growth factor receptors by systemic administration of monoclonal antibody (mAb) 806, a novel monoclonal antibody directed to the receptor. *Cancer Res.* 61:5349-5354.
18. Johns, T. G., et al. 2004. Identification of the epitope for the epidermal growth factor receptor-specific monoclonal antibody 806 reveals that it preferentially recognizes an untethered form of the receptor. *J. Biol. Chem.* 279:30375-30384.
19. Johns, T. G., et al. 2002. Novel monoclonal antibody specific for the de2-7 epidermal growth factor receptor (EGFR) that also recognizes the EGFR expressed in cells containing amplification of the EGFR gene. *Int. J. Cancer.* 98:398-408.
20. Shigematsu, H., and Gazdar, A. F. 2006. Somatic mutations of epidermal growth factor receptor signaling pathway in lung cancers. *Int. J. Cancer.* 118:257-262.
21. Ji, H., et al. 2006. The impact of human EGFR kinase domain mutations on lung tumorigenesis and in vivo sensitivity to EGFR-targeted therapies. *Cancer Cell.* 9:485-495.
22. Panousis, C., et al. 2005. Engineering and characterisation of chimeric monoclonal antibody 806 (ch806) for targeted immunotherapy of tumours expressing de2-7 EGFR or amplified EGFR. *Br. J. Cancer.* 92:1069-1077.
23. Politi, K., et al. 2006. Lung adenocarcinomas induced in mice by mutant EGF receptors found in human lung cancers respond to a tyrosine kinase inhibitor or to down-regulation of the receptors. *Genes. Dev.* 20:1496-1510.
24. Li, S., et al. 2005. Structural basis for inhibition of the epidermal growth factor receptor by cetuximab. *Cancer Cell.* 7:301-311.
25. Pedersen, M. W., and Poulsen, H. S. 2006. [Mutations in the epidermal growth factor receptor: structure and biological function in human tumors]. *Ugeskr. Laeger.* 168: 2354-236L
26. Janne, P. A., Engelman, J. A., and Johnson, B. E. 2005. Epidermal growth factor receptor mutations in non-small-cell lung cancer: implications for treatment and tumor biology. *J. Clin. Oncol.* 23:3227-3234.
27. Kobayashi, S., et al. 2005. EGFR mutation and resistance of non-small-cell lung cancer to gefitinib. *N. Engl. J. Med.* 352:786-792.
28. Kobayashi, S., et al. 2005. An alternative inhibitor overcomes resistance caused by a mutation of the epidermal growth factor receptor. *Cancer Res.* 65:7096-7101.
29. Kubo, S., et al. 2006. Three-dimensional magnetic resonance microscopy of pulmonary solitary tumors in transgenic mice. *Magn. Reson. Med.* 56:698-703.

EXAMPLE 2

806 Antibody Leads to Tumor Regression in Lung Tumors with EGFR T790M Mutation

Mice expressing the human EGFR secondary mutation T790M were generated. Mab806 was delivered into mice bearing lung tumors through I.P. injection at daily 0.5 mg per dose per mouse for 4 weeks. Serial MRI scanning of treated mice was performed at the end of 2 and 4 weeks of treatment as described below.

Generation of the Tet-op-hEGFR T790M-L858R/CCSP-rtTA Mouse Cohort

To generate mice with inducible expression of human EGFR T790M-L858R mutant, we constructed a 4.7-kb DNA segment consisting of seven direct repeats of the tetracycline (tet)-operator sequence, followed by EGFR T790M-L858R cDNA and ?-globin polyA. The construct was injected into FVB/N blastocysts and progeny were screened using PCR strategy. Fifteen Tet-op-hEGFR T790M-L858R founders were identified and then crossed to CCSP-rtTA mice (an allele been shown specifically targeting the expression of the reverse tetracycline trans-activator protein (rtTA) in type II alveolar epithelial cells (Fisher G H et al (2001) Genes Dev 15(24):3249-62) to generate inducible bitransgenic mouse cohorts harboring both the activator and the responder transgenes (Fisher G H et al (2001) Genes Dev 15(24):3249-62; Perl A K, Tichelaar J W, and Whitsett J A. (2002) Transgenic Res 11(1):21-9). Four tightly regulated hEGFR T790M-L858R (#17, #19, #24 and #29) founders were identified by RT-PCR analysis and the copy numbers from individual founders were determined by quantitative real-time PCR (Ji H et al (2006) Cancer Cell 9(6):485-95).

Tightly Regulated Expression of EGFR T790M-L858R in Lung Tissue at RNA level

The inducibility of EGFR mutant transgene expression in the lung compartment was evaluated at the RNA level by RT-PCR with human EGFR specific primers. The lungs of the bitransgenic mouse Tet-op-hEGFR T790M-L858R/CCSP-rtTA cohort for each potential founder were collected before and after 8 weeks of doxycycline administration and after 3 days of doxycycline withdrawal following doxycycline administration of an 8-week period. The EGFR mutant transcript was undetectable from either non-transgenic mice or the bitransgenic mice without doxycycline treatment, while it became readily detectable after 8-week doxycycline administration; transcription of mutant EGFR was completely abolished by 3 days of doxycycline withdrawal in all of the lines. To further confirm that the mutant EGFR transcripts is inducible and tightly regulated by doxycycline, RT-PCR using the same primers as described above and quantitative real time PCR was performed for lung samples collected at serial time points of doxycycline administration and withdrawal from founder #19. EGFR expression was observed after 1 week of doxycycline administration and was kept at a comparable level throughout the 8-week period of administration; doxycycline withdrawal is sufficient to block the expression of mutant EGFR, and no expression of the transgene was observed after 12 weeks of doxycycline withdrawal.

Over-expression of the EGFR T790M-L858R Mutant Drives the Development of Lung Adenocarcinomas with Bronchioloalveolar Features in Parenchyma and Papillary Adenocarcinoma in Airways To determine if over-expression of the hEGFR mutants drive lung tumorigenesis, bitransgenic hEGFR T790M-L858R/CCSP-rtTA mice on continuous doxycycline administration underwent serial magnetic resonance imaging (MRI) and were sacrificed at various time points for histological examination of the lungs. Tumors could only be observed by MRI after 5-6 weeks of doxycycline administration and tumor volume, as defined by MRI, increased following prolonged doxycycline treatment. In contrast to untreated mice, early lesions started to develop in parenchyma of the lungs after 2-3 weeks of doxycycline treatment. After 4-5 weeks, typical BAC appeared.

Invasive adenocarcinoma with bronchioloalveolar features appeared after 7-9 weeks and become the dominant histological pattern after 12 weeks of doxycycline treatment. The lung parenchymal adenocarcinomas observed in our mouse model is histologically similar to that of EGFR L858R mouse model described previously (Ji, H., et al. (2006) Cancer Cell 9:485-495; Politi, K., et al. (2006) Genes Dev. 20:1496-1510) and also similar to that seen in a subset of NSCLC patients who originally responded to erlotinib.

In addition to parenchymal adenocarcinomas, hEGFR T790M-L858R/CCSP-rtTA mice also developed bronchial papillary adenocarcinomas. Early papillary neoplasia in the bronchioles was observed after 2-3 weeks of continuous doxycycline administration, and then developed into adenocarcinoma within additional 6 to 8 weeks. All of the four founders showed similar morphologic features and a similar latency of tumorigenesis. Bronchial tumors were found in all of the 4 founders of hEGFR T790M-L858R/CCSP-rtTA mice identified in the current study, but were absent in all of our EGFR L858R mice. Occasionally, metastatic foci of adenocarcinoma could be observed in lymph nodes of the mice that develop EGFR T790M-L858R driven lung tumors but not of the mice that has EGFR L858R driven tumors. IHC staining for both bronchial and parenchymal tumors with specific cell markers shows different patterns of differentiation. Prosurfactant protein C(SPC) is a unique biomarker for type II pneumocytes in the alveoli, while Clara cell secretory protein (CCSP) is specific to Clara cell in bronchiolar epithelium. The majority of parenchymal tumors show intensive SPC staining, implying a type II pneumocyte origin, as expected. In contrast, the bronchial tumors were negative for SPC. Interestingly, only a small subset of bronchial tumor cells is positive for CCSP. This could be possibly explained by Clara cell origin followed by poor differentiation which led to loss of the CCSP expression marker.

Expression of the hEGFR T790M-L858R Mutants is Essential for Tumor Maintenance of Both Parenchymal and Bronchial Adenocarcinomas Both bronchial and parenchymal lung adenocarcinomas from hEGFR T790M-L858R/CCSP-rtTA mice were positively stained by total and phospho-EGFR antibodies, indicating that the expressed EGFR mutant is functionally active. After 3 days of doxycycline withdrawal, no positive signals from either of the antibodies were observed, implying that both types of tumors are driven by and dependent on EGFR T790M-L858R for their survival. We also observed an increase in positive staining of terminal deoxynucleotidyl-transferase-mediated dUTP-biotin nick end labeling (TUNEL) assay after doxycycline withdrawal, indicating the apoptotic process had been triggered.

Consistent with the apoptosis suggested by TUNEL staining, MRI results demonstrate that EGFR T790M-L858R driven lung tumor completely regressed after 10 days of doxycycline withdrawal. Microscopic analysis of the lungs from the same mouse that examined by MRI shows grossly normal lung histology. No tumor lesions were found in either airways or parenchyma after 12 weeks of doxycycline withdrawal in other tumor bearing mice.

To better quantify mutant EGFR expression in tumors at the protein level, we performed western blotting using whole lung lysates from bitransgenic mice after different times of doxycycline administration. Although individual differences exist, EGFR phosphorylation was tightly regulated by doxycycline and was synchronized with the presence of tumors, confirming the essential role of mutant EGFR signaling in tumor maintenance as observed in IHC staining and MRI. Therefore, EGFR remains an attractive therapeutic target for our novel mouse lung cancer model.

Treatment of EGFR T790M-L858R Driven Lung Tumors with mAb806

Figure 5:
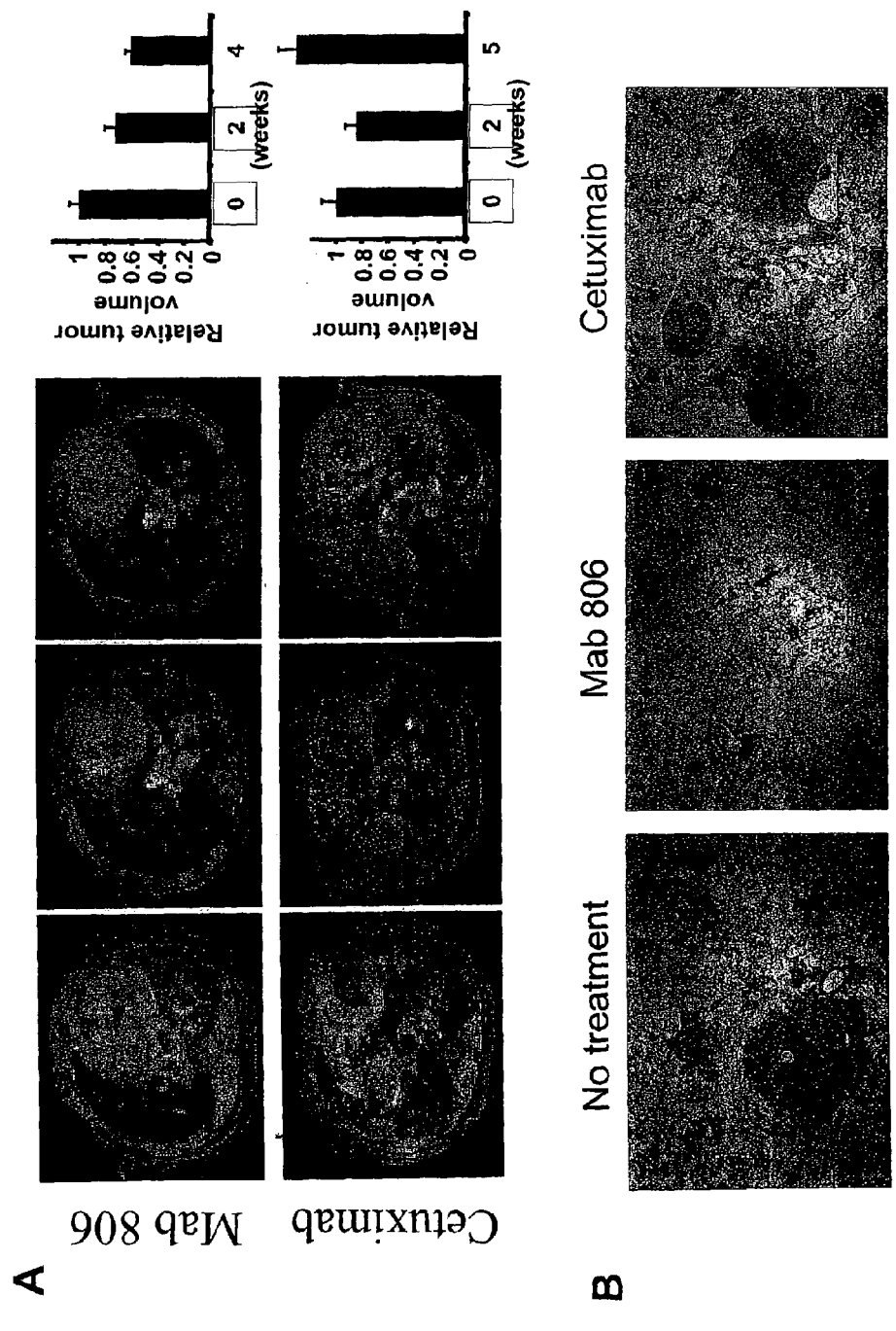
FIGS. 5A and 5B depicts the results of treatment of EGFR T790M-L858R lung tumors with mAb806 versus cetuximab. Mice on continuous doxycycline diets for more than 8 weeks underwent MRI to document the tumor burden. Mab806 was delivered into mice bearing lung tumors through I.P. injection daily at 0.5 mg doses for 4 weeks. Cetuximab was administered to mice by I.P. injection at 1 mg per dose daily for 4 weeks. Littermates were used as controls for all the treatment studies (no treatment). (A) Mice were imaged with MRI at 0, 2, and 4 or 5 weeks to determine reduction in tumor volume. (B) After completion of treatment and MRI imaging, mice were sacrificed for further histological and biochemical studies.

The results of treatment of EGFR T790M-L858R lung tumors with mAb806 versus cetuximab is depicted in FIG. 5. Mice on continuous doxycycline diets for more than 8 weeks underwent MRI to document the tumor burden. Mab806 was delivered into mice bearing lung tumors through I.P. injection daily at 0.5 mg doses for 4 weeks. Cetuximab was administered to mice by I.P. injection at 1 mg per dose daily for 4 weeks. Mice were imaged with MRI at 0, 2, and 4 or 5 weeks to determine reduction in tumor volume. Tumor volume was reduced at 2 weeks (over 20%) and more significantly at 4 weeks (over 30%) by treatment with mAb806. While tumor volume was initially reduced at 2 weeks by treatment with cetuximab, tumor volume grew significantly by 5 weeks of treatment with cetuximab (tumor volume observed at 5 weeks of cetuximab treatment was greater than original volume at 0 weeks). After completion of treatment and MRI imaging, mice were sacrificed for further histological and biochemical studies. Littermates were used as controls for all the treatment studies (no treatment).

This invention may be embodied in other forms or carried out in other ways without departing from the spirit or essential characteristics thereof. The present disclosure is therefore to be considered as in all aspects illustrate and not restrictive, the scope of the invention being indicated by the appended Claims, and all changes which come within the meaning and range of equivalency are intended to be embraced therein.

Various references are cited throughout this Specification, each of which is incorporated herein by reference in its entirety.

What is claimed is:

1. A method of treating tyrosine kinase inhibitor resistant EGFR-mediated lung cancer in a mammal, wherein said resistant EGFR-mediated lung cancer is a result of a secondary mutation at position 790 of EGFR (T790M) to generate a mutant EGFR, said method comprising administering to said mammal in need of treatment of said tyrosine kinase inhibitor resistant EGFR-mediated lung cancer an effective amount of an anti-EGFR antibody capable of binding to and inhibiting the mutant EGFR, wherein said antibody is mAb806 antibody or an active fragment thereof.

2. The method of claim 1 wherein mAb806 is a humanized antibody.

3. The method of claim 1, wherein the lung cancer is lung adenocarcinoma.

4. The method of claim 1, wherein mAb806 is a recombinant antibody.

5. The method of claim 1, wherein the lung cancer is lung squamous cell carcinoma.

6. The method of claim 1, wherein the lung cancer is non-small cell lung cancer.

7. The method of claim 1, wherein said antibody is labeled with a detectable or functional label.

8. The method of claim 7, wherein said detectable or functional label is a radiolabel.

9. The method of claim 7, wherein said detectable or functional label is a cytotoxic drug.

10. A method for reducing EGFR-mediated lung tumor growth in a cancer patient, wherein said cancer patient has been previously treated with one or more tyrosine kinase inhibitor and has developed recurrent disease and lung tumor growth, wherein the cancer patient has developed a secondary EGFR mutation which is T790M, comprising administering to said patient an effective amount of an anti-EGFR antibody such that the recurrent disease and lung tumor growth is inhibited and reduced, wherein said antibody is mAb806 antibody or an active fragment thereof.

11. The method of claim 10, wherein mAb806 is a humanized antibody.

12. The method of claim 10, wherein mAb806 is a recombinant antibody.

13. The method of claim 10 wherein the lung tumor is lung adenocarinoma.

14. The method of claim 10, wherein the lung tumor is lung squamous cell carcinoma.

15. The method of claim 10, wherein the lung tumor is non-small cell lung cancer.

16. The method of claim 10, wherein said antibody is labeled with a detectable or functional label.

17. The method of claim 16, wherein said detectable or functional label is a radiolabel.

18. The method of claim 16, wherein said detectable or functional label is a cytotoxic drug.

* * * * *

UNITED STATES PATENT AND TRADEMARK OFFICE
CERTIFICATE OF CORRECTION

Page 1 of 1

PATENT NO. : 9,090,693 B2
APPLICATION NO. : 12/449129
DATED : July 28, 2015
INVENTOR(S) : Kwok-Kin Wong It is certified that error appears in the above-identified patent and that said Letters Patent is hereby corrected as shown below:

In the Specification

Column 1 Line 13 after the section entitled, "FIELD OF THE INVENTION", please insert the following:
-- STATEMENT REGARDING FEDERALLY SPONSORED RESEARCH OR DEVELOPMENT
This invention was made with government support under grant numbers CA095676, CA122794, and AG024004 awarded by The National Institutes of Health. The government has certain rights in the invention. --

Signed and Sealed this
Seventh Day of July, 2020

Andrei Iancu
*Director of the United States Patent and Trademark Office*